United States Patent
Campbell et al.

(10) Patent No.: US 11,845,943 B2
(45) Date of Patent: Dec. 19, 2023

(54) HAPLOID INDUCER LINE FOR ACCELERATED GENOME EDITING

(71) Applicant: Regents of the University of Minnesota, Minneapolis, MN (US)

(72) Inventors: Benjamin W. Campbell, Falcon Heights, MN (US); Junqi Liu, Roseville, MN (US); Robert M. Stupar, Arden Hills, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 2 days.

(21) Appl. No.: 17/541,109

(22) Filed: Dec. 2, 2021

(65) Prior Publication Data

US 2022/0186241 A1 Jun. 16, 2022

Related U.S. Application Data

(62) Division of application No. 15/741,002, filed as application No. PCT/US2016/040398 on Jun. 30, 2016, now Pat. No. 11,193,131.

(60) Provisional application No. 62/318,913, filed on Apr. 6, 2016, provisional application No. 62/186,913, filed on Jun. 30, 2015.

(51) Int. Cl.
| | |
|---|---|
| C12N 15/82 | (2006.01) |
| A01H 1/06 | (2006.01) |
| A01H 1/08 | (2006.01) |
| C12N 9/22 | (2006.01) |
| C12N 15/11 | (2006.01) |

(52) U.S. Cl.
CPC ........... *C12N 15/8213* (2013.01); *A01H 1/06* (2013.01); *A01H 1/08* (2013.01); *C12N 9/22* (2013.01); *C12N 15/11* (2013.01); *C12N 2310/20* (2017.05); *C12N 2800/80* (2013.01)

(58) Field of Classification Search
CPC .................................................. C12N 15/8213
See application file for complete search history.

(56) References Cited

U.S. PATENT DOCUMENTS

| | | | |
|---|---|---|---|
| 5,593,874 A | 1/1997 | Brown et al. | |
| 7,244,876 B1 | 7/2007 | Kuchuk et al. | |
| 8,269,061 B2 * | 9/2012 | Williams ................ | A01H 1/08 800/275 |
| 8,269,081 B1 | 9/2012 | Grote et al. | |
| 9,677,082 B2 | 6/2017 | Chintamanani et al. | |
| 10,487,336 B2 * | 11/2019 | Michelmore ...... | C12N 15/8213 |
| 10,519,456 B2 | 12/2019 | Que et al. | |
| 11,193,131 B2 | 12/2021 | Campbell et al. | |
| 2003/0005479 A1 | 1/2003 | Kato | |
| 2008/0079567 A1 | 4/2008 | Poor | |
| 2008/0216198 A1 | 9/2008 | Zhao et al. | |
| 2011/0203012 A1 | 8/2011 | Dotson et al. | |
| 2013/0198893 A1 | 8/2013 | Zhao et al. | |
| 2014/0283166 A1 | 9/2014 | Chomet et al. | |
| 2015/0067922 A1 | 3/2015 | Yang et al. | |
| 2015/0307889 A1 | 10/2015 | Petolino et al. | |
| 2017/0240912 A1 | 8/2017 | Chintamanani et al. | |
| 2018/0245090 A1 | 8/2018 | Campbell et al. | |
| 2020/0080097 A1 | 3/2020 | Que et al. | |

FOREIGN PATENT DOCUMENTS

| | | |
|---|---|---|
| EP | 2574234 | 9/2011 |
| WO | WO 01/85969 | 11/2001 |
| WO | WO 2004/067736 | 8/2004 |
| WO | WO 2006/079567 | 8/2006 |
| WO | WO 2011/072246 | 6/2011 |
| WO | WO 2012/129373 | 9/2012 |
| WO | WO 2014/096972 | 6/2014 |
| WO | WO 2014/110274 | 7/2014 |
| WO | WO 2015/171894 | 11/2015 |
| WO | WO 2016/075255 | 5/2016 |
| WO | WO 2016/106121 | 6/2016 |
| WO | WO 2016/177887 | 11/2016 |
| WO | WO 2017/004375 | 1/2017 |
| WO | WO 2017/087682 | 5/2017 |
| WO | WO 2018/015956 | 1/2018 |
| WO | WO 2018/015957 | 1/2018 |
| WO | WO 2018/052919 | 3/2018 |

OTHER PUBLICATIONS

Zhang, H. et al., Plant Biotechnology Journal (May 23, 2014) vol. 12, pp. 797-807. (Year: 2014).*
Gurushidze, M. et al., PLOS One; Mar. 2014, vol. 9, No. 3; pp. 1-9. (Year: 2014).*
Arimondo et al., "Exploring the cellular activity of camptothecin-triple-helix-forming oligonucleotide conjugates," Mol. Cell Biol., 26:324-333 Jan. 2006.
Baker, "Gene-editing nucleases," Nat. Methods, 9:23-26, Jan. 2012.
Belhaj, K. et al., Plant Methods; 2013 vol. 9, No. 39, pp. 1-10. (Year: 2013).
Brink and Williams, "Mutable R-navajo alleles of cyclic origin in maize," Genetics, 73(2):273-296, Feb. 1973.
Cermak et al., "Efficient design and assembly of custom TALEN and other TAL effector-based constructs for DNA targeting," Nucleic Acids Res., 39(12):e82, Jul. 2011.
Chen and Hayes, "A comparison of Hordeum bulbosum-mediated haploid production efficiency in barley using in vitro floret and tiller culture," Theor. Appl. Genet., 77(5):701-704, May 1989.
Chen et al., "Wide hybridization of Hordeum vulgare× Zea mays," Genome, 34(4):603-605, Aug. 1991.
Cheng et al., "Genetic Transformation of Wheat Mediated by Agrobacterium tumefaciens," Plant Physiol., 115(3):971-980, Nov. 1997.

(Continued)

*Primary Examiner* — Russell Kallis
(74) *Attorney, Agent, or Firm* — Fish & Richardson P.C.

(57) ABSTRACT

Provided herein are materials and in planta methods for using haploid inducer lines containing a targeted endonuclease to generate transgenic or non-transgenic plants with targeted mutations and/or genomic modifications. Also provided herein.

12 Claims, 7 Drawing Sheets

Specification includes a Sequence Listing.

(56) References Cited

OTHER PUBLICATIONS

Clough and Bent, "Floral dip: a simplified method for Agrobacterium-mediated transformation of *Arabidopsis thaliana*," Plant J., 16(6):735-743, Dec. 1998.
Curtin et al., "Targeted mutagenesis of duplicated genes in soybean with zinc-finger nucleases," Plant Physiol., 156(2):466-473, Jun. 2011.
Devaux, P. "The *Hordeum bulbosum* (L.) method." Doubled Haploid Production in Crop Plants. Springer, Dordrecht, 15-19, 2003.
Eisenschmidt et al., "Developing a programmed restriction endonuclease for highly specific DNA cleavage," Nucleic Acids Res., 33(22):7039-7047, Dec. 2005.
Extended European Search Report in European Application No. 16818789.6 dated Nov. 28, 2018, 17 pages.
Faris et al., "A unique wheat disease resistance-like gene governs effector-triggered susceptibility to necrotrophic pathogens," Proc. Natl. Acad. Sci. USA., 107(30):13544-13549, Jul. 2010.
Gallego et al., "Ku80 plays a role in non-homologous recombination but is not required for T-DNA integration in *Arabidopsis*," Plant J., 35(5):557-565, Sep. 2003.
Gasparis et al., "Agrobacterium-mediated transformation of oat (*Avena sativa* L.) cultivars via immature embryo and leaf explants," Plant Cell Rep., 27(11):1721-1729, Nov. 2008.
GenBank Accession No. AB259782.1, "*Hordeum vulgare* subsp. vulgare Vrs1 gene for homeodomain leucine zipper protein Vrs1, complete cds, allele: Vrs1.b," Jan. 17, 2007, 2 pages.
GenBank Accession No. GU259618, "*Triticum turgidum* subsp. durum cultivar Langdon Tsn1 (Tsn1) gene, complete cds; and retrotransposon, complete sequence," Jun. 29, 2010, 2 pages.
Gherbi et al., "Homologous recombination in planta is stimulated in the absence of Rad50," EMBO Rep., 2(4):287-291, Apr. 2001.
Gilles et al., "Loss of Pollen-Specific Phospholipase Not Like Dad triggers gynogenesis in Maize," EMBO Journal, 36(6):707-717, Feb. 22, 2017.
Gordon-Kamm et al., "Transformation of Maize Cells and Regeneration of Fertile Transgenic Plants," Plant Cell, 2(7):603-618, Jul. 1990.
Gu et al., "R gene expression induced by a type-III effector triggers disease resistance in rice," Nature, 435(7045):1122-1125, Jun. 2005.
Hahn et al. "An Efficient Visual Screen for CRISPR/Cas9 Activity in *Arabidopsis thaliana*," Front. Plant Science, 8:39, Jan. 24, 2017, 13 pages.
Hermsen and Verdenius, "Selection from Solanum tuberosum group Phureja of genotypes combining high-frequency haploid induction with homozygosity for embryo-spot," Euphytica, 22(2):244-259, Jun. 1973.
Hicks et al., "Three classes of nuclear import signals bind to plant nuclei," Plant Physiol., 107(4):1055-1058, Apr. 1995.
Huang et al., "Cloning of an *Arabidopsis* Patatin-Like Gense, Sturdy, by activation T-DNA Tagging," Plant Physiology, 125(2):573-584, Feb. 2001.
Ishida et al., "High efficiency transformation of maize (*Zea mays* L.) mediated by Agrobacterium tumefaciens," Nature Biotechnol., 14(6):745-750, Jun. 1996.
Jia et al., "Agrobacterium tumefaciens T-DNA Integration and Gene Targeting in *Arabidopsis thaliana* Non-Homologous End-Joining Mutants," J. Botany, 2012.
Jinek et al., "A programmable dual-RNA-guided DNA endonuclease in adaptive bacterial immunity," Science, 337:816-821, Jun. 2012.
Kalish and Glazer, "Targeted genome modification via triple helix formation," Ann. NY. Acad. Sci., 1058:151-161, Nov. 2005.
Kasha and Kao, "High frequency haploid production in barley (*Hordeum vulgare* L.)," Nature, 225(5235):874-876, Feb. 1970.
Kay et al., "A bacterial effector acts as a plant transcription factor and induces a cell size regulator," Science, 318(5850):648-651, Oct. 2007.
Kelliher et al., "MATRILINEAL, A Sperm-Specific Phospholipase, Triggers Maize Haploid Induction," Nature, 542(7639):105-109, Jan. 23, 2017.

Kew Chromosome Conference Proceedings III, Brandham (Ed.), Norwich, UK: The Stationery Office Books, pp. 167-177, 1988).
Knox et al., "Dicamba and growth condition effects on doubled haploid production in durum wheat crossed with maize," Plant Breeding, 119(4):289-298, Aug. 2000.
Laurie and Bennett, "Chromosome behavior in wheat × maize, wheat × sorghum and barley × maize crosses," In Kew Chromosome Conference Proceedings III, Brandham (Ed.), Norwich, UK: The Stationery Office Books, pp. 167-177, 1988.
Li et al., "Multiplex and homologous recombination-mediated genome editing in *Arabidopsis and* Nicotiana benthamiana using guide RNA and Cas9," Nat. Biotechnol., 31(8):688-691, Aug. 2013.
Liang et al., "Targeted mutagenesis in *Zea mays* using TALENs and the CRISPR/Cas system," J. Genet. Genomics, 41(2):63-68, Feb. 2014.
Liu et al., "A 4bp Insertion at ZmPLA1 Encoding a Putative Phospholipase A Generates Haploid Induction in Maize," Mol. Plant, 10(3):520-522, Feb. 4, 2017.
Louwerse et al., "Stable recombinase-mediated cassette exchange in *Arabidopsis* using Agrobacterium tumefaciens," Plant Physiol., 145(4):1282-1293, Dec. 2007.
Makarova et al., "Evolution and classification of the CRISPR-Cas systems," Nat. Rev. Microbiol., 9(6):467-477, Jun. 2011.
Mali et al., "RNA-guided human genome engineering via Cas9," Science, 339(6121):823-826, Feb. 2013.
Maluszynski et al., Double Haploid Production in Crop Plants, pp. 53-58, Kluwer Academic Publishers, Dordrecht, Netherlands, 2003.
Maluszynski et al., Double Haploid Production in Crop Plants: A Manual, pp. 135-140, Dordrecht, Netherlands: Kluwer Academic Publishers, 2003.
Maluszynski et al., Double Haploid Production in Crop Plants: A Manual, pp. 155-159, Kluwer Academic Publishers, Dordrecht, Netherlands, 2003.
Muiruri et al., "Expressed Centromere Specific Histone 3 (CENH3) Variants in Cultivated Triploid and Wild Diploid Bananas (*Musa* spp.)," Front. Plant Science, 8:1034, Jun. 29, 2017, 12 pages.
Nair et al., "Dissection of a major QTL qhir1 conferring maternal haploid induction ability in maize," Theor. Appl. Genetics, 130(6):1113-1122, Mar. 18, 2017.
Nishizawa-Yokoi et al., "Suppression of Ku70/80 or Lig4 leads to decreased stable transformation and enhanced homologous recombination in rice," New Phytologist, 196(4):1048-1059, Dec. 2012.
Ow, "2004 SIVB Congress Symposium Proceeding: Transgene management via multiple site-specific recombination systems," In Vitro Cellular & Developmental Biology-Plant, 41(3):213-219, May 2005.
PCT International Search Report in International Application No. PCT/US2016/040398 dated Sep. 22, 2016, 3 pages.
Peloquin et al., "Genetic variation among haploids of the common potato," Am. J. Potato, 37(9):289-297, Sep. 1960.
Porteus and Carroll, "Gene targeting using zinc finger nucleases," Nat. Biotechnol., 23(8):967-973, Aug. 2005.
Prigge and Melchinger, "Production of haploids and doubled haploids in maize," Methods Mol Biol., 877:161-72, 2012.
Qi et al., "Increasing frequencies of site-specific mutagenesis and gene targeting in *Arabidopsis* by manipulating DNA repair pathways," Genome Res., 23(3):547-554, Mar. 2013.
Qi et al., "Repurposing CRISPR as an RNA-guided platform for sequence-specific control of gene expression," Cell., 152(5):1173-1183, Feb. 2013.
Ravi and Chan, "Haploid plants produced by centromere-mediated genome elimination," Nature, 464(7288):615-618, Mar. 2010.
Reiss et al., "RecA stimulates sister chromatid exchange and the fidelity of double-strand break repair, but not gene targeting, in plants transformed by Agrobacterium," Proc. Natl. Acad. Sci. USA., 97(7):3358-3363, Mar. 2000.
Rietz et al., "Roles of *Arabidopsis* Patatin-Related Phospholipases A in Root Development Are Related to Auxin Responses and Phosphate Deficiency," Mol. Plant, 3(3):524-538, Jan. 6, 2010.
Römer et al., "Plant pathogen recognition mediated by promoter activation of the pepper Bs3 resistance gene," Science, 318:645-648, Oct. 2007.

(56) References Cited

OTHER PUBLICATIONS

Sander et al., "Selection-free zinc-finger-nuclease engineering by context-dependent assembly (CoDADA)," Nature. Met. 8(1):67-69, Jan. 2011.
Scherer et al., "Patatin-Related Phospholipase A: Nomenclature, Subfamilies and Functions in Plants," Trends Plant Science, 15(12):693-700, Oct. 18, 2010.
Schornack et al., "Gene-for-gene-mediated recognition of nuclear-targeted AvrBs3-like bacterial effector proteins," J. Plant Physiol., 163(3):256-272, Feb. 2006.
Shalev et al., "Stimulation of homologous recombination in plants by expression of the bacterial resolvase ruvC," Proc. Natl. Acad. Sci. USA., 96(13):7398-7402, Jun. 1999.
Shukla et al., "Precise genome modification in the crop species *Zea mays* using zinc-finger nucleases," Nature, 459(7245):437-441, May 2009.
Simon et al., "Targeting DNA with triplex-forming oligonucleotides to modify gene sequence," Biochimie., 90(8):1109-1116, Aug. 2008.
Somers et al., "Fertile, transgenic oat plants," Nature Biotechnol., 10(12):1589-1594, Dec. 1992.
Sugio et al., "Two type III effector genes of *Xanthomonas oryzae* pv. oryzae control the induction of the host genes OsTFIIAgamma1 and OsTFX1 during bacterial blight of rice," Proc. Natl. Acad. Sci. USA, 104(25):10720-10725, Jun. 2007.
Tanaka et al., "High efficient gene targeting on the AGAMOUS gene in an *Arabidopsis* AtLIG4 mutant," Biochem. Biophys. Res. Commun., 396(2):289-293, May 2010.
Tingay et al., "Agrobacterium tumefaciens-mediated barley transformation," Plant J., 11(6):1369-1376, Dec. 1997.
Travella et al., "A comparison of transgenic barley lines produced by particle bombardment and Agrobacterium-mediated techniques," Plant Cell Rep., 23(12):780-789, Mar. 2005.
U.S. Declaration of Timothy Kelliher in Issued U.S. Pat. No. 10,519,456, dated May 22, 2019, 2 pages.
U.S. Interview Summary in Issued U.S. Pat. No. 10,519,456, dated Aug. 9, 2019, 2 pages.
U.S. Non-Final Office Action in Issued U.S. Pat. No. 10,519,456, dated Feb. 25, 2019, 13 pages.
U.S. Notice of Allowance in Issued U.S. Pat. No. 10,519,456, dated Aug. 9, 2019, 10 pages.
U.S. Response to Non-Final Office Action in Issued U.S. Pat. No. 10,519,456, dated May 23, 2019, 7 pages.
Voytas, "Plant genome engineering with sequence-specific nucleases," Annu. Rev. Plant Biol., 64:327-350, May 2013.
Wan et al., "Efficient production of doubled haploid plants through colchicine treatment of anther-derived maize callus," Theor. Appl. Genet., 77(6):889-892, Jun. 1989.
Wedzony et al., "Production of doubled haploids in triticale (× Triticosecale Wittm.) by means of crosses with maize (*Zea mays* L.) using picloram and dicamba," Plant Breed., 117(3):211-215, Jul. 1998.
Wedzony et al., "Factors influencing triticale doubled haploid production by means of crosses with maize," In: Proceedings of the 4th International Triticale Symposium, Red Deer, Canada. vol 1. Juskiw (Ed.) International Triticale Association, Alberta, Canada, pp. 45-52, 1998.
Weeks et al., "Rapid Production of Multiple Independent Lines of Fertile Transgenic Wheat (*Triticum aestivum*)," Plant Physiol., 102(4):1077-1084, Aug. 1993.
Weinthal et al., "Genome editing in plant cells by zinc finger nucleases," Trends in Plant Science, 15(6):308-21, Jun. 2010.
Yang et al., "Os8N3 is a host disease-susceptibility gene for bacterial blight of rice," Proc. Natl. Acad. Sci. USA., 103(27):10503-10508, Jul. 2006.
Zhang et al., "Genetic transformation of commercial cultivars of oat (*Avena sativa* L.) and barley (*Hordeum vulgare* L.) using in vitro shoot meristematic cultures derived from germinated seedlings," Plant Cell Reports, 18(12):959-966, Sep. 1999.
Zhang et al., "Production of Multiple Shoots from Shoot Apical Meristems of Oat (*Avena sativa* L.)," J. Plant Physiol., 148(6):667-671, 1996.
Zimny et al., "Fertile, transgenic Triticale (×Triticosecale Wittmack)," Molecular Breeding, 1(2):155-164, Jun. 1995.

\* cited by examiner

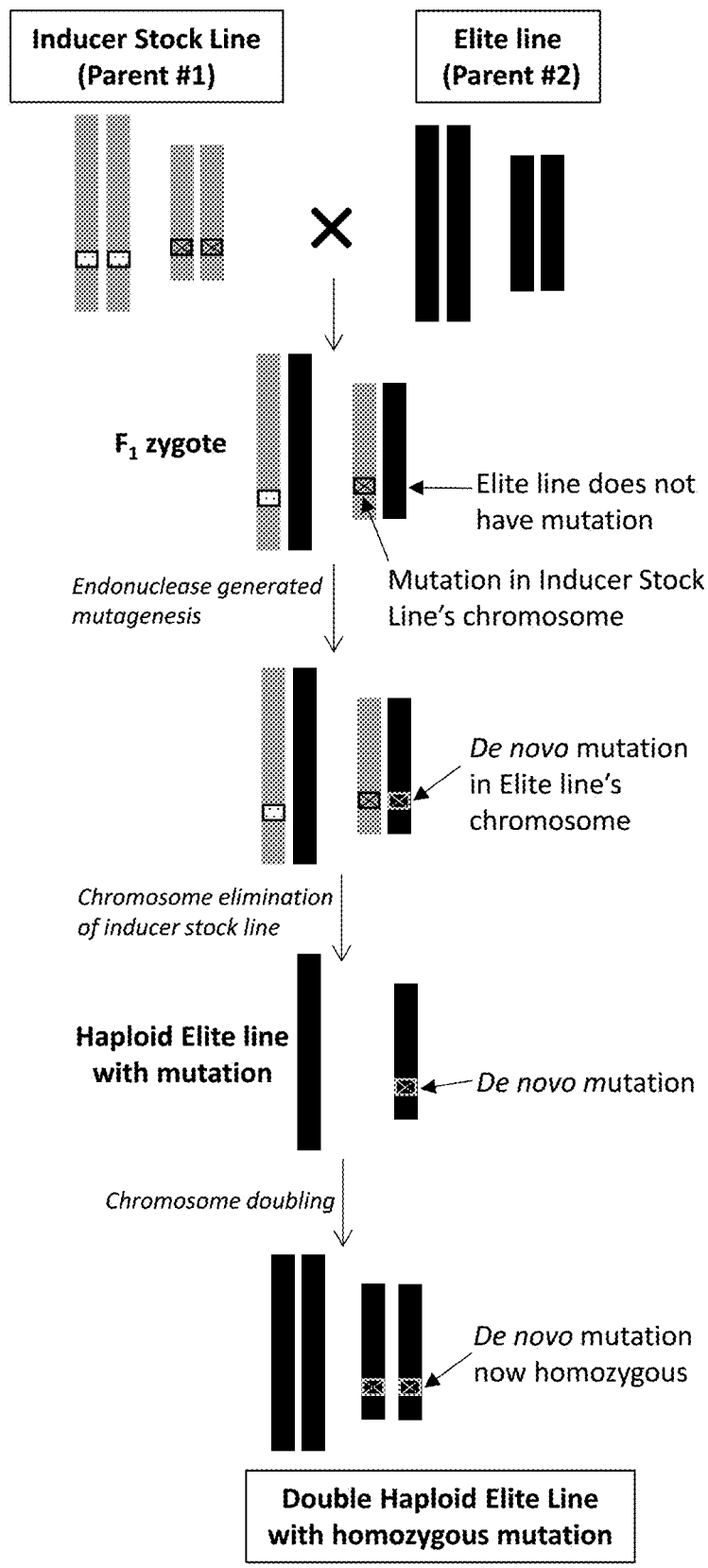

FIG. 4

```
ATGGATAAGAAGTACTCCATCGGACTGGATATCGGAATCAACTCCGTGGATGGGCTGTGATCACTGATGAGTACCAAGGTGCCATCGAAGAAGTTCAAGGTGCTGGG
AAACACTGATAGACACTCCATCAAGAAGAACCTGATCGGAGCTCTGCTTCCAACGACTTGCTTCCAAGGACTGCTGAGACTGCTAGACTGTGAGGAACTGCTAGAAGAT
ACACTAGAAGAAGAACAGAATCTGCTACCTGCAGAGATCTTCGATAAGGTGGATGATTCCTTCTTCCACAGACTGGAGGAGTCCTTCCTGGTG
GAGGAGGATAAGAAGCACGAGCACCCCAATCTTCGGAAACATCGGCTCTGGCTCTACCCAACTATCTACCACCTGAGAAGAAGCTGGT
GGATTCCCACTGATAAGCTGTTCATCCAACTGGTGCAAACCTTACAACTGTTCGAGGAGACACTTCCGAGGAGATCTGAACCCAGATAACT
CCGATGTGGATAAGCTGTTTCATCCAACTGATCGTTCGAAGAACCTGATCGTTCCAGGAGAACGACTGTTCGGAAACCTGATCGCTCTGTCCGGACTGACTCC
AGACTGTCCAAGTCCAAGTTCGATCTGCTTCGGATGGTAAGCTCCAACTGTCCAACTGTCTGCTGTCCGATATATCCTGGATGATCGTTGGATAACCTGGAGATCAAT
AAACTTCAAGTCCAACTTCGATCTGGCTGGTAAGAACCTGTTCCTGGCTAGTCCATATCCTGGTGAGCAATCAAGAAGTACAAGGAGATCTTCTTCGATCAATCCAAGAA
ATCAAGAGATACGATGAGCACCAAGAATCTGACTCTGCTGAAGGCTCTGAAGACTTCATCAAGCCAGAAGAAGATGGATGAAGATGGATGACGCTGTCGGTGAAGC
CGGATACGCTGGATACATCGATCGGAGGAGCTTCTACAAGTTCATCAAGCCCATCAACAACCTGACTTTCGATAACGGGATCCTGGAGAGCTGAGAGCTGCTGGTGAAGGAT
TGAACACAGAGAGGATCTGCTGAAGGATAACAGAGAAGATCTGAGAAGGATAACTTCGAGGAGAAGATCCATTTCAGAGATCCCATATCCATCTGACTTTCAGAACTTCGCTTG
TTTCACCCATTCCTGAAGGATAACAGAGATACACTCCATGGAGGAGTTGTGGTACAGAGGAGTTCATGGGAGCTGTACAAGAGCTAAGGATGACTGATTGGATTGCTACTCGCTTG
GATGACTAGAAAGTCCGAGGAGATAACAGGACTCTGCCAAAAGAGAGGTGCTGCCAAAAGAGAGAATCACTCCTCATCGGAGGAGGTCATTCGTGAAAGATCGGATGGAATTACTTCAAGGAATGAGA
AGAACCTGCCAAACGAGAAGTGCTGACAAAGAGAAGAGACACTCCCTGGAGTAACAGATGGCTAACGAGCTGTGTACCAAAGAACTGACAAAACCCTGGATCTGCTGAAGGACTTACCTGCAAAACGGAAGAG
AAGCCAGCTTCCTGTCCGATTCCGTGGAGATCTCCGGAGGAGATATCCTGGAGCTGGGATCGGTCCCTTGTCAAGACTTACCGACGATCTCGAAGATCATCAAGGATTGCCTGTTCAAGCGAAGATTTCC
GATCGAGTGCTTCGATTCCGTGGAGATCTCCCGGAGTCAACGACTTACACGACTGTCTGGAAGATGCAGACTTCCCCTGGAAGATCTGACTCTGCAAGGATTTCCAAGGA
TGGATAACGAGGAGAACGAGGAATGAAGCAACTGAACTGTCGGTGCTGACTGGTCAACTGATACAGAAACTTCATGGGAACTGTCGGAGAATGGTGGTGAGAGAGACTGTACCTGCAAAACGGGAAGAG
TTCGATGAAGTGATGAAGCAACTGAACTGATGGGCAACTGATGCTGACTGAACGAAGATCGGGACTGTGGGGAGCTGACTGTGGGCAACGCCGGAAACTTCCCTGCAAATGAAGGACTGTCCAAGTGT
TATCCTGGATTTCCTGAAGGTTCCCTGCACGAGACACATCCGTAACGAGATCATCATAAAGGTCCAAGCTGATCATGAACATCGTGCAAAGTGGAGCTAGACAAATCA
CCGGACAAGGAGAACACAAGCAGGAGATCCCAAATCCAACAGAGATCCGATAAGCTGGATAACAGCTGTGGAGGATGTGAGCTGGATAACATCCGAGGATGTGAGGAGGAGAGGTGAAGCTGATCCTGAGAGCTAGACAAGGCTAAGGCT
GTGATGGGAAGACACAAGCCAGGAAACATCGTGATCGAAGGAGAAGATCCAAATCCAACAGAGATCTCCGATAAGCTGGATAAAGGTCCAGCTGGATAACGAGGATGGTGCTGGATGTGAGACTAGATGGTGAGGAGAGGTGAAGAGCT
GGAGGGAATCAAGGAGATCCGGGAATCAAGAGCTGGATAGAGAAGACCGATAAGAAAGTTCGATAATCGGATTCCAATTCTACAAGGTGAACATGGTGAAGATTCCGAATTCGAAGTGGAAAAGAAAAGGAAGATCGGGAGACTAGACAAGGCTGATAACAACAAGGCTG
ATATGTACGTGGATCAAGAGCTGGATAAGAGCTGGATAGAGAAGACCGATAAGAAAGTTCGATAATCGGATTCCAATTCTACAAGGTGAACATGGTGAAGCTGATCAGAGAGGTGATCAACTGGAAACAACTGGTGTGAGACTAGACAAATCA
CTGACTAGACGTGGATCAAGAGCTCAAGAGCTGGATAAGAGCTGGATAACAGAGGAAAGTTCGATTCGAATTCTACAATTCTACAATTCTACAAGGTGAACATGGTGCAGAGAGGTGATCAGAGAGGTGATCAACTGGAAACAACTGGTGTGAGACTAGACAAATCA
CACTCAAGAAGAAGTTCGATAATCCGGATTCCAATTCTACAAGGTGAACATGGTGAAGCTGATCAGAGAGGTGATCAACTGGAAACAACTGGTGTGAGACTAGACAAATCA
CTAAGCACGTGGCTCAAATCCGGATTCCAATTCTACAAGGTGAGAATGAACGAGCTGATAATGAAGGTGAAGCTGATCAGAGAGGTGATCACCGATGATCACGAGCGTCTTACCTGGTGGAACGTCTTGGTGCAAGTCCAAGCTGGTG
TCCGATTTCAGAAAGGATTCCAATTCCAATTCTACAAGGTGAGATTACAAGGTGTACGAGATTACAAGGTGTACGATGTGAGAAGATGATCGCTGAGCAAGATGATCGCTGAGCAAGATGAGAAGATCGGAAGGTCGAAGGCTGGAACTGCTCTGATCAA
GAACTACCCAAAGCTGAGTCGGAGTTCGTGTACGAGATTACAAGGTGTACGAGATTACAAGGTGTACGATTGAACTCCTCAAGGATCAGGATCAGGTCCTGCCTAAGCTCGAGGCAAGAATCGGAGACTAACGGAGAGAGCTGGA
AGTACTCTTCTACTCCAACATCATGAAGAGATTTCCGCTACTGTGAGAGTAAGCTGTGTCCATGCCTACTCTGAAGACTGAAGAATTCGCTGAAGATCGAGTGGCAAGATCAAACTAACGGAGAGCTGCAAACTGGAGGATTCTC
GAGATCGTGTGGGATAAGGGACAGAGATTTCCGCTACTGTGAAGAAGCTGTGCCATGCCTACTCTGAAGAATCGTGAAGAAGATCGTGAAGATCGAGAAGATCGTGAAGACTGAAGACTGAAGACTCGTGAAACTGGAGGATTCTC
CAAGGAGTCCATCCTGCCAAAGGGAAAACTCCCGATAAGGTGAAGGGAAAACGAGGATTCGGTGAAGATCCGTGAAGAAGCTGATCATGGGAGATCTGAACTGTTCCAAGCTGGCTTACT
CCGTTGCTGGTGGCTAAGGTGGCTAAGGTGCTGAAGGTCCAAAAGAGAAACGAGCTGGCTCTGCCATCTCCGTGAACTTCATGGGAGCTGTGAACCGAGAAGCTGGTCCCAACCTGGTCTTCGAGAAGATCGAGAAGAGAAT
CCAATCGATTTCCGCTGGTGGCTAAGGTGCTGAAGTCCGTGGAAGTTCGGTGAGGAAGCTGGCTAAGGTCCAAGAGATGAGGAAGTTCGATCATCCCCGATTCCAGGCTTCCCACTACGGAAGCTGAAGGATCCC
GCTAACGTTCCGCTGCTGTTCGGTAAGGGCGAATAAGACAACTGTTCGTCCGCTTACAACAGCAACTGATAGAACAAGCACTACACTTCTCCAAGCTGATCTGAGCTGAAGACTGGCTGAT
GCTAACCTGGATAAGGTGCTGTCCGCTTACAACAAGCACCGAGCTGATAAGAAACTAAGAAGAGTTCTCCAAGCTGATCTGAGCTGAAGACTGGCTGAT
TCCAGCTGCTTTCAAGTACGTCTGCCAACTGTCCCAACTGGGAGGAGATCGTGATCTGATACTATCTGATGAAGATCCAAGATATAAGAATTAAGAGAAAGGAAAGATGGTGGGAGGAATGA
ACGAGACTAGAATCGATCTGTCCCAACTGGGAGGAGATCTGCAACAAGAAAGATGGCAACAATCCATCACTCCATCACTGGACTGT (SEQ ID NO:1)
```

FIG. 5

Full-length Amino Acid Sequence of GmCas9 nuclease (1379aa including 11aa mNLS)

MDKKYSIGLDIGTNSVGWAVITDEYKVPSKKFKVLGNTDRHSIKKNLIGALLFDSGETAEAATRLKRTARRRYTRRKNRICYLQEIFSNEMA
KVDDSFFHRLEESFLVEEDKKHERHPIFGNIVDEVAYHEKYPTIYHLRKKLVDSTDKADLRLIYLALAHMIKFRGHFLIEGDLNPDNSDVD
KLFIQLVQTYNQLFEENPINASGVDAKAILSARLSKSRRLENLIAQLPGEKKNGLFGNLIALSLGLTPNFKSNFDLAEDAKLQLSKDTYDD
DLDNLLAQIGDQYADIFLAAKNLSDAILLSDILRVNTEITKAPLSASMIKRYDEHHQDLTLLKALVRQQLPEKYKEIFFDQSKNGYAGYID
GGASQEEFYKFIKPILEKMDGTEELLVKLNREDLLRKQRTFDNGSIPHQIHLGELHAILRRQEDFYPFLKDNREKIEKILTFRIPYYVGPL
ARGNSRFAWMTRKSEETITPWNFEEVVDKGASAQSFIERMTNFDKNLPNEKVLPKHSLLYEYFTVYNELTKVKYVTEGMRKPAFLSGEQKK
AIVDLLFKTNRKVTVKQLKEDYFKKIECEDSVEISGVEDRFNASLGTYHDLLKIIKDKDFLDNEENEDILEDIVLTLTLFEDREMIEERLK
TYAHLFDDKVMKQLKRRRYTGNGRLSRKLINGIRDKQSGKTILDFLKSDGFANRNFMQLIHDDSLTFKEDIQKAQVSGQGDSLHEHIANLA
GSPAIKKGILQTVKVVDELVKVMGRHKPENIVIEMARENQTTQKGQKNSRERMKRIEEGIKELGSQILKEHPVENTQLQNEKLYLYLQNG
RDMYVDQELDINRLSDYDVDHIVPQSFLKDDSIDNKVLTRSDKNRGKSDNVPSEEVVKKMKNYWRQLLNAKLITQRKFDNLTKAERGGLSE
LDKAGFIKRQLVETRQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRPLIETNGETGEIVWDKGRDFATVRKVLSMPQV
NIVKKTEVQTGGFSKESILPKRNSDKLIARKKDWDPKKYGGFDSPTVAYSVLVVAKVEKGKSKKLKSVKELLGITIMERSSFEKNPIDFLE
AKGYKEVKKDLIIKLPKYSLFELENGRKKRMLASAGELQKGNELALPSKYVNFLYLASHYEKLKGSPEDNEQKQLFVEQHKHYLDEIIEQIS
EFSKRVILADANLDKVLSAYNKHRDKPIREQAENIIHLFTLTNLGAPAAFKYFDTTIDRKRYTSTKEVLDATLIHQSITGLYETRIDLSQL
GGDLQPKKKRKVGG (SEQ ID NO:2)

Modified NLS in Arabidopsis (for C-terminal NLS)
CTGCAACCAAAGAAGAAGAGAAAGAAAGGTGGGAGGATGA (SEQ ID NO:3)
 L   Q   P   K   K   K   R   K   V   G   G   *  (SEQ ID NO:4)

FIG. 6 cggtgaattcAAGCTTTCGTTGAACAACGGAAACTCGACTTGCCTTCCGCACAATACATCATTTCTTCTTAGCTTTTTTCTTCTTCTTCGTTCAT
ACAGTTTTTTTTGTTTATCAGCTTACATTTCTTGAACCGTAGCTTTCGTTTCTTTTTAACTTTCCATTCGGAGTTTTTGTATCTTGTTTC
ATAGTTTGTCCCAGGATTAGAATGATTAGCCATCGAACCTTCAAGAATTTGATTGAATAAAACATCTTCATTCTTAAGATATGAAGATAATCTTCA
AAAGGCCCCTGGGAATCTGAAAGAAGAGCAGGCCCATTTATATGGGAAAGAACAATAGTATTTCTTATATAGGCCCATTTAAGTTGAAAACAA
TCTTCAAAAGTCCCACATCGCTTAGATAAGAAAACGAAGCTGAGTTTATATACAGCTAGAGTCGAAGTAGTGATTGggtcttcgagaagacctGTT
TTAGAGCTAGAAATAGCAAGTTAAAATAAGGCTAGTCCGTTATCAACTTGAAAAAGTGGCACCGAGTCGGTGCTTTTTTTgaattcagcc (SEQ ID NO:5)

SEQUENCE LISTING

```
<160> NUMBER OF SEQ ID NOS: 49

<210> SEQ ID NO 1
<211> LENGTH: 4140
<212> TYPE: DNA
<213> ORGANISM: Artificial Sequence
<220> FEATURE:
<223> OTHER INFORMATION: synthetic

<400> SEQUENCE: 1
atggataaga agtactccat cggactggat atcggaacta actccgtggg atgggctgtg      60
atcactgatg agtacaaggt gccatccaag aagttcaagg tgctgggaaa cactgataga     120
cactccatca agaagaacct gatcggagct ctgctgttcg attccggaga gactgctgag     180
gctactagac tgaagagaac tgctagaaga agatacacta gaagaaagaa cagaatctgc     240
tacctgcaag agatcttctc caacgagatg gctaaggtgg atgattcctt cttccacaga     300
ctggaggagt ccttcctggt ggaggaggat aagaagcacg agagacaccc aatcttcgga     360
aacatcgtgg atgaggtggc ttaccacgag aagtacccaa ctatctacca cctgagaaag     420
aagctggtgg attccactga taaggctgat ctgagactga tctacctggc tctggctcac     480
atgatcaagt tcagaggaca cttcctgatc gagggagatc tgaacccaga taactccgat     540
gtggataagc tgttcatcca actggtgcaa acttacaacc aactgttcga ggagaaccca     600
atcaacgctt ccgagtggga tgctaaggct atcctgtccg ctagactgtc caagtccaga     660
agactggaga acctgatcgc tcaactgcca ggagagaaga gaacggact gttcggaaac     720 ctgatcgctc tgtccctggg actgactcca aacttcaagt ccaacttcga tctggctgag     780
gatgctaagc tgcaactgtc caaggatact tacgatgatg atctggataa cctgctggct     840
caaatcggag atcaatacgc tgatctgttc ctggctgcta gaacctgtc cgatgctatc     900 ctgctgtccg atatcctgag agtgaacact gagatcacta aggctccact gtccgcttcc     960
atgatcaaga gatacgatga gcaccaccaa gatctgactc tgctgaaggc tctggtgaga    1020
caacaactgc cagagaagta caaggagatc ttcttcgatc aatccaagaa cggatacgct    1080
ggatacatcg atggaggagc ttcccaagag gagttctaca gttcatcaa gccaatcctg    1140 gagaagatgg atggaactga ggagctgctg gtgaagctga acagagagga tctgctgaga    1200
aagcaaagaa ctttcgataa cggatccatc ccacaccaaa tccacctggg agagctgcac    1260
```

```
gctatcctga agaacaaga ggatttctac ccattcctga aggataacag agagaagatc      1320
gagaagatcc tgactttcag aatcccatac tacgtgggac cactggctag aggaaactcc      1380
agattcgctt ggatgactag aaagtccgag gagactatca ctccatggaa cttcgaggag      1440
gtggtggata agggagcttc cgctcaatcc ttcatcgaga aatgactaa cttcgataag      1500 aacctgccaa acgagaaggt gctgccaaag cactccctgc tgtacgagta cttcactgtg      1560
tacaacgagc tgactaaggt gaagtacgtg actgagggaa tgagaaagcc agctttcctg      1620
tccggagagc aaaagaaggc tatcgtggat ctgctgttca agactaacag aaaggtgact      1680
gtgaagcaac tgaaggagga ttacttcaag aagatcgagt gcttcgattc cgtggagatc      1740
tccggagtgg aggatagatt caacgcttcc ctgggaactt accacgatct gctgaagatc      1800
atcaaggata aggatttcct ggataacag gagaacgagg atatcctgga ggatatcgtg      1860
ctgactctga ctctgttcga ggatagagag atgatcgagg agagactgaa gacttacgct      1920
cacctgttcg atgataaggt gatgaagcaa ctgaagagaa aagatacac tggatgggga      1980 agactgtcca gaaagctgat caacggaatc agagataagc aatccggaaa gactatcctg      2040
gatttcctga gtccgatgg attcgctaac agaaacttca tgcaactgat ccacgatgat      2100
tccctgactt tcaaggagga tatccaaaag gctcaagtgt ccggacaagg agattccctg      2160
cacgagcaca tcgctaacct ggctggatcc ccagctatca agaagggaat cctgcaaact      2220
gtgaaggtgg tggatgagct ggtgaaggtg atgggaagac acaagccaga gaacatcgtg      2280
atcgagatgg ctagagagaa ccaaactact caaaagggac aaaagaactc cagagagaga      2340
atgaagagaa tcgaggaggg aatcaaggag ctggatccc aaatcctgaa ggagcaccca      2400
gtggagaaca ctcaactgca aaacgagaag ctgtacctgt actacctgca aaacggaaga      2460
gatatgtacg tggatcaaga gctggatatc aacagactgt ccgattacga gtgggatcac      2520
atcgtgccac aatccttcct gaaggatgat tccatcgata caaggtgct gactagatcc      2580 gataagaaca gaggaaagtc cgataacgtg ccatccgagg aggtggtgaa gaagatgaag      2640
aactactgga gacaactgct gaacgctaag ctgatcactc aaagaaagtt cgataacctg      2700
actaaggctg agagaggagg actgtccgag ctggataagg ctggattcat caagagacaa      2760
ctggtggaga ctagacaaat cactaagcac gtggctcaaa tcctggattc cagaatgaac      2820
actaagtacg atgagaacga taagctgatc agagaggtga aggtgatcac tctgaagtcc      2880
aagctggtgt ccgatttcag aaaggatttc caattctaca aggtgagaga gatcaacaac      2940
taccaccacg ctcacgatgc ttacctgaac gctgtggtgg aactgctctc gatcaagaag      3000
tacccaaagc tggagtccga gttcgtgtac ggagattaca aggtgtacga tgtgagaaag      3060
atgatcgcta gtccgagca agagatcgga aaggctactg ctaagtactt cttctactcc      3120
aacatcatga acttcttcaa gactgagatc actctggcta acggagagat cagaaagaga      3180
ccactgatcg agactaacgg agagactgga gagatcgtgt gggataaggg aagagatttc      3240
gctactgtga gaaggtgct gtccatgcca caagtgaaca tcgtgaagaa gactgaggtg      3300
caaactggag gattctccaa ggagtccatc ctgccaaaga gaaactccga taagctgatc      3360
gctagaaaga aggattggga tccaaagaag tacgaggat cgattcccc aactgtggct      3420 tactccgtgc tggtggtggc taaggtggag aagggaaagt ccaagaagct gaagtccgtg      3480
aaggagctgc tgggaatcac tatcatggag agatcctcct tcgagaagaa cccaatcgat      3540
ttcctggagg ctaagggata caaggaggtg aagaaggatc tgatcatcaa gctgccaaag      3600
tactccctgt tcgagctgga gaacggaaga aagagaatgc tggcttccgc tggagagctg      3660
```

```
caaaagggaa acgagctggc tctgccatcc aagtacgtga acttcctgta cctggcttcc    3720
cactacgaga agctgaaggg atccccagag gataacgagc aaaagcaact gttcgtggag    3780
caacacaagc actacctgga tgagatcatc gagcaaatct ccgagttctc caagagagtg    3840
atcctggctg atgctaacct ggataaggtg ctgtccgctt acaacaagca cagagataag    3900
ccaatcagag agcaagctga gaacatcatc cacctgttca ctctgactaa cctgggagct    3960
ccagctgctt tcaagtactt cgatactact atcgatagaa agagatacac ttccactaag    4020
gaggtgctgg atgctactct gatccaccaa tccatcactg gactgtacga gactagaatc    4080
gatctgtccc aactgggagg agatctgcaa ccaaagaaga agagaaaggt gggaggatga    4140
```

<210> SEQ ID NO 2
<211> LENGTH: 1379
<212> TYPE: PRT
<213> ORGANISM: Artificial Sequence
<220> FEATURE:
<223> OTHER INFORMATION: synthetic

<400> SEQUENCE: 2

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
```

```
                275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
        450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
    690                 695                 700
```

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110
```

-continued

```
Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Leu Gln Pro Lys Lys Lys Arg Lys Val Gly Gly
    1370                1375

<210> SEQ ID NO 3
<211> LENGTH: 36
<212> TYPE: DNA
<213> ORGANISM: Artificial Sequence
<220> FEATURE:
<223> OTHER INFORMATION: synthetic

<400> SEQUENCE: 3
ctgcaaccaa agaagaagag aaaggtggga ggatga                            36

<210> SEQ ID NO 4
<211> LENGTH: 11
<212> TYPE: PRT
<213> ORGANISM: Artificial Sequence
<220> FEATURE:
<223> OTHER INFORMATION: synthetic

<400> SEQUENCE: 4

Leu Gln Pro Lys Lys Lys Arg Lys Val Gly Gly
1               5                   10
```

<210> SEQ ID NO 5
<211> LENGTH: 571
<212> TYPE: DNA
<213> ORGANISM: Artificial Sequence
<220> FEATURE:
<223> OTHER INFORMATION: synthetic

<400> SEQUENCE: 5

```
cggtgaattc aagctttcgt tgaacaacgg aaactcgact tgccttccgc acaatacatc    60
atttcttctt agcttttttt cttcttcttc gttcatacag tttttttttg tttatcagct   120 tacatttttct tgaaccgtag ctttcgtttt cttcttttta actttccatt cggagttttt   180
gtatcttgtt tcatagtttg tcccaggatt agaatgatta ggcatcgaac cttcaagaat   240
ttgattgaat aaaacatctt cattcttaag atatgaagat aatcttcaaa aggcccctgg   300
gaatctgaaa gaagagaagc aggcccattt atatgggaaa gaacaatagt atttcttata   360
taggcccatt taagttgaaa acaatcttca aaagtcccac atcgcttaga taagaaaacg   420
aagctgagtt tatatacagc tagagtcgaa gtagtgattg ggtcttcgag aagacctgtt   480
ttagagctag aaatagcaag ttaaaataag gctagtccgt tatcaacttg aaaaagtggc   540
accgagtcgg tgcttttttt tgaattcagc c                                  571
```

<210> SEQ ID NO 6
<211> LENGTH: 30
<212> TYPE: DNA
<213> ORGANISM: Artificial Sequence
<220> FEATURE:
<223> OTHER INFORMATION: synthetic

<400> SEQUENCE: 6

```
ccaagcttcc caactacacg atggactcac                                     30
```

<210> SEQ ID NO 7
<211> LENGTH: 34
<212> TYPE: DNA
<213> ORGANISM: Artificial Sequence
<220> FEATURE:
<223> OTHER INFORMATION: synthetic

<400> SEQUENCE: 7

```
ccggcgcgcc atgtaaagag aagagaggac aaag                                34
```

<210> SEQ ID NO 8
<211> LENGTH: 30
<212> TYPE: DNA
<213> ORGANISM: Artificial Sequence
<220> FEATURE:
<223> OTHER INFORMATION: synthetic

<400> SEQUENCE: 8

```
ccaagcttcc caactacacg atggactcac                                     30
```

<210> SEQ ID NO 9
<211> LENGTH: 34
<212> TYPE: DNA
<213> ORGANISM: Artificial Sequence
<220> FEATURE:
<223> OTHER INFORMATION: synthetic

<400> SEQUENCE: 9

```
ccggcgcgcc atgtaaagag aagagaggac aaag                                34
```

```
<210> SEQ ID NO 10
<211> LENGTH: 34
<212> TYPE: DNA
<213> ORGANISM: Artificial Sequence
<220> FEATURE:
<223> OTHER INFORMATION: synthetic

<400> SEQUENCE: 10
cgaaaataaa tgaaggcatc aataaaagct tacc                            34

<210> SEQ ID NO 11
<211> LENGTH: 45
<212> TYPE: DNA
<213> ORGANISM: Artificial Sequence
<220> FEATURE:
<223> OTHER INFORMATION: synthetic

<400> SEQUENCE: 11
gtcagctcgg cgcgcctctt cttctcctct gcaattttc atcac                 45

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
gattgagaat caagaataca agaa                                       24

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
aaacttcttg tattcttgat tctc                                       24

<210> SEQ ID NO 14
<211> LENGTH: 24
<212> TYPE: DNA
<213> ORGANISM: Artificial Sequence
<220> FEATURE:
<223> OTHER INFORMATION: synthetic

<400> SEQUENCE: 14
gattggaaaa gttgtagact gaga                                       24

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15
aaactctcag tctacaactt ttcc                                       24

<210> SEQ ID NO 16
<211> LENGTH: 23
<212> TYPE: DNA
<213> ORGANISM: Artificial Sequence
<220> FEATURE:
<223> OTHER INFORMATION: synthetic
```

<400> SEQUENCE: 16
ggaaaagttg tagactgaga tgg                                    23

<210> SEQ ID NO 17
<211> LENGTH: 22
<212> TYPE: DNA
<213> ORGANISM: Artificial Sequence
<220> FEATURE:
<223> OTHER INFORMATION: synthetic

<400> SEQUENCE: 17
gcacgtgtca cgaaaaccca tc                                     22

<210> SEQ ID NO 18
<211> LENGTH: 24
<212> TYPE: DNA
<213> ORGANISM: Artificial Sequence
<220> FEATURE:
<223> OTHER INFORMATION: synthetic

<400> SEQUENCE: 18
attgtagtaa cataaagtta tgta                                   24

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
gattgggctc caccgccggc gacg                                   24

<210> SEQ ID NO 20
<211> LENGTH: 24
<212> TYPE: DNA
<213> ORGANISM: Artificial Sequence
<220> FEATURE:
<223> OTHER INFORMATION: synthetic

<400> SEQUENCE: 20
aaaccgtcgc cggcggtgga gccc                                   24

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
gattgaacca ggacaaggtc ctca                                   24

<210> SEQ ID NO 22
<211> LENGTH: 24
<212> TYPE: DNA
<213> ORGANISM: Artificial Sequence
<220> FEATURE:
<223> OTHER INFORMATION: synthetic

<400> SEQUENCE: 22
aaactgagga ccttgtcctg gttc                                   24

<210> SEQ ID NO 23
<211> LENGTH: 23

```
<212> TYPE: DNA
<213> ORGANISM: Artificial Sequence
<220> FEATURE:
<223> OTHER INFORMATION: synthetic

<400> SEQUENCE: 23
gggctccacc gccggcgacg tgg                                             23

<210> SEQ ID NO 24
<211> LENGTH: 21
<212> TYPE: DNA
<213> ORGANISM: Artificial Sequence
<220> FEATURE:
<223> OTHER INFORMATION: synthetic

<400> SEQUENCE: 24
cacggtgctt gaattagtgc g                                               21

<210> SEQ ID NO 25
<211> LENGTH: 19
<212> TYPE: DNA
<213> ORGANISM: Artificial Sequence
<220> FEATURE:
<223> OTHER INFORMATION: synthetic

<400> SEQUENCE: 25
ggtcctccat ctggcaccg                                                  19

<210> SEQ ID NO 26
<211> LENGTH: 23
<212> TYPE: DNA
<213> ORGANISM: Artificial Sequence
<220> FEATURE:
<223> OTHER INFORMATION: synthetic

<400> SEQUENCE: 26
gaaccaggac aaggtcctca tgg                                             23

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
ggtggtggac gaggaggc                                                   18

<210> SEQ ID NO 28
<211> LENGTH: 21
<212> TYPE: DNA
<213> ORGANISM: Artificial Sequence
<220> FEATURE:
<223> OTHER INFORMATION: synthetic

<400> SEQUENCE: 28
gtagcaccaa tgatgagcga g                                               21

<210> SEQ ID NO 29
<211> LENGTH: 2499
<212> TYPE: DNA
<213> ORGANISM: Zea maize

<400> SEQUENCE: 29
gtcatggatg gagccagtga actgatgatt ttttccccac cccgcacgca acagcatggg     60
```

```
tgacaacaac cactcccgct gcggttgggc gagcacatct ctacgcactt gacactcacg    120
caaacctaac gcatactaga ttaatcatcg ccaccaacta tcggcgacag aaacgatggg    180
ccccgcttct cttaatcacg gtgcttgaat tagtgcgcgc atagtagtga aaataatag    240 tgaaaaataa gcagtgcgtg ttttggtgtg gtggttggtg agccgtccgg cccaataaaa    300 accccctcgca ccacctcgtc cctcttcgtc gcatcgcacg ccatcagcag ctagcgcgct    360
cctcgagccc agcagagaaa ggccggccta cccactctct ctctctctct ctccagtctc    420
caccggcagc gctaatcgta atagccatgg gctccaccgc cggcgacgtg gccgcggtgg    480
tggacgagga ggcgtgcatg tacgcgatgc agctggcgtc gtcgtccatc ctgcccatga    540
cgctgaagaa cgccatcgag ctgggcctgc tggaggtgct gcagaaggag gccggcggcg    600
gcaaggcggc gctggcgccc gaggaggtgg tggcgcggat gccgcggcg cccggcgacc    660 ccgccgccgc ggcggccatg gtggaccgca tgctccgcct gctcgcctcc tacgacgtcg    720
tccggtgcca gatggaggac cgggacggcc ggtacgagcg ccgctactcc gccgcgcccg    780
tctgcaagtg gctcaccccc aacgaggacg gcgtgtccat ggccgccctc gcgctcatga    840
accaggacaa ggtcctcatg gagagctggt gagtagtagc cgcatcgcat caaccaccctt    900 ctacctatct atatccatca cttgttgctg ctggcgtgcg cggcatgcat gatgacgagc    960
tcgctcatca ttggtgctac tagtgattta tttcgtccag taaaattaat taaggtgcgc   1020
tgctactcta ctggctgcgg ctagcacaag gctggaaata ttgttactt gttatacacg    1080 atataatatt tctctagaac aaaaaagatt ttttttttat aaaaagcaag caagaaagaa   1140
agtgagtgac ttcatgtttt tcctaaaaaa aagttaggag tgggatggaa aagtcagcaa   1200
ggaccacttg tttgttgtcc actatccatc cagtgggtga actttttttg cgagacggag   1260
cactatatta ttggccgagt cctttttctg tatccgcaaa acggcagccg tcgatcgccg   1320
gacggatcga cggctcacat gagtgtcgag tccaattcca accacgaggg cggcaaggaa   1380
aaccatccgt gctggtctgg actttttgcc aaactccatt cagccattcg ccgactgaag   1440
gtgaatcttc agacagccag attgtttggt gtctagtgtg tgcgaagatg cgtagaaaaa   1500
gactgagaga cagttggctc acacagacaa gtgacaactg actatagtat ctgcctgcct   1560
ggctgatgct gatagagatg gggactcttg tcctgtctgt ttcttgtatg cgctgatctg   1620
attctgatca ctgccactct gccaggtact atctcaagga cgcggtgctg gacggcggca   1680
tcccgttcaa caaggcgtac gggatgacgg cgttcgagta ccacggcacg gactcgcgct   1740
tcaaccgcgt gttcaacgag ggcatgaaga accactcggt gatcatcacc aagaagctgc   1800
tggacttcta cacgggcttc gagggcgtgt cgacgctggt ggacgtgggc ggcggcgtgg   1860
gcgccacgct gcacgccatc acgtcccgcc acccgcacat ctccggggtc aacttcgacc   1920
tgccgcacgt catctccgag gcgccgccgt tccccggcgt gcgccacgtg ggcggggaca   1980
tgttcgcgtc cgtgcccgcc ggcgacgcca tcctcatgaa gtggatcctc cacgactgga   2040
gcgacgcgca ctgcgccacg ctgctcaaga actgctacga cgcgctgccg gaaaatggca   2100
aggtcatcgt cgtcgagtgc gtgctgccgg tcaacacgga ggccacccc aaggcgcagg   2160 gcgtcttcca cgtcgacatg atcatgctcg cgcacaaccc cggcggcaag gagcggtacg   2220
agcgcgagtt ccgcgagctc gcaaagggcg ccggcttctc cgggttcaag gccacctaca   2280
tctacgccaa cgcctgggcc atcgagttca tcaagtgaac caccgtcgcc gcgatgagat   2340
ggcatggctg ccacatgctt tgcttgcttg gtcctcgtat cgtacgtcgc cgtcgtcgtc   2400
ttcttctggt tattgcgctg ctacctcgct gctctcgcgt atgcatgtac ttttgcttaa   2460
```
ttttctttct tcatatcatg cactctggct ggcctagac 2499

<210> SEQ ID NO 30
<211> LENGTH: 24
<212> TYPE: DNA
<213> ORGANISM: Artificial Sequence
<220> FEATURE:
<223> OTHER INFORMATION: synthetic

<400> SEQUENCE: 30
gattgccgct agggcatctt agat 24

<210> SEQ ID NO 31
<211> LENGTH: 24
<212> TYPE: DNA
<213> ORGANISM: Artificial Sequence
<220> FEATURE:
<223> OTHER INFORMATION: synthetic

<400> SEQUENCE: 31
aaacatctaa gatgccctag cggc 24

<210> SEQ ID NO 32
<211> LENGTH: 23
<212> TYPE: DNA
<213> ORGANISM: Artificial Sequence
<220> FEATURE:
<223> OTHER INFORMATION: synthetic

<400> SEQUENCE: 32
gccgctaggg catcttagat agg 23

<210> SEQ ID NO 33
<211> LENGTH: 23
<212> TYPE: DNA
<213> ORGANISM: Artificial Sequence
<220> FEATURE:
<223> OTHER INFORMATION: synthetic

<400> SEQUENCE: 33
tgtgcattct ttccaaaagg tca 23

<210> SEQ ID NO 34
<211> LENGTH: 22
<212> TYPE: DNA
<213> ORGANISM: Artificial Sequence
<220> FEATURE:
<223> OTHER INFORMATION: synthetic

<400> SEQUENCE: 34
gctccaaagg gctttagtag ga 22

<210> SEQ ID NO 35
<211> LENGTH: 10581
<212> TYPE: DNA
<213> ORGANISM: Triticum turgidum

<400> SEQUENCE: 35
atgactacac caatgagtat accgttcgca actttggaaa agattacaaa tgggttctca 60
aacgatttaa taattggaag gggtgggtat ggaaacgttt acaaggtatg gcttaatact 120
tgatatttcc ttttttcagc aaatgttcag gctataaaca aataatttaa gtgcaataat 180
tatgtcaagc aggcagttta caaggggaa gtgattgctg tgaagttgct tcatgatgat 240

```
ctggtgcaat tacttgatga cagacaattt aaaaatgaac tttttaacct tttgagggtt      300
gagcatccga atattgtttg cttacgtggt tattgttatg aaacacggta taaaattgtt      360
aagcacaatg gtgagacagt ctttggtaaa catatacaca gagttctctg ctttgaatac      420
ttggagggtg gaagcctaga caatcatctt catggtacga tggaacttca aaatacagtt      480
attttgtttt acgtttaaag gaaactgatt tctcatttac atacatactc tttgttaact      540
tgcgtagcac catctttgcc acctaactgg accacacgtt acaataccat aaaggggatt      600
tgtgaaggct taaatttcct tcacggatgt caaccaccaa ttttgcatct tgatctgaag      660
cctgccaata tattagtaga cagttccatg gtgcctaaac tggcggattt tggattgtca      720
aagctcttcc atggatcaca tactcatgtg acaaaacaaa tcataggaac ccagtaagcg      780
gaagcgaccc gtggattgtc tcgttctgaa ttttctttct tttgtgatca aataaatagt      840
atgtacagtt ctgtactaac tgtgtctttg tatcacgcag gaagtacatg ccaccggaat      900
tcatcaaaga tggcaagatc tcggttaaaa atgatgtctt tagtttgggt attgtgatca      960
tagaaataat ggcaggacct atgggttatt cagaattttc agaaatgggc agcggtgcac     1020
aatttgtgaa ggaggtaata aaaaaaactc aagtttgaca cccgagttcg tataaataac     1080
aaactaccac accaagaatt tgatgtctaa tgtgtgagcc attataatcg ttgaactgag     1140
tttatgacag gaccggcagt aataaaaaat atagcaacac tcccccacac aatatattga     1200
gcatagaaga tacaacttat ctagctataa caaaataata atccagaaaa gtagccattt     1260 tttttttccgg acaggattga ggtccaccag tccataaact atgaagcagc tcgctgatag     1320
aaaattccaa ggtacaatta tttttgtaag tttctcctta tcacgtgtga aacaccaatg     1380
taataaagct gataaaccaa acgtacccac tatgagaact gcatacactg agactcgaag     1440
aaaagaacaa atgcatatct agaaccttgc tccatgggat atctagaacc ttgctccatg     1500
ggatctagca ccatctccat tttggagcaa gcacgaggtg cgtatcgtaa tcttttttctg     1560 ctagatgcag acttagacac ccagtattct ctaggtaaat tatttatctg gaaagtcgta     1620
ggtaacactt gtgaacaagg atatagcgta catatatatg ggagcatttg tgttatgtga     1680
cacttttgac ttaattgcaa atattatgtt atgtgaagac tcaagagtgt ttttgaacaa     1740
gtatcgtaca tattgtaccg aaaaaggctt tcgccccgct ttatattata aagcacatgc     1800
ccaagccaac aaaccacaca ggttcacaaa cacacgcaga cccacacaca ccaagttcac     1860
acacagacaa gatccacaag ggttaatgct gagggcacag cttaacaagc cctagaacaa     1920
aaaggaaaga caccatctag tcgggctccg gggggggggg ggggggggggc ggcggaagtg     1980 gaggcgccag gcggaaggcg agcgatcgaa ggtcggcgag gagggtgttg atgatgtccc     2040
gatcctgagg gcggctaagc ggccgccaaa gctgcaagta cccacacatt ttaaaaatgg     2100
cgtcagtagc gcgtcgtaga gggactttttt ggatgacaag cttattgcgg acggtccaca     2160
gcgtccagcc gagaaccca acgcataacc aacggatatg tcggtggcgt ggggggggag      2220
gcgtggattt ccgcgaggag gtcggggaag ttggagttgc accactatcc gccaaccgtc     2280
tcacggaaac tggaccaaag aaactggccg cagggcacgt gaagaagatg tggttagcat     2340
cctccgcagt gccgcacaag gggcaaagcc catccccggg tccgttgcgc ttgaggactt     2400
cgacaccgga ggggaggcgg ccacgaatcc actgccaaag gaagatccta atcttcagag     2460
gtaagcgaat gtcccagatc agagcaaagg gctcgggcgc gggcgaaggc gcaatagccg     2520
cgtacatgac ctagtagaga aacgaccgga ggactctagg cgccacgaga tggcgtccgg     2580
ggcgtcggtg acgctcatcg gaagaagggc gatgtcctgg aggagggaat cccaggcggc     2640
```

-continued

```
cacttcgggg ggaccgaaag gacgacgaaa cgcgaggcgc cctaagtcaa taagggccgt    2700
ctcgacagag acccgagggt caaccgcaat ggtgaagaga tcgggaaagc gggcggccag    2760
aggggtgtca ccgagccacc gatcaaacca gaacagggtc gcggacccag taccaatcga    2820 aatgacgtg ccgatacgaa gcacaggaag cagccgcacg acggcctgcc aaaactgtga     2880
tccgcccgaa cgctgacaga aagccagagg ctggccacgg aggtatttgt tgcggataat    2940
ggtgagccac aaccctccgt caccattggc aatacgccac aaccaccggg tcaggagggc    3000
gatgttcatt cggcgggagg acagaatctc aagacccccc tggtctttag gtttacaaat    3060
gtccggccaa gtcaccatgt ggtacttctg tttgtcatcg tcgccagccc aatagaacct    3120
ggattggtac ttggcaattt ccgtgtgcag cgtttcatgg aggctataaa agctcatgag    3180
gaaccaaagg agactggcga gtgaggagtt gatgaggatc acccgcgccg cctttgatag    3240
ccaacgccct ttccaaggtt cgacgcggtg ttgcatacgg gtcaccgtag ggtggaggtc    3300
cgccacggtg aggcgcgagt cactaacggg gatccccagg taggtcgtgg ggaaggaccc    3360
tagccgacag ttcaggcgat cagcaatatc ctgagcctcc tccggagggt atccaaggac    3420
catcacctcg ctcttatcaa agttaatcgt aaggcccgac atctgctgga agcacaggag    3480
gaggaacttc aggttagcaa catcctgatt tgaaccttcc accattatta tggtgtcgtt    3540
cgcgtattgc aggagggaga cccctccccc tccaactagg tgaggacaa tgccgtggat     3600 atggccagca cccttagcct tatccaggat ggcggccaga gcatcgacca ccatgttgaa    3660
caggaacggc gagaatgggt ctcctgacag accccacaga gggtggggaa gtatggccca    3720
atctcgccgt taatgttcac cgccgtcttt ccacatgaaa ctgattgcat cacgcgggtc    3780
acccagcggt catcaaagcc cttacgcagc agtacttccc gaaggaaggg ccagtgaaca    3840
gtatcatagg ctttatggaa gtcaagcttc aggaacacag cacgaagatg cttcacccgg    3900
acctcgtgaa ggacttcatg gaataccaac acgccatcaa gaataaaccg gccttggatg    3960
aaggccgatt ggttcgggtg agtgatcgaa tcagccagca gggtcaccct attggcgtac    4020
cctttggcca ggatccgaaa aatcacgtta atcaccgtga tggggcggaa ctggcgaata    4080
tcagaggcac ccggaacctt tgggatgagg gtaatgatcc catagttgag gcgtcccagg    4140
tccatcgaac ccgaatagaa ctcctcgaac aaagccatga cctccggttt gaccgcctgc    4200
cagaatgttt taaagaaagc aacaggcagg ccatccgggc ctggggccga ggcggggttc    4260
atgcctttaa tggccgcgag cacctcgtcc tcggcgaagg gagcaaccag ggccgcattg    4320
gcctcgccgg gaaccaactg cgccccgtc caagtatcgg gggcatcgta catattgtta     4380
tatgctccat ctctaattgt atctctatat ttcggttttg taggtactta ccaattggag    4440
tactatcatt aaagctacat cagagtatcc agcagaggaa ctacatcaag tgaatttgtg    4500
catcgacata gcaatgcttt gtgtggattc tgaaagagtc aatagaccca ccatagctgg    4560
tatcctagat gcattgaata ggacaaaaac tcatatgccc tcctctacga aaaaaactca    4620
tattccctgg ggacaggtat gatttgcata cttgcaaaca aaatgaaatc tcgagtatat    4680
atttgcaatc tgtagaagac agttgcttgg atatatggac cactaagtag ttatagagtt    4740
tgcagctccc cgtctcccac tcattttatt ctcaatcaag tagttcttta atagtcagga    4800
acttgcttac tgcatccttt tgactccctg ctctataatc catgtagaag aaccttcatt    4860
ttagttccgg ctaattccag gaatagaaaa ctagagaggg cctattcgta atcgtgcctt    4920
ccggagtgac aggctaagtg aagggcaggg ggatgctgcc ctcgacaacc gtggctgtga    4980
```

-continued

```
ttggcactgt cgtgctcata cgaggtacca gacggtgtag aagttaacct agttgattaa    5040
tcttaggtgt ggtcatgcta gatagctata tgaaagagcc atacatgtag ttcaagtagt    5100
gcatgcaaga ttccaacatt caaaatcgtg ccttgtacta tggaagggga aagggagggg    5160
taacacgtaa tgagtgccct ataagcctta cacaatagct ttatcagacc actgtggcgc    5220
cctaactgac gccaacagag gtagctgcaa tggttcgatg agatagcggt gagagagaag    5280 gggcagggg acattggtgg caggtgtaag ggaaaaaggg agaggagtga agccggctgg    5340
gtaccttggt gggggagagg aaagggtgga ggaagaacaa agaggtgagg cgcctgctag    5400
tgattgcact gtaagcctac cgcgcgacat tgctccaaag ctacgctctc ccaataaagg    5460
agaacttcta gagagttgat atgaattaaa gagattacca cagactcaca tagtgcctga    5520
ggtattagcc acatttcctt tcatgccctt gccgaggggc tttcctcggc gcctctcact    5580
ttgggctttg cttcttcaaa ggtggtgttt aggccgcaaa gagtacaacc agtgtgttat    5640
gtgtgtgcac tttcggtgtg ttacaatttg ccattattgc ttgatgcttt attactattc    5700
aaaatagttt ctcttttttcc aagttgtcat tttaacatag cattatagat tttgtccttc    5760
cgatttgcat gttttgatcg tctataactt agtttacata atggaagcac atcccagaga    5820
gtaaattgat catgagatct tgaccatgat gattctcctg ttttttttcct tgtacttaca    5880 cataaaagtt gtttcagttg aagatgtgc ccctgtgttc gacaattggt cccaaaagta    5940
cgagtaaaag gtcgaaccca gttcccacaa aggaaaataa aaggttgaag atgatgacaa    6000
ctgaagtgga caatatcgcg aacaaacacc aacagtttaa ttgcatgcca ggagatagct    6060
ctaaaactat tgttcagcaa gttccagaca gggaaacatc atcagatgtg gaaccgacat    6120
taatcattgg aagggatgaa gaaaaacata aatattgtc cattttatct gagagcaacg    6180
cagaagagat gaccatcctt ccaatatatg gcatcggagg aattggcaag acaaccttgg    6240
cacaattggt gttcaatgac atacagttcc gggactacta tcgggtgtgg gtatatgttt    6300
ctcagaagtt tgacttaaag aaaattggca acttttataat atcacagtta acaaaagaga    6360
ccagcgatat agatgaccag cagacacttc ataatcgcct tagacagcta tttgctggta    6420
agagtatcct tattgttta gatgacctgt gggaggagaa acaacatgag ttagagaaat    6480
tgaaggctat gctaaggctt ggcataggaa acaaggttgt catagtaact acacgtgatg    6540
aagccattgc aaggaaaatc aacaggactg ttatgccata caagctagag attttaacag    6600
atgatatgtg ctggtctata taaaacaaa aaagtttctt tgaagatcga tgtgacaaag    6660
aacaattggg gcagatcgga atggacattg caatcaagtg tggaggtgtg ctttggcgg    6720 ctcaatcact tgggtacatg ttgagggaga tggagtctga ccaatgggag tcagtgaggg    6780
acagttatat ctggaatcta tctactatgg aagatccatc attaagaaat catgaagtgc    6840
ttctgtcctt gctgttaagc tattcccata tgcatgaatt cttgcagtta tgcttttcct    6900
attgtgcatt ctttccaaaa ggtcaaaata tagtgaagta tgatctaatt caccagtgga    6960
tagctcttgg attcaccggt ccatctggaa tatttgattc tattcagctc tgtgagaaat    7020
atattacacg gcttttgggg atgtcattcc ttcaatattc aaagacacgt cggtgagtt    7080 actacatact ctcgatgtcc caaaagatag ctatgggtag tttcttcatg tcaaagagtc    7140
cccttccagt actgctaggt gtcaggtttc tagaaggccg ctagggcatc ttagatagg    7200 tcatagttat acactactca tcctcaaatg catatgcctg tgcaattttc ttttctagat    7260
gaccttctcg acaagctcgt tgacattat cctttttctt tttctttttct ttcccttgtt    7320 ttcaacctta cctttcaaat ttccttttcc aagaatgaca ttcaagtcca taacctgatc    7380
```

```
gtggatatgg gtcctactaa agcccttTgg agctcaatat ttttcaacta tttcattaaa    7440
atgaattcac atctataatc atcatttctt ttgttatgta tgtatataaa acaatactaa    7500
ttattgttga actaataaac acatcgttga ttacctctaa acaaatttga atgtcattaa    7560
atttgtcttc atattTttta gtgggataag accccaatcc aacaggcgcc caaacaaatg    7620
gacctatgta ctgaaacgtt gctgttgctg gtgcatttgt agtgctgggt attaatttta    7680
gcaggtttaa gatgaaaacc actgcagata tttatcccag gcattattTc attTgatata    7740
agctttgaag tttacagatc catagtgtaa tctactctgg tgtaatttaa atatactgat    7800
ccgttgccca ttatcgagaa acatacagc tacggttaca ctcttttata gtgatacaaa     7860
agtatttctg ttgataaaat atactactat aaaacaaaat aaattcaata ttctaacaac    7920
attacgtggt tttgctgcag agtgatgaac ggcaggacaa agatgttaaa atgtttgtaa    7980
tgcatgacct agtgcacgat cttgcaagag caatattggc tgataaagtt aataaagagg    8040
gtgatgctgt gggaagcagt tgtcactatg cattgctcac agattgtagc aagccattgc    8100
agttgtctgt tagttcaact gaatatagcc ggttcaattt ttttcttagc ctgtttaaaa    8160
agaagagttc acatgaaaat ataaaggcgt tacgttttct gaactgtggc aaagtactac    8220
ttcgcggtga tgcattttca cctgccaagt tcctccttgt cttagatcta agtgaatgct    8280
ttattcagaa gctctcactt gattcgattg acaactgag gcacttgaga tatctttgtg     8340
ctccacgggt caacgattac acgattccca actgtatcac caagctctca gaattaactt    8400
acctcaacct tagaggctct tgtcgtatct cagcattgcc agagtcaatt ggcgatatga    8460
aaagtctgat gcatcttgat ttatcaggct gctgtgacat aattgaactc ccagtatcat    8520
ttgcgaagct gaaacagttg gtgcatctag atttatcaca ctgtcacgtg tctgtatcag    8580
aagattttgg tggctttacc aaacttcaat atttgaattt atcagttttg tttagttctt    8640
ccaaggggca taggagagga ctgctagagg tcattggcaa tttaaagaaa ctcaggtatc    8700
taaatctatc tcggtgcatg gaggacatag ccacatcaga aaaccaaatt ggcagtttgc    8760
ttgactctat cagtacccTt tccaaccttg agcatctgga cttgtctgag aataaacagc    8820
tttccagtat accagaaagt atgggcaacc tcaggaagct tcatacattg gacctcttag    8880
gctgctatca actagagaag cttcctgata gtatgattaa tatggttagc ctgaaggttc    8940
taaatgtggg taatttggtt acactggatg aatctgtgct ctctttgtta aatattgcct    9000
ccttgccaca ctttgtggtg catgcttcaa gtggtaaatg tagcagcaat atcacccgtc    9060
ttcaggctac aaatcctgat agactgatta tagatagact tgaaaatgtc aaatctgcag    9120
aagaggcaca taacataaaa ctgatagaga aacagaaaat tgaaaccta caatttgaat     9180
ggactgtggc tgctaggagg tttgtggatg acaaagaggt gttggaaaaa ctagtgccgc    9240
caagcagtgt cgacagtttg tgtataattg gttatagaag tgtcagcatt cctgattggc    9300
ttctgggtat tagtcagtat ctccctaatc ttgcgattat aagtctggtt aatttttcta    9360
agtgcaagaa cctaccacca ctcggtcaac taccaaactt acaatggctg actctcagca    9420
gtatggatgg tttggaggag tggaacacga catatactac tggagagcaa ggtagaaacg    9480
aactcttgtt ccctaagctt gagagattaa acatacatga ctgtgccaag ttgaggatag    9540
aaccatgtct gcctagagct ttgtatttgc gcatacgaga tagtaataat gtgctatcct    9600
cactcaatac aagagagcaa gctgagagca cgctgcccTc ggacatagca cattgtgata    9660
atatgatatc agcatgcgga aagagttcgt catacagcgg tgcttcctct tcttctccaa    9720
```

```
taactgatct gtttgtagag gaaagcaaac taccttgca tcagtggagg ttgcttcacc      9780
aactccccgc gctccgtggt ttacggatca acattgcag tgatctgacc acctcacttg      9840
ctgttatcca aaaactctcc tccctccaaa atttgagcct ggagctcaac gaccatgaac    9900
tgccgagttg gttgattcag ctgacagatc tacaggaatt aaagcttatg cattgcaata    9960
gcattacatc actaccacag tggtttggag aacttgcatc tctcaagaga attgagatca   10020
agtactgcaa ggggatcagc tctttgccgg agagcataca acaactgact aagcttgaat   10080
ttctaagcat tcatggctgt cctgtattag aggagtggtg tgaatcagag gagaacaaga   10140
tgaagctcac tcacatcaaa gttgaggtat gtgcgtgcaa gttatctgtt gtattgcttt    10200
tattctcgtg ctggtagtga cttaatactc ttttcttaaa tggcaagtat acacatgcca   10260
tgagtatctt tacataatca tggtaagtgt tgaattaggt gtatgtattt tgtctattag   10320
atgcttcatg tgtctagatt acttgacaaa aatatgtgac gactgcatta ataattcgcc   10380
taagaagaaa agcattccag ttgtgattgt gctatatcat gcacctatac atgcattgtt   10440
ctgattatat atcccgtttg cattgttcag atcgctggac gggattcggt aggctttgag   10500
gattcgaagg ttcagattgt caaaccaatg ccagcacaaa tggttcgcca atcagcattt    10560
gctactacag aacgaagata g                                                              10581
```

<210> SEQ ID NO 36
<211> LENGTH: 24
<212> TYPE: DNA
<213> ORGANISM: Artificial Sequence
<220> FEATURE:
<223> OTHER INFORMATION: synthetic

<400> SEQUENCE: 36
gattgggtgc cggtggcagg atga                                                                24

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
aaactcatcc tgccaccggc accc                                                                24

<210> SEQ ID NO 38
<211> LENGTH: 23
<212> TYPE: DNA
<213> ORGANISM: Artificial Sequence
<220> FEATURE:
<223> OTHER INFORMATION: synthetic

<400> SEQUENCE: 38
gggtgccggt ggcaggatga cgg                                                                  23

<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
ttcgtcccgt caacaagagg                                                                          20

```
<210> SEQ ID NO 40
<211> LENGTH: 19
<212> TYPE: DNA
<213> ORGANISM: Artificial Sequence
<220> FEATURE:
<223> OTHER INFORMATION: synthetic

<400> SEQUENCE: 40
gtccgtcggc gagcgctgg                                                    19

<210> SEQ ID NO 41
<211> LENGTH: 1553
<212> TYPE: DNA
<213> ORGANISM: Avena sativa

<400> SEQUENCE: 41
cataaaccac tcgttcgtcc cgtcaacaag aggagcagag gcgagggact cgcgctcgcg        60
tgtgtggtgt ccttccctcg atctgcccct ctccggccag ttctatcacc tcctatcagc       120
aacatgggtg ccggtggcag gatgacggag aaggagaggg agaagcagga gcagctcggc       180
cgcgccgacg tcggtgcgac cctccagcgc tcgccgacgg acaagccgcc gttcacactg       240
gggcagatca agaaggcgat cccaccccac tgcttccagc gctcggtgat caagtcattc       300
tcctacgtgg tccatgacct cgtcatcgtg gctgctctcc tgtacgccgc gctggtctgg       360
atccccaccc tcccgagcgt gctgcagctg ggcgcctggc cgctctactg gatcgtgcag       420
ggctgcgtca tgaccggcgt ctgggtcatc gcgcacgagt gcggccacca cgccttctcc       480
gactactcgc tcctcgacga catcgtcggc ctggtgctcc actcgtggct gctggtcccg       540
tacttctcgt ggaagtacag ccaccgtcgc caccactcca acaccggctc catggagcgt       600
gacgaggtgt tcgtccccaa gcagaaggac gcgctggcct ggtacacccc atacatctac       660
aacaacccca tcggccgtct ggtgcacatc gtggtgcagc tcaccctcgg gtggccgctg       720
tacctgtcga tgaacgcctc gggccgcccg tacgcgcgct tcgcctgcca cttcgacccc       780
tacggcccca tctacaacga ccgggagcgc gtccagatct tcatttcgga cgtcggtgtg       840
gtggccacgg cgttcaccct cttcaagctt gcttcggcgt tcgggttctg gtgggtggtg       900
cgcatctacg gtgtgccgct gctgatcgtg aacgcgtggc tggtcctgat cacctacctg       960
cagcacaccc accggcgct gccgcactac gactccaccg agtgggactg gctgcggggg      1020
gcgctggcca ccatggaccg ggactacggc atcctcaacc gcgtgttcca caacatcacg      1080
gacacgcacg tggcgcacca cctcttctcc accatgccgc actaccatgc catggaggcc      1140
accaaggcga tcaagccaat cctgggcgag tactaccagt cgacccac ccccgtggcc       1200 aaggcaacat ggcgcgaggc caaggagtgc atctacgtcg cgcccaccga ggaccgcaag      1260
ggcgtcttct ggtacagcaa caagttctag attcgtcatg ggacctgct gtgctgctgg      1320 aatgtgagga ggaagaagtc agtaatacac caagtatcca tccatctacc tacatatggt      1380 tggggttag tagtctttag atagaagaga gcgttgttg gcacaagga aaagactatg       1440 accaccgtgc caatgctaga agagtcgaag caggtgcaac gaggagtagc gtgtcgggtg      1500
tccgtggctt tggtcagttc cgtcctgtgt ctttacttcc tagtcgccgg ttt            1553

<210> SEQ ID NO 42
<211> LENGTH: 24
<212> TYPE: DNA
<213> ORGANISM: Artificial Sequence
<220> FEATURE:
<223> OTHER INFORMATION: synthetic
```

<400> SEQUENCE: 42
gattggcgga ggggatggtg acgg                                          24

<210> SEQ ID NO 43
<211> LENGTH: 24
<212> TYPE: DNA
<213> ORGANISM: Artificial Sequence
<220> FEATURE:
<223> OTHER INFORMATION: synthetic

<400> SEQUENCE: 43
aaacccgtca ccatcccctc cgcc                                          24

<210> SEQ ID NO 44
<211> LENGTH: 23
<212> TYPE: DNA
<213> ORGANISM: Artificial Sequence
<220> FEATURE:
<223> OTHER INFORMATION: synthetic

<400> SEQUENCE: 44
ggcggagggg atggtgacgg tgg                                           23

<210> SEQ ID NO 45
<211> LENGTH: 20
<212> TYPE: DNA
<213> ORGANISM: Artificial Sequence
<220> FEATURE:
<223> OTHER INFORMATION: synthetic

<400> SEQUENCE: 45
tccaacgtgg acacgacttt                                               20

<210> SEQ ID NO 46
<211> LENGTH: 20
<212> TYPE: DNA
<213> ORGANISM: Artificial Sequence
<220> FEATURE:
<223> OTHER INFORMATION: synthetic

<400> SEQUENCE: 46
gaggtggcat ttgtggagga                                               20

<210> SEQ ID NO 47
<211> LENGTH: 2147
<212> TYPE: DNA
<213> ORGANISM: Hordeum vulgare

<400> SEQUENCE: 47
gtcataactc ggcaaacata gattagacag aattttctga gttcttatct agaggaactc    60
gatgaacttg aggcattgtc gaggttcttc ctttcaccga gtactttttt gcgtgtacta   120
ggcaaatata tgaagtttgt gagtttcgga tcaccaccga gtgcaagttt ggaccaaact   180
tgacaaatac ataagtttgg cgagctccga atgaaatgaa ctctgcaaaa gaatagaact   240
cggcgcaaaa ccagattcta atagtgtgtg aattttgggg ctgttttgta taaatatgat   300
gaaacttagt aaaatttcac tcaggtcaat gctaatgtgg agagtaaaata aaaaatgaag   360 ggagtacttg gctgcatcat atgtttgccc ccgatcacct tcacatctcc ccgtccggac   420
ggcctggatc ggaaagcact cagccggagc cccgccggcg cttgccgttg ggtacctctg   480
ccacctattt atattacccc taggtctctc cctggagaca cgcactcccc tccttcaact   540
agtgctttgc ggcccgtggt cctcctctcg atccagttcc tgagcacacc aacaggcaac   600

```
agaacaacct accgtgtctc ccctccaatc tcctcacgat cccttctttc cctcagatcc    660
gaaccgaaag catggacaag catcagctct tgattcatc caacgtggac acgactttct     720
tcgcggccaa tggtacacac gacgccgcgc gcgcccggtc tttgcgcatg cgatgatgca    780
gctgcagtag cttcagtttc accggccagg acacgcatgt gatgacgttt tttccattct    840
gtgtttgtat gtgcaggcac ggcgcagggg gataccagca agcagagggc gcggcgcagg    900
cggcggaggt cggcgaggtg cggcggaggg gatggtgacg gtggggagat ggacggagga    960
ggggacccca agaagcggcg gctcaccgac gagcaggccg agattctgga gctgagcttc   1020
cgggaggacc gcaagctgga gacagcccgc aaggtgtatc tggccgccga gctcgggctg   1080
gaccccaagc aggtcgccgt gtggttccag aaccgccgcg cgcgccacaa gaacaagacg   1140
ctcgaggagg agttcgcgag gctcaagcac gcccacgacg ccgccatcct ccacaaatgc   1200
cacctcgaga acgaggtatg cttgctcgca tacactcaca ctggcttaca tatggcgctg   1260
cacatctgca gttcctctcc gttcttgaac atgcttactg acaaacatat ggccagctgc   1320
tgaggctgaa ggagagactg ggagcgactg agcaggaggt gcggcgcctc aggtcggcag   1380
ctgggagcca cggggcatct gtggatggcg gacacgccgc tggcgccgtt ggcgtgtgcg   1440
gcgggagccc gagctcgtcc ttctcgacgg gaacctgcca gcagcagccg ggtttcagcg   1500
gggcagacgt gctggggcgg gacgatgacc tgatgatgtg cgtccccgag tggttttag    1560 catgaattag agtttatgct ggctaagccg atagcagcgt ggtcgagtgt tttttagcat   1620
gaaatcagat ctccatctcc cataaaatag ccgagatagc tgctgccgcc gccaaatcct   1680
ctatagggct tcaagatcgg cagaaacctc tagaaatcat ctccccctc cggaaaagtc    1740 gcctctattt gtctccattg cccgcgatgc agcatccggt atagctgcta agacaggccg   1800
cccctaaatc gtttctccag cgattttaat ctttggtttt tagcctgtat atatgggctg   1860
tgatttgaag ttgagacgag ctggacatca actgcacgct gatcgattac tattctagtt   1920
tggcatagtg ttaattaagt ttggatgatc tctaggcgtg cgttaagtat gtagatagtg   1980
ttgattaatg gcaaaagctt gcaagttaag tgtagtattg gcagctctct tgaagatcaa   2040
atatgatgtg tgttatcatt tgatgatata tattttactt cagccgtaaa tagtcttctt   2100
agggaagcac tgtccatgta tgtgctggta gttggcattc atctttc                 2147
```

<210> SEQ ID NO 48
<211> LENGTH: 9
<212> TYPE: PRT
<213> ORGANISM: Artificial Sequence
<220> FEATURE:
<223> OTHER INFORMATION: consensus

<400> SEQUENCE: 48

Leu Ala Gly Leu Ile Asp Ala Asp Gly
1               5

<210> SEQ ID NO 49
<211> LENGTH: 13
<212> TYPE: PRT
<213> ORGANISM: Artificial Sequence
<220> FEATURE:
<223> OTHER INFORMATION: mutant

<400> SEQUENCE: 49

Gly Gly Gly Cys Cys Cys Gly Gly Cys Gly Ala Cys Gly
1               5                   10

HAPLOID INDUCER LINE FOR ACCELERATED GENOME EDITING

CROSS-REFERENCE TO RELATED APPLICATIONS

This application is a divisional of U.S. application Ser. No. 15/741,002, filed on Dec. 29, 2017, which is a National Stage application under 35 U.S.C. § 371 of International Application No. PCT/US2016/040398, having an International Filing Date of Jun. 30, 2016, which claims the benefit of U.S. Provisional Application No. 62/186,913, filed on Jun. 30, 2015, and U.S. Provisional Application No. 62/318,913, filed Apr. 6, 2016. The disclosures of the prior applications are considered part of (and are incorporated by reference in) the disclosure of this application.

SEQUENCE LISTING

This document contains a Sequence Listing that has been submitted electronically as an ASCII text file named "Sequence_Listing.txt." The ASCII text file, created on Feb. 8, 2022, is 48 kilobytes in size. The material in the ASCII text file is hereby incorporated by reference in its entirety.

TECHNICAL FIELD

This document relates to methods for using a haploid inducer line containing a targeted endonuclease to generate doubled haploid plants with targeted mutations in planta. The methods can be used with, for example, maize, wheat, oat, barley, triticale, and other species that utilize haploid inducer lines, as well as for *Arabidopsis* and other species that can generate haploids using a transgenic haploid inducer method. The methods can be used to generate transgenic or non-transgenic doubled haploid plants.

BACKGROUND

Traditional plant breeding strategies have been developed over many years to introduce desirable traits into plant species, such as increased yield, resistance to pests, disease, and/or drought, or adaptation to particular environments and growing conditions. Such strategies typically require many successive rounds of crossing, and thus it can take many years to successfully alter a specific plant trait. With the advent of transgenic technologies (also referred to as "molecular breeding"), it became possible to engineer plants with genomic alterations by introducing transgenic constructs or specific nucleotide sequence alterations, thus providing an additional tool for crop research and improvement. Genetic modification of plants can be achieved by adding one or more specific genes to a plant, or by knocking down gene expression (e.g., with RNAi), to produce a desirable trait. Modified plants can be produced relatively quickly, since the majority of the plant genome is not altered with genetic modification. To genetically modify a plant by adding a gene, for example, a construct is designed to express the gene in the plant—typically by including the gene of interest, a promoter to drive transcription of the gene, and a termination sequence to stop transcription of the gene. The construct carrying the gene(s) of interest is often accompanied by a selectable marker (e.g., an antibiotic or herbicide resistance gene) for selection of transformed plants. The construct may be inserted in the plant genome using, for example, *Agrobacterium*, particle bombardment, or a direct method such as microinjection. In some cases, a plant virus can be used to insert a genetic construct into a plant.

Transgenic techniques can have drawbacks, however. For example, transgene insertion into the genome (such as that mediated by particle bombardment) is largely random and can lead to multiple insertions, which can cause difficulties in tracking multiple transgenes present on different chromosomes during segregation. Further, expression of the transgene can be unpredictable due to its chromosomal location, and in some cases, expression of the transgene is silenced. In addition, production of transgenic plants has proven to be a very controversial topic, with public opinion often being against the creation of transgenic varieties—particularly where the varieties in question are crop plants that will be used as food for human consumption.

Genome editing is another method for using transgenes. In this method, a transgene can be introduced to produce a mutation at specific DNA sequence, and then the transgene is removed from the genome. For example, an endonuclease transgene can be inserted into the genome at a random location and expressed to produce a protein or RNA that targets and mutates a specific sequence of DNA at a second location in the genome. The transgene insertion site is most likely not linked with the mutated locus. Thus, the transgene can be removed from the genome by outcrossing of the plant or, if the transgene is not homozygous in the plant line, the transgene can be removed simply by selecting progeny that do not contain the transgene. Thus, a plant line can be produced that has a mutation at a specific DNA sequence and does not contain a transgene.

Traditional methods of introducing mutations into crop varieties (often referred to as "elite lines") can be time consuming and costly. Traditionally, transgenic modification utilizes lines that are amenable to transformation, but such lines usually are not agronomically competitive. Thus, the first step in genome engineering typically is to transform an endonuclease transgene into a line that is amenable to transformation to generate the desired mutation(s). Once the line is mutated, it is outcrossed to lines that are agronomically competitive (elite lines). The first crossing between a mutated line and an elite line generates "$F_1$," plants that contain half of their DNA from the mutated line and half of their DNA from the elite line. To recover the elite line's genetic background with the desired mutation(s), an $F_1$ plant is crossed to the elite line (a process called backcrossing) to produce a $BC_1F_1$ plant. The $BC_1F_1$ contains most of its DNA from the elite line and only some of its DNA from the mutated line. The process of backcrossing is repeated two, three, or more times until a sufficient percentage of the elite line's DNA composition is recovered. Selection with molecular markers can be used to ensure that the desired mutations are carried through the final backcrossing steps. Each round of backcrossing and molecular marker selection adds cost and time to the process. Further, if a mutation is desired to be in more than one elite line, the backcrossing process must be repeated to introduce the desired mutation into the additional elite lines.

SUMMARY

This document is based, at least in part, on the development of an effective in planta method for gene targeting that, in a single generation, results in mutated, doubled haploid plants that do not contain a transgene. The method utilizes a plant haploid inducer stock line containing one or more endonucleases to combine (a) haploid induction through crosses with (b) targeted DNA double strand breaks engineered by the endonuclease, followed by (c) chromosome doubling procedures. The plant bearing both the haploid inducer capacity and the endonuclease can simultaneously induce both haploidization and mutation, and is thus referred to as a Haploid Inducer Line for Accelerated Genome Editing (HILAGE). This gene targeting methodology can produce non-transgenic, doubled haploid individuals without the use of subsequent backcrossing procedures, and therefore is likely to have significant implications in many areas of plant biology. For example, the technology likely will increase the rate of plant functional genetics studies. In some cases, the materials and methods provided herein can be used to produce plants that are non-transgenic for the exogenous endonuclease sequences, but that contain a transgene inserted at a targeted location. The methods provided herein also can be used to engineer improved plant traits, such as increased production of commercially valuable compounds, improved flavor profiles, increased grain and/or biomass yields, enhanced nutritional quality, increased resistance and/or tolerance to biotic and abiotic stresses, improved agronomic characteristics, and improved aesthetic traits.

The methods provided herein can be used in plant species in which haploid individuals can be produced through crossing. The benefits of utilizing a HILAGE line carrying an endonuclease transgene to produce doubled haploid individuals with targeted gene mutations can include, for example, (i) the ability to rapidly produce targeted mutations in a genetic background regardless of the background's transformability; (ii) the generation of targeted mutations in planta avoids slow and costly whole plant transformation, since no further whole plant transformation is required once the transgene is in the HILAGE stock line; (iii) the retention of minimal or no DNA from the HILAGE line in the resulting plants, such that there is no need for timely and expensive backcrossing of the mutation into the elite line, and no yield drag caused by the initially transformed line's residual DNA containing non-elite genetics; (iv) the non-transgenic status of the resulting haploid and doubled haploid plants, at least with regard to the exogenous endonuclease sequence; and (v) the ready scalability of the method by adding more endonucleases to the HILAGE stock line in order to target more than one gene at a time. In addition to scalability in the number of mutations generated per line, the method also is highly scalable in the number of lines that can be mutated each year. These properties thus contribute to a method that is cost effective and time saving, is easily scalable and widely deployable, and can be readily incorporated into current breeding methodologies.

In one aspect, referred to herein as "HILAGE-Mutation" or "HILAGE-MUT," this document features a method for generating a doubled haploid plant cell having a mutation at or near a selected DNA sequence. In some embodiments, the method can include (a) transforming a haploid inducer line with a nucleic acid encoding a rare-cutting endonuclease to generate a HILAGE stock line having the nucleic acid stably integrated therein, wherein the nucleic acid encoding the rare-cutting endonuclease is operably linked to a promoter that is expressed in plant embryos during at least the first and second cell divisions after fertilization, and wherein the rare-cutting endonuclease is targeted to the selected DNA sequence; (b) crossing the HILAGE stock line with a targeted line to generate an $F_1$ zygote containing the stably integrated nucleic acid; (c) culturing the $F_1$ zygote such that (i) the rare-cutting endonuclease is expressed and cleaves chromosomal DNA at or near the selected DNA sequence, wherein repair of the chromosomal DNA after cleavage results in the mutation, and (ii) genome elimination takes place such that chromosomes from the HILAGE stock line are eliminated, resulting in a haploid cell; and (d) inducing chromosome doubling in the haploid cell to generate a doubled haploid plant cell containing the mutation. The plant cell can be from maize, wheat, barley, triticale, *Arabidopsis*, oat, pennycress, tomato, potato, soybean, or camelina. The rare-cutting endonuclease can be a transcription activator-like effector (TALE) endonuclease, a CRISPR/Cas-based nuclease, a zinc finger nuclease (ZFN), or a meganuclease. The promoter can be a cauliflower mosaic virus doubled enhanced 35S promoter, a maize ZmUb1 promoter, or a rice APX, OsCc1, EIF5, R1G1B, PGD1, Act1, or SCP1 promoter. The repair can include homologous recombination. The mutation can include one or more nucleotide substitutions, additions, or deletions, and/or insertion of a transgenic DNA sequence.

In some embodiments, a HILAGE-MUT method for generating a doubled haploid plant cell having a mutation at or near a selected DNA sequence can include (a) transforming a plant cell line with a nucleic acid encoding a rare-cutting endonuclease to generate a transgenic plant cell line having the nucleic acid stably integrated therein, wherein the nucleic acid encoding the rare-cutting endonuclease is operably linked to a promoter that is expressed in plant embryos during at least the first and second cell divisions after fertilization, and wherein the rare-cutting endonuclease is targeted to the selected DNA sequence; (b) crossing the transgenic plant cell line to a haploid inducer line to generate a HILAGE stock line that is homozygous for the nucleic acid encoding the rare-cutting endonuclease and is capable of inducing haploids upon crossing; (c) crossing the HILAGE stock line with a targeted line to generate an $F_1$ zygote containing the stably integrated nucleic acid; (d) culturing the $F_1$ zygote such that (i) the rare-cutting endonuclease is expressed and cleaves chromosomal DNA at or near the selected DNA sequence, wherein repair of the chromosomal DNA after cleavage results in the mutation, and (ii) genome elimination takes place such that chromosomes from the HILAGE stock line are eliminated, resulting in a haploid cell; and (e) inducing chromosome doubling in the haploid cell to generate a doubled haploid plant cell containing the mutation. The plant cell can be from maize, wheat, barley, triticale, *Arabidopsis*, oat, pennycress, tomato, potato, soybean, or camelina. The rare-cutting endonuclease can be a TALE endonuclease, a CRISPR/Cas-based nuclease, a ZFN, or a meganuclease. The promoter can be a cauliflower mosaic virus doubled enhanced 35S promoter, a maize ZmUb1 promoter, or a rice APX, OsCc1, EIF5, R1G1B, PGD1, Act1, or SCP1 promoter. The repair can include homologous recombination. The mutation can include one or more nucleotide substitutions, additions, or deletions, and/or insertion of a transgenic DNA sequence.

In some embodiments, a HILAGE-MUT method for generating a doubled haploid plant cell having a mutation at or near a selected DNA sequence can include (a) crossing a HILAGE stock line with a targeted line to generate an $F_1$ zygote containing a stably integrated nucleic acid, wherein the haploid inducer line includes a stably integrated nucleic acid encoding a rare-cutting endonuclease, wherein the nucleic acid encoding the rare-cutting endonuclease is operably linked to a promoter that is expressed in plant embryos during at least the first and second cell divisions after fertilization, and wherein the rare-cutting endonuclease is targeted to the selected DNA sequence; (b) culturing the $F_1$ zygote such that (i) the rare-cutting endonuclease is expressed and cleaves chromosomal DNA at or near the selected DNA sequence, wherein repair of the chromosomal DNA after cleavage results in the mutation, and (ii) genome elimination takes place such that chromosomes from the HILAGE stock line are eliminated, resulting in a haploid cell; and (c) inducing chromosome doubling in the haploid cell to generate a doubled haploid plant cell containing the mutation. The plant cell can be from maize, wheat, barley, triticale, Arabidopsis, oat, pennycress, tomato, potato, soybean, or camelina. The rare-cutting endonuclease can be a TALE endonuclease, a CRISPR/Cas-based nuclease, a ZFN, or a meganuclease. The promoter can be a cauliflower mosaic virus doubled enhanced 35S promoter, a maize ZmUb1 promoter, or a rice APX, OsCc1, EIF5, R1G1B, PGD1, Act1, or SCP1 promoter. The repair can include homologous recombination. The mutation can include one or more nucleotide substitutions, additions, or deletions, and/or insertion of a transgenic DNA sequence.

In another aspect, referred to herein as "HILAGE-Homologous Recombination" or "HILAGE-HR," this document features a method for generating a doubled haploid plant cell having a transgenic DNA sequence inserted at or near a selected DNA sequence. In some embodiments, the method can include (a) transforming a haploid inducer line with (i) a first transgenic DNA sequence flanked on both sides by DNA sequences homologous to sequences upstream and downstream of the selected DNA sequence, and (ii) a second transgenic sequence that encodes a rare-cutting endonuclease, to generate a HILAGE stock line having the first and second transgenic DNA sequences stably integrated therein, wherein the transgenic DNA sequence encoding the rare-cutting endonuclease is operably linked to a promoter that is expressed in plant embryos during at least the first and second cell divisions after fertilization, and wherein the rare-cutting endonuclease is targeted to the selected DNA sequence; (b) crossing the HILAGE stock line with a targeted line to generate an $F_1$ zygote containing the stably integrated transgenes; (c) culturing the $F_1$ zygote such that (i) the rare-cutting endonuclease is expressed and cleaves chromosomal DNA of the targeted line at or near the selected DNA sequence, and the first transgenic DNA sequence is inserted at the site of cleavage, and (ii) genome elimination takes place such that chromosomes from the HILAGE stock line are eliminated, resulting in a haploid cell; and (d) inducing chromosome doubling in the haploid cell to generate a doubled haploid plant cell containing the first transgenic DNA sequence. The plant cell can be from maize, wheat, barley, triticale, Arabidopsis, oat, pennycress, tomato, potato, soybean, or camelina. The rare-cutting endonuclease can be a TALE endonuclease, a CRISPR/Cas-based nuclease, a ZFN, or a meganuclease. The promoter can be a cauliflower mosaic virus doubled enhanced 35S promoter, a maize ZmUb1 promoter, or a rice APX, OsCc1, EIF5, R1G1B, PGD1, Act1, or SCP1 promoter.

In some embodiments, a HILAGE-HR method for generating a doubled haploid plant cell having a first transgenic DNA sequence inserted at or near a selected DNA sequence can include (a) transforming a plant cell line with (i) a first transgenic DNA sequence that is flanked on both sides by DNA sequences homologous to sequences upstream and downstream of the selected DNA sequence, and (ii) a second transgenic DNA sequence that encodes a rare-cutting endonuclease, to generate a transgenic plant cell line having the first and second transgenic DNA sequences stably integrated therein, wherein the transgenic DNA sequence encoding the rare-cutting endonuclease is operably linked to a promoter that is expressed in plant embryos during at least the first and second cell divisions after fertilization, and wherein the rare-cutting endonuclease is targeted to the selected DNA sequence; (b) crossing the transgenic plant cell line to a haploid inducer line to generate a HILAGE stock line that is homozygous for the first and second transgenic DNA sequences and can induce haploids upon crossing; (c) crossing the HILAGE stock line with a targeted line to generate an $F_1$ zygote containing the stably integrated transgenic DNA sequences; (d) culturing the $F_1$ zygote such that (i) the rare-cutting endonuclease is expressed and cleaves chromosomal DNA of the targeted line at or near the selected DNA sequence, and the first transgenic DNA sequence is inserted at the site of cleavage, and (ii) genome elimination takes place such that chromosomes from the HILAGE stock line are eliminated; and (e) inducing chromosome doubling in the haploid cell to generate a doubled haploid plant cell containing the first transgenic DNA sequence. The plant cell can be from maize, wheat, barley, triticale, Arabidopsis, oat, pennycress, tomato, potato, soybean, or camelina. The rare-cutting endonuclease can be a TALE endonuclease, a CRISPR/Cas-based nuclease, a ZFN, or a meganuclease. The promoter can be a cauliflower mosaic virus doubled enhanced 35S promoter, a maize ZmUb1 promoter, or a rice APX, OsCc1, EIF5, R1G1B, PGD1, Act1, or SCP1 promoter.

In some embodiments, a HILAGE-HR method for generating a doubled haploid plant cell having a transgenic DNA sequence inserted at or near a selected DNA sequence can include (a) crossing a HILAGE stock line with a targeted line to generate an $F_1$ zygote containing a stably integrated transgenic DNA sequence, wherein the HILAGE stock line includes (i) a stably integrated first transgenic DNA sequence flanked on both sides by DNA sequences homologous to sequences upstream and downstream of the selected DNA sequence, and (ii) a stably integrated second transgenic DNA sequence that encodes a rare-cutting endonuclease, wherein the transgenic DNA sequence encoding the rare-cutting endonuclease is operably linked to a promoter that is expressed in plant embryos during at least the first and second cell divisions after fertilization, and wherein the rare-cutting endonuclease is targeted to the selected DNA sequence; (b) culturing the $F_1$ zygote such that (i) the rare-cutting endonuclease is expressed and cleaves chromosomal DNA of the targeted line at or near the selected DNA sequence, and the first transgenic DNA sequence is inserted at the site of cleavage, and (ii) genome elimination takes place such that chromosomes from the HILAGE stock line are eliminated; and (c) inducing chromosome doubling in the haploid cell to generate a doubled haploid plant cell containing the first transgenic DNA sequence. The plant cell can be from maize, wheat, barley, triticale, Arabidopsis, oat, pennycress, tomato, potato, soybean, or camelina. The rare-cutting endonuclease can be a TALE endonuclease, a CRISPR/Cas-based nuclease, a ZFN, or a meganuclease. The promoter can be a cauliflower mosaic virus doubled enhanced 35S promoter, a maize ZmUb1 promoter, or a rice APX, OsCc1, EIF5, R1G1B, PGD1, Act1, or SCP1 promoter.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2B is a diagram depicting the steps in a method for using the HILAGE stock line of FIG. 2A to generate a doubled haploid elite line that is homozygous for a mutation engineered by an endonuclease and does not include an endonuclease transgene. The haploid inducer stock line in this diagram is depicted as the female parent in the cross. For haploid induction in certain species, however, the haploid inducer stock line is used as the male parent in the cross.

FIG. 4 is a representative GmCas9 nucleotide sequence (SEQ ID NO:1; 4140 nt, including a stop codon, optimized for GmCas9).

FIG. 5 is the full-length amino acid sequence (SEQ ID NO:2) of the GmCas9 nuclease (1379 aa), which is encoded by SEQ ID NO:1. The sequence includes an 11 amino acid modified nuclear localization signal (NLS; SEQ ID NO:4, encoded by SEQ ID NO:3) for *Arabidopsis* at the C-terminus.

FIG. 6 is the nucleotide sequence of a synthetic guide RNA (gRNA) cassette (SEQ ID NO:5). Lowercase text indicates the incorporated cloning sites, including protective base pairs. The transcription initiation site from the U6 promoter is shown as the bold and underlined guanine base (i.e., G) (this is also referred to as the first base of the gRNA). Underlined text is the primer sequence sites for amplifying the complete cassette.

DETAILED DESCRIPTION

In some embodiments, this document provides effective in planta methods for gene targeting that, in a single generation, can result in mutated, doubled haploid plants that do not contain a transgene. In some embodiments, the methods include the use of a plant HILAGE stock line encoding one or more targeted endonucleases to combine haploid induction (through crosses) with targeted DNA double strand breaks engineered by the endonuclease. Such methods can be used to introduce one or more mutations (e.g., substitutions, deletions, or insertions of one or more nucleotide bases) into a targeted plant line, and chromosome elimination and subsequent doubling procedures then can be used to generate doubled haploid plants. The methods provided herein can be used to produce non-transgenic (at least with respect to the exogenous endonuclease sequence), doubled haploid individuals without the use of subsequent backcrossing procedures.

Haploid plants contain half of the usual genomic content. Most, but not all, agronomic crop plants are diploid in that they have two complete sets of chromosomes, one from each parent. For the sake of this disclosure, it can be assumed that the species of interest are diploid, although it also is to be noted that the methods and materials described herein can be applied to polyploid species that have more than two sets of chromosomes. One method for generating haploid plants involves crossing a female parent with a haploid inducer male parent, which results in a haploid embryo with maternally inherited chromosomes. Alternatively, paternal haploid plants can be generated by crossing a male parent with a haploid-inducer female parent, which results in a haploid embryo with paternally inherited chromosomes. Haploid embryos and subsequent plants typically are smaller in size than diploid plants, and usually can be easily identified visually. Haploid plants can grow to maturity, but are generally sterile. Homozygous diploid plants can be produced from haploid plants by doubling of chromosomes from the haploid tissue through exposure to an agent such as colchicine, nitrous oxide gas, heat, or trifluralin. See, e.g., Wan et al., *Theor Appl Genet*, 77:889-892, 1989; and U.S. Publication No. 2003/0005479, which are incorporated herein by reference in their entirety. Chromosome doubling can produce completely homozygous diploid plants, referred to as doubled haploids. Doubled haploid plants can be fertile, and can perform as a normal diploid plant.

Figure 1:
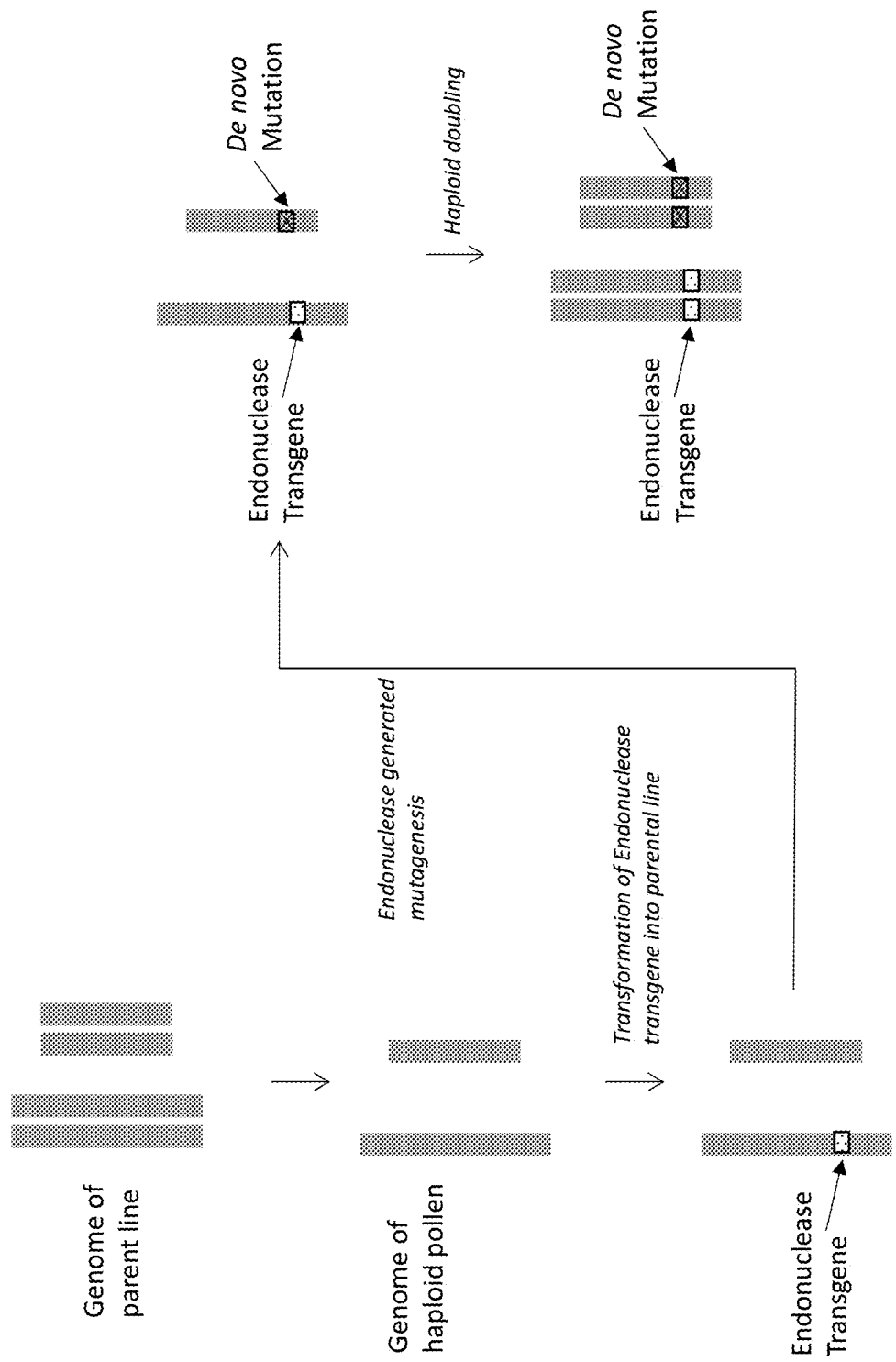
FIG. 1 is a diagram depicting the steps in a method for generating a doubled haploid plant cell containing a targeted mutation.

Haploid cells and chromosome doubling can be utilized in combination with a targeted endonuclease to generate plants having mutations engineered at one or more selected positions. One such method is depicted in FIG. 1. In this method, haploid pollen is transformed with a transgene encoding an endonuclease targeted to cleave the pollen's chromosomal DNA at a select site. The endonuclease is expressed in the pollen, leading to a chromosomal break at the site targeted by the endonuclease, thus generating a de novo mutation. Through chemical or spontaneous haploid doubling, the cell becomes doubled haploid.

While such methods result in a homozygous mutation at the target site, they also result in a homozygous transgene, which must be removed by outcrossing or backcrossing. In addition, outcrossing and backcrossing, or additional transformation followed by outcrossing to remove the transgene, are required to introgress the allele in elite lines.

In contrast, the methods provided herein utilize haploid inducers, endonucleases, and chromosome doubling techniques to efficiently produce homozygous, non-transgenic (at least with regard to the exogenous endonuclease sequence) plants that contain mutations at one or more loci and do not contain DNA from the HILAGE stock line. The HILAGE stock line carrying one or more transgenes encoding one or more endonucleases is crossed to one or more lines (referred to herein as "targeted lines") in which one or more targeted gene mutation(s) are desired. In some embodiments, a targeted line is an elite line. The HILAGE stock line's chromosomes are eliminated by the haploid induction process, resulting in a haploid line that only contains the DNA from the targeted line. Before the HILAGE stock line's chromosomes are eliminated, the endonuclease encoded by the transgene(s) in the HILAGE stock line causes mutations at the target location(s) in the targeted line's chromosomes. The plant that results from chromosome elimination is haploid, and has the exact genetic composition of the targeted line except for the desired targeted mutation(s). This haploid plant can be chromosome doubled to produce a fully inbred line that does not contain the exogenous endonuclease transgene, with the targeted line's genetics and the desired mutation(s). No backcrossing is needed to introgress the targeted mutation(s) into the targeted line, and no backcrossing is needed to remove the endonuclease transgene(s) or DNA derived from the HILAGE stock line.

Figure 2A:
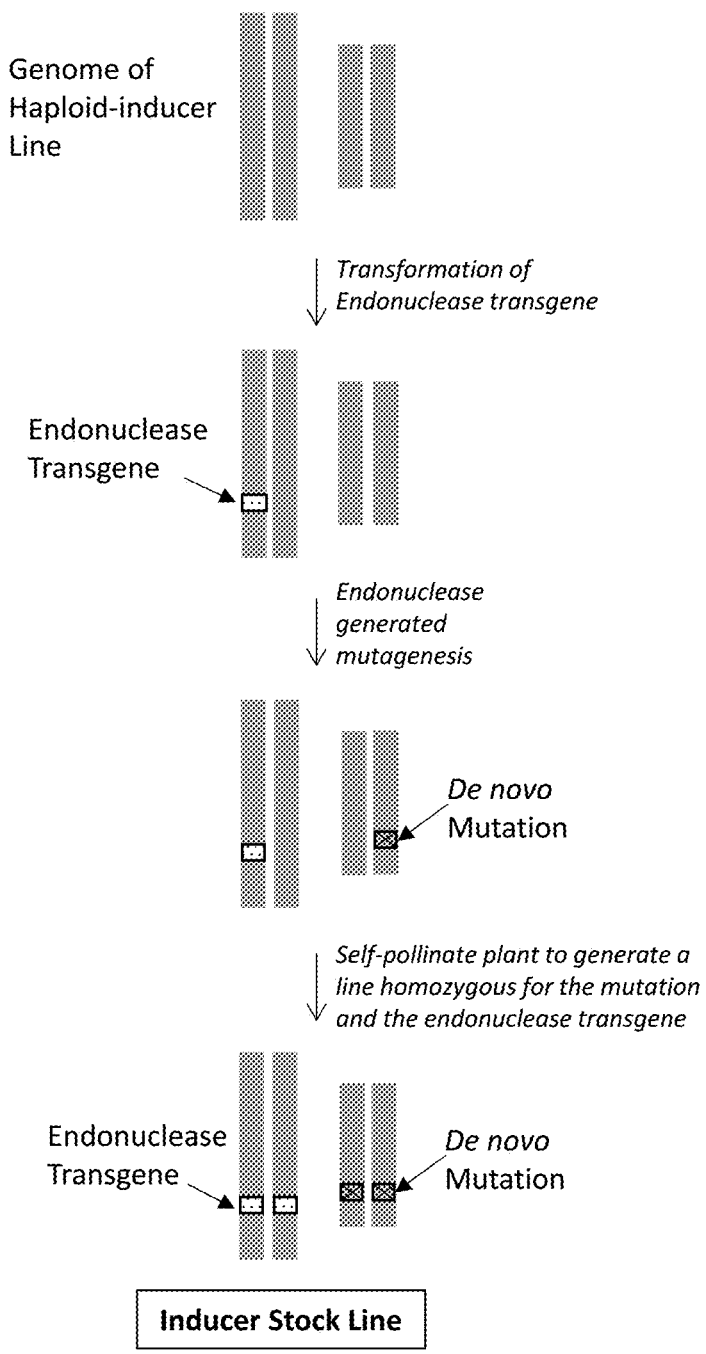
FIG. 2A is a diagram depicting the steps in a method for generating a HILAGE stock line that contains an endonuclease transgene and a mutation engineered by the endonuclease.

In some embodiments, the HILAGE-based methods disclosed herein can enable practitioners to achieve high frequencies of gene targeting by using an endonuclease expressed from a transgene to create a chromosome break at a target locus, while simultaneously producing a haploid line that does not contain the endonuclease transgene or the HILAGE stock line's DNA. To generate a HILAGE stock line, one or more endonuclease transgenes can be transformed directly into a haploid inducer line. Alternatively, one or more endonuclease transgenes can first be transformed into a line amenable to transformation, and then backcrossed into the haploid inducer stock line. An exemplary method for generating a HILAGE stock line is depicted in FIG. 2A. As shown, a haploid inducer line can be transformed with a transgene encoding an endonuclease, which then integrates into the genome of the haploid inducer line. Expression of the endonuclease protein from the transgene leads to targeted DNA cleavage and a de novo chromosomal mutation in the haploid inducer genome. Self-pollination is then used to generate a HILAGE stock line that is homozygous for the transgene (and also for the de novo mutation).

The HILAGE stock line then can be crossed to one or more lines in which one or more targeted gene mutations are desired (referred to herein as "targeted lines"). An example of this method is depicted in FIG. 2B. The cross between the two lines results in $F_1$ embryos, some of which will become haploid through the loss of the HILAGE stock line's chromosomes. During the brief time before the HILAGE stock line's chromosomes are eliminated from the embryo, however, the HILAGE stock line's endonuclease transgene(s) can be expressed and can generate targeted breaks in the targeted line's chromosomes, thus resulting in targeted de novo mutations in the targeted line's DNA. After subsequent chromosome elimination, the resulting haploid plant can be chromosome doubled to restore the diploid chromosome number. The resulting line (i) is diploid, (ii) is non-transgenic (at least for the endonuclease sequence), (iii) contains one or more homozygous targeted mutation(s), (iv) does not contain DNA from another line, and (v) is ready for field testing in one generation.

Haploid inducer lines typically are identified from interor specific intra-species crosses, which can result in haploid individuals for a certain percentage of the progeny. For example, in certain species (e.g., maize), haploid induction can be conducted using inter species crosses. Some maize lines have a propensity to produce a small percentage of haploid progeny when used in crosses. Some species require intra species crosses or 'wide' crosses in order to produce haploids. For example, crosses between (i) wheat and maize, (ii) barley and maize, and (iii) oat and maize result in the elimination of the maize chromosomes and the production of wheat, barley, and oat haploids, respectively. Certain transgenic modifications to the centromere histone CenH3 gene also have been demonstrated as a means to develop a haploid inducer line. These lines also induce haploidization based on sexual crosses. In theory, any haploid inducer line that generates haploids based on genome elimination following sexual crosses can be developed into a HILAGE stock by adding an endonuclease transgene that encodes for targeted modifications. Further, transgenic haploid induction technology, developed as described elsewhere (Ravi and Chan, *Nature* 464(7288):615-618, 2010), involves using a transgenically modified *Arabidopsis* plant to produce haploids through crossing.

The endonuclease that generates the targeted chromosome break can be a rare-cutting endonuclease such as, for example, a zinc finger nuclease (ZFN), a transcription activator-like effector (TALE) nuclease, a meganuclease, or a CRISPR/Cas system-based endonuclease, as further described below.

The transgene encoding the endonuclease can be operably linked to a promoter that is constitutive, cell specific, inducible, or activated by alternative splicing of a suicide exon, provided that the promoter is activated before chromosome elimination. Suitable promoters include, without limitation, the cauliflower mosaic virus doubled enhanced 35S (CaMV d35S) promoter, the native *Arabidopsis* 60S ribosomal protein promoter, and the native *Arabidopsis* expansin-like promoter. Typically, a promoter that is useful in the endonuclease constructs provided herein is one that drives expression in plant embryos during at least one of the first few cell divisions (e.g., at least the first or second cell division, the first and second cell divisions, the first through third cell divisions, or first through fourth cell divisions) after fertilization. In some cases, a promoter that can be used in an endonuclease construct provided herein is one that drives expression of an encoded endonuclease such that the endonuclease is active on its target site(s) present in the target line's chromosome(s) after fertilization.

As used herein, the term "transgene" or "transgenic DNA sequence" is meant to include not only sequences encoding polypeptides (e.g., polypeptides from exogenous species, such as the endonuclease transgenes described herein), but also regulatory sequences such as promoter sequences, cis-genes (genetic material from a different line of the same species, which may be inserted to, for example, switch out a native promoter for a different native promoter, or to add one or more additional copies of a native gene), and indeed, any DNA sequence that is not normally found at the location into which it is to be inserted.

In some embodiments, further transgenes can be added to the endonuclease construct to limit the targeted line's ability to conduct homologous recombination (HR) or non-homologous end joining (NHEJ), depending on whether HR or NHEJ is desired. Examples of such transgenes include RNAi transgenes that can be used to decrease expression of particular genes in order to encourage the plant's chromosome double strand break (DSB) repair mechanism in favor of HR or NHEJ (see, Gallego et al., *Plant J.* 35:557-565, 2003; Nishizawa-Yokoi et al., *New Phytologist* 196(4):1048-1059, 20012; and Qi et al., *Genome Res.* 23:547-554, 2013). For example, decreasing expression of Ku gene homologs (e.g., the rice and *Arabidopsis* Ku70 and Ku80 genes), Lig4, and/or RAD50 can increase the rate of HR. See, for example, Jia et al., *J. Botany* 2012, ID 9892722012; Qi et al., supra; Tanaka et al., *Biochem. Biophys. Res. Commun.* 396:289-293, 2010; Nishizawa-Yokoi et al., supra; and Gherbi et al., *EMBO Rep.* 2:287-291, 2001). In addition, certain transgenes can increase HR, including the *Escherichia coli* recA and ruvC genes, yeast Rad54, and homologs of rice ExoI (see, e.g., Reiss et al., *Proc. Natl. Acad. Sci. USA* 97:3358-3363, 2000; Shalev et al., *Proc. Natl. Acad. Sci. USA* 96:7398-7402, 1999; and Osakabe and Toki, unpublished results in Voytas, *Ann. Rev. Plant Biol.* 64:327-350, 2013). Expression of such transgenes may be driven by a strong promoter such as, without limitation, 35S (CaMV d35S) or derivatives thereof (e.g., double 35S), ZmUb1 (maize), APX (rice), OsCc1 (rice), EIF5 (rice), R1G1B (rice), PGD1 (rice), Act1 (rice), and SCP1 (rice). Alternatively or in addition to the RNAi transgenes, a HILAGE stock line may carry mutations in the above mentioned genes in order to promote HR or NHEJ.

In some HILAGE-HR embodiments, a transgenic construct encoding an endonuclease, or a second construct to be combined into the same plant line as the transgenic construct, can contain one or more copies of a DNA sequence having homology to the DNA at and flanking the target site. This sequence of DNA can contain nucleotide changes such as one or more base pair substitutions, deletions, and/or additions. Alternatively, this sequence may contain a gene, a promoter, a regulatory sequence, and/or a transgene.

In some cases, the HILAGE line can have a mutation at one or more of the sequences targeted by the endonuclease(s). The presence of the mutation(s) may increase the likelihood that a mutation is produced in the resulting haploid individual. If a chromosome break occurs in the targeted line and the broken chromosome is repaired by HR using the HILAGE stock's chromosome as the template, then the DSB can be "repaired" with the mutation present in the HILAGE stock line.

In some HILAGE-HR embodiments, a HILAGE line can have a second transgenic DNA sequence at one or more of the sequences targeted by the endonuclease(s), such that the DSB generated as a result of expressing the endonuclease from the HILAGE stock can be repaired by integration of the second transgenic DNA sequence. See, e.g., FIG. 3. Further, in some HILAGE-HR embodiments, a DSB can be repaired by HR using the HILAGE genotype locus as a template, or by using a transgenic sequence containing specific nucleotide changes in the HILAGE stock as a template, thus resulting in a mutation.

In some embodiments, two or more (e.g., two, three, four, or more than four) different or identical endonucleases and/or CRISPR guide RNAs can be located on separate chromosomes of a HILAGE stock line. Localizing two or more endonucleases and/or CRISPR guide RNAs on separate chromosomes may increase the likelihood that one or more of the endonucleases will remain in the plant for a longer period of time, particularly for plants (e.g., oat) in which chromosomes are lost over time. The longer an endonuclease persists in the plant before being lost, the greater the chance that the endonuclease will effectively cause a double stranded break at the target site.

In some cases, multiple loci can be targeted for mutation. It is possible that in different doubled haploid progeny, only one or a few, but not all, of the multiple target sites will be mutated. Doubled haploid progeny derived from the same targeted line can be crossed together to combine the targeted mutations. Since the doubled haploid individuals differ only by mutations at the targeted loci, the mutations can be combined without the need to select on the rest of the genome. For example, if mutations are desired at three target loci (Locus A, Locus B, and Locus C), but only doubled haploid progeny with mutations at Loci A and B (a/a, b/b, C/C) and Loci A and C (a/a, B/B, c/c) are recovered, an individual with mutations at Loci A and B (a/a, b/b, C/C) can be crossed to an individual with mutations at Loci A and C (a/a, B/B, c/c) to produce an individual with mutations at all loci (a/a, B/b, C/c). Self-pollinating the $F_1$ individual (a/a, B/b, C/c) and screening the $F_2$ progeny can result in recovery of the desired individual (a/a, b/b, c/c) with mutations at all three loci.

In some embodiments, a cross can be conducted between an $F_1$ plant and a HILAGE stock line (rather than by crossing a homozygous parent line to the haploid inducer stock line). In such embodiments, the doubled haploid progeny produced will differ for both their genetics and for the presence or absence of a targeted mutation(s).

Different mutations may be produced, and evaluation of each mutation event is necessary to determine if the mutation(s) obtained have the desired result. Mutations that produce a desired phenotype, such as mutations that cause a frame shift and eliminate proper gene function, are referred to herein as "effective mutations" (EM). In some cases, only lines with EM are advanced. In some embodiments, HILAGE-based methods are used to add new mutations to a line that already has one or more EM. This method also can be used to combine two or more EM into a single line.

In some embodiments, lines with different HILAGE-induced mutations and different genetic backgrounds are crossed together to combine the EM. The resulting progeny can segregate for both the EM and for their genetic background.

In some embodiments, through HR, HILAGE-based methods can produce progeny having the same mutation as the HILAGE inducer line.

Figure 3:
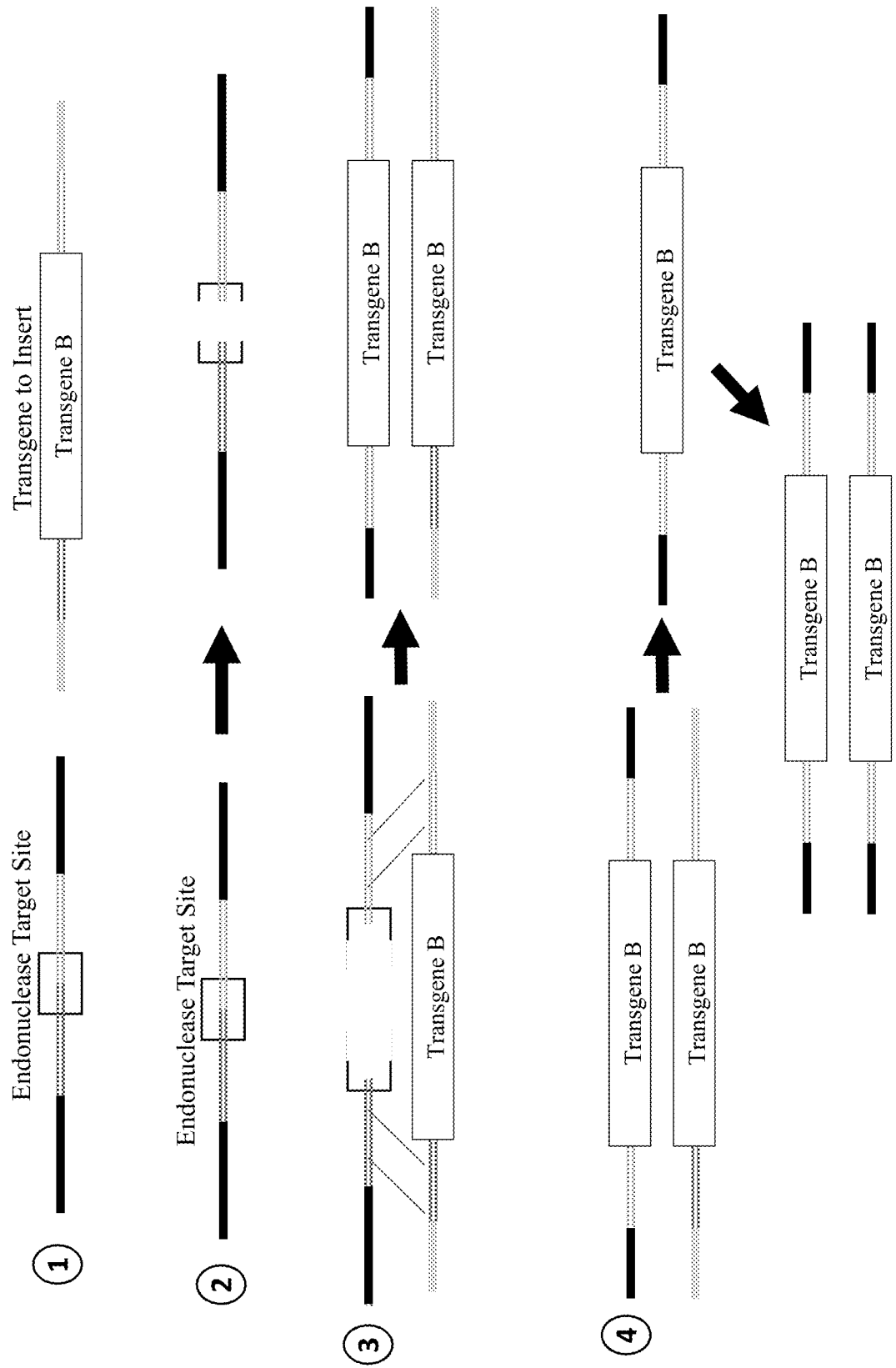
FIG. 3 is a diagram depicting the steps in a procedure for inserting a transgene into a targeted line's genome by crossing a HILAGE stock line with a targeted line. (1) shows the endonuclease target site and the transgene to be inserted. The HILAGE line DNA strand is flanked by light grey tips, while the targeted line's DNA strand is flanked by black tips. The HILAGE stock line contains both an endonuclease transgene ("Transgene A") to generate a double strand break in the targeted line's DNA at a selected location, and a transgene to be inserted ("Transgene B") into the targeted line at the location of the double strand break. The transgene is flanked on each side by sequences identical to chromosomal sequences surrounding the endonuclease target site. The identical sequences are represented by two light grey lines. In (2), a double strand break (DSB) in the targeted line's chromosome is created by the HILAGE stock line's endonuclease ("Transgene A"). In (3), the targeted line conducts homologous recombination (HR) repair using the HILAGE line's chromosome as the template strand. The chromosome template provided by the HILAGE line carries the Transgene B to be inserted. Transgene B is effectively integrated into the targeted line's chromosome using HR. In (4), the HILAGE line's chromosomes are lost, resulting in a haploid plant with the genetics matching the targeted line, with a Transgene B inserted at the specific location. The haploid plant can be chromosome doubled to produce a doubled haploid line.

In some HILAGE-HR embodiments, an endonuclease construct can be paired with a transgene or quantitative trait locus (QTL) to be inserted into the endonuclease target site in a targeted line. The endonuclease construct and transgene to be inserted can be in the same construct in a HILAGE line or in different constructs in the same HILAGE line. The transgene to be inserted into the targeted line's genome can be flanked on each side by DNA sequences homologous to the DNA sequences flanking the target site of the endonuclease in the targeted line (FIG. 3). Such embodiments can be used in situations in which the transgene is positioned in the haploid inducer genome at "location B" but it is desired to move the transgene to "location A" in the DNA of the non-haploid inducer. In some embodiments, such methods can be used to insert a transgene at a specific DNA sequence in an elite cultivar without having to conduct backcrossing to remove non-elite chromosome material from the elite line.

In some embodiments, the endonuclease can be designed to target a genome sequence that is identical to the sequence flanking the transgene to be inserted into a target line after the transgene has been positioned in the genome. After generation of a DSB at the target site, the plant cell can undergo HR in order to repair the DSB. The HILAGE line can supply the DNA template—the transgene flanked by DNA sequences homologous to endogenous DNA sequences flanking the target site. When the targeted line's chromosome break is repaired using the HILAGE line's strand containing the transgene, the transgene is effectively inserted into the targeted line's chromosome at the DSB.

The plants that can be mutated and/or genetically modified and then double haploidized according to the methods provided herein can be monocotyledonous (e.g., maize, barley, wheat, triticale, or oat) or dicotyledonous (e.g., Arabidopsis, potato, tomato, soybean, pennycress, or camelina), as further described below.

Suitable haploid inducer lines can be generated from, for example, maize, barley, wheat, triticale, oat, sorghum, potato, teosinte, and teff. Naturally occurring maize haploid inducer lines can be readily obtained, as they are used in academia and industry. In some embodiments, the haploid inducer line used in the methods provided herein can be of a species other than maize. In some cases, a haploid inducer line that contains B chromosomes can be used as described herein, while in other cases, a haploid inducer line that lacks B chromosomes can be used as described herein. Barley haploids can be generated by crossing cultivared barley (Hordeum vulgare) to its wild progenitor species (Hordeum bulbosum). The developing barley embryos can be grown in tissue culture (a process called embryo rescue) to generate whole plants. Wheat, triticale, and oat haploids can be generated by pollinating emasculated wheat and triticale spikes and oat panicles with pollen from related species such as, without limitation, maize, sorghum, barley (H. bulbosum), and millet. As with barley, the wheat, triticale, and oat developing embryos must be embryo rescued to generate whole plants. Haploid plants also can be generated in Arabidopsis, and likely in other species, using a transgenic haploid inducer line (Ravi and Chan, supra). Haploids in potato can be generated by crossing the conventional tetraploid with a diploid Solanum tuberosum gp. Phureja clone (Peloquin, Hougas and Gabert, Am J Potato 37:289-297, 1960; and Hermsen and Verdenius, Euphytica 22(2):244-259, 1973).

Several categories of crosses that can be made to generate haploid inducer lines, including those discussed above, are summarized in TABLE 1:

TABLE 1

| Maize, sorghum, teiosinte, or teff | Wheat |
| | Oat |
| | Barley |
| | Triticale |
| | Rye* |
| Wild relative | Barley |
| | Potato |
| Maize | Maize |
| Arabidopsis with CenH3 mutation | Arabidopsis |
| | Sugar beet* |
| | Barley* |
| | Soybean* |
| | Potato* |

*Possible

As used herein, "plants" and "plant parts" refers to cells, tissues, organs, seeds, and severed parts (e.g., roots, leaves, and flowers) that retain the distinguishing characteristics of the parent plant. "Seed" refers to any plant structure that is formed by continued differentiation of the ovule of the plant, following its normal maturation point at flower opening, irrespective of whether it is formed in the presence or absence of fertilization and irrespective of whether or not the seed structure is fertile or infertile.

The term "allele(s)" means any of one or more alternative forms of a gene at a particular locus. In a diploid (or amphidiploid) cell of an organism, alleles of a given gene are located at a specific location or locus on a chromosome. One allele is present on each chromosome of the pair of homologous chromosomes. "Heterozygous" alleles are two different alleles residing at a specific locus, positioned individually on corresponding pairs of homologous chromosomes. "Homozygous" alleles are two identical alleles residing at a specific locus, positioned individually on corresponding pairs of homologous chromosomes in the cell.

"Wild type" as used herein refers to a typical form of a plant or a gene as it most commonly occurs in nature. "Mutant" refers to a plant or a gene that includes one or more changes (e.g., nucleotide substitutions, deletions, or additions) in its nucleic acid sequence as compared to the wild type sequence. In some embodiments, a mutation may result in no detectable amount of functional protein in the plant or plant cell in vivo, or may refer to one or more amino acid changes in the protein produced. In some embodiments, a mutation can include an inserted transgene.

"Mutagenesis" as used herein refers to processes in which mutations are introduced into a selected DNA sequence. Mutations induced by endonucleases generally are obtained by a double strand break, which can result in insertions or deletions ("indels") that can be detected by sequencing analysis. Such mutations typically are deletions of several base pairs, and have the effect of inactivating the mutated allele.

The term "rare-cutting endonucleases" as used herein refers to natural or engineered proteins having endonuclease activity directed to nucleic acid sequences having a recognition sequence (target sequence) about 12-40 bp in length (e.g., 14-40 or 15-30 bp in length). Typical rare-cutting endonucleases cause cleavage inside their recognition site, leaving 4 nt staggered cut with 3'OH or 5'OH overhangs. These rare-cutting endonucleases may be meganucleases, such as wild type or variant proteins of homing endonucleases, more particularly belonging to the dodecapeptide family (LAGLIDADG (SEQ ID NO:48); see, WO 2004/067736) or may result from fusion proteins that associate a DNA binding domain and a catalytic domain with cleavage activity. TAL-effector endonucleases and zinc-finger-nucleases (ZFN) are examples of fusions of DNA binding domains with the catalytic domain of the endonuclease FokI. Customized TAL effector endonucleases are commercially available under the trade name TALEN™ (Cellectis, Paris, France). For a review of rare-cutting endonucleases, see Baker, Nature Methods 9:23-26, 2012.

For example, in some embodiments, mutagenesis can occur via a double stranded DNA break made by a TAL effector endonuclease targeted to a selected DNA sequence in a plant cell. Such mutagenesis results in "TAL effector endonuclease-induced mutations" (e.g., TAL effector endonuclease-induced knockouts) and reduced expression of the targeted gene. Methods for selecting endogenous target sequences and generating TAL effector endonucleases targeted to such sequences can be performed as described elsewhere. See, for example, PCT Publication No. WO 2011/072246 (which is incorporated herein by reference in its entirety). TAL effectors are found in plant pathogenic bacteria in the genus Xanthomonas. These proteins play important roles in disease, or trigger defense, by binding host DNA and activating effector-specific host genes (see, e.g., Gu et al., *Nature* 435:1122-1125, 2005; Yang et al., *Proc. Natl. Acad. Sci. USA* 103:10503-10508, 2006; Kay et al. *Science* 318:648-651, 2007; Sugio et al., *Proc. Natl. Acad. Sci. USA* 104:10720-10725, 2007; and Romer et al. *Science* 318:645-648, 2007). Specificity depends on an effector-variable number of imperfect, typically 34 amino acid repeats (Schornack et al., *J. Plant Physiol.* 163:256-272, 2006; and WO 2011/072246). Polymorphisms are present primarily at repeat positions 12 and 13, which are referred to herein as the repeat variable-diresidue (RVD).

The RVDs of TAL effectors correspond to the nucleotides in their target sites in a direct, linear fashion, one RVD to one nucleotide, with some degeneracy and no apparent context dependence. This mechanism for protein-DNA recognition enables target site prediction for new target specific TAL effectors, as well as target site selection and engineering of new TAL effectors with binding specificity for the selected sites.

TAL effector DNA binding domains can be fused to other sequences, such as endonuclease sequences, resulting in chimeric endonucleases targeted to specific, selected DNA sequences, and leading to subsequent cutting of the DNA at or near the targeted sequences. Such cuts (i.e., double-stranded breaks) in DNA can induce mutations into the wild type DNA sequence via NHEJ or HR, for example. In some cases, TAL effector endonucleases can be used to facilitate site directed mutagenesis in complex genomes, knocking out or otherwise altering gene function with great precision and high efficiency. The fact that some endonucleases (e.g., FokI) function as dimers can be used to enhance the target specificity of the TAL effector endonuclease. For example, in some cases a pair of TAL effector endonuclease monomers targeted to different DNA sequences can be used. When the two TAL effector endonuclease recognition sites are in close proximity, the inactive monomers can come together to create a functional enzyme that cleaves the DNA. By requiring DNA binding to activate the nuclease, a highly site-specific restriction enzyme can be created.

In some embodiments, a rare-cutting endonuclease can be a CRISPR/Cas-based nuclease. In its native context, the CRISPR/Cas system provides bacteria and archaea with immunity to invading foreign nucleic acids (Jinek et al. *Science* 337:816-821, 2012). The CRISPR/Cas system is functionally analogous to eukaryotic RNA interference, using RNA base pairing to direct DNA or RNA cleavage. This process relies on (a) small RNAs that base-pair with sequences carried by invading nucleic acid, and (b) a specialized class of Cas endonucleases that cleave nucleic acids complementary to the small RNA. The CRISPR/Cas system can be reprogrammed to create targeted double-strand DNA breaks in higher-eukaryotic genomes, including animal and plant cells (Mali et al., *Science* 339:823-826, 2013; and Li et al., *Nature Biotechnology* 31(8): 688-691, 2013). Further, by modifying specific amino acids in the Cas protein that are responsible for DNA cleavage, the CRISPR/Cas system can function as a DNA nickase (Jinek et al., supra), or as a DNA binding protein that has no nuclease or nickase activity but is capable of interfering with incoming proteins, including RNA polymerases (Qi et al., *Cell* 152:1173-1183, 2013).

Directing DNA DSBs, single strand nicks, or binding of the Cas9 protein to a particular sequence requires CRISPR RNA (crRNA) and tracer RNA (tracrRNA) sequences that aid in directing the Cas/RNA complex to target DNA sequence (Makarova et al., *Nat Rev Microbiol*, 9(6):467-477, 2011). The modification of a single targeting RNA can be sufficient to alter the nucleotide target of a Cas protein. In some cases, crRNA and tracrRNA can be engineered as a single cr/tracrRNA hybrid to direct Cas activity, whether as a nuclease, a nickase, or a DNA binding protein.

In some embodiments, a rare-cutting endonuclease can be a ZNF, which is a fusion that contains engineered zinc-finger domains with the catalytic domain of a restriction enzyme such as FokI (Porteus and Carroll, *Nature Biotechnol* 23:967-973, 2005) or a chemical endonuclease (Eisenschmidt et al., *Nucl Acids Res* 33:7039-7047, 2005; Arimondo et al., *Mol Cell Biol* 26:324-333, 2006; and Simon et al., *Biochimie* 90:1109-1116, 2008). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of ortho-phenanthroline, a DNA cleaving molecule, and triplex-forming oligonucleotides (TFOs), known to bind specific DNA sequences (Kalish and Glazer, *Ann NY Acad Sci* 1058:151-161, 2005). Such chemical endonucleases are comprised in the term "endonuclease" according to the present document. Examples of such endonuclease include I-Sce I, I-Chu I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, and I-MsoI.

The term "expression" as used herein refers to the transcription of a particular nucleic acid sequence to produce sense or antisense mRNA, and/or the translation of a sense mRNA molecule to produce a polypeptide, with or without subsequent post-translational events.

In some embodiments, expression of the targeted gene can be reduced as a result of cleavage by the endonuclease. As used herein, "reducing the expression" of a gene or polypeptide in a plant or a plant cell includes inhibiting, interrupting, knocking-out, or knocking-down the gene or polypeptide, such that transcription of the gene and/or translation of the encoded polypeptide are reduced as compared to a corresponding wild type plant or plant cell. Expression levels can be assessed using methods such as, for example, reverse transcription-polymerase chain reaction (RT-PCR), Northern blotting, dot-blot hybridization, in situ hybridization, nuclear run-on and/or nuclear run-off, RNase protection, or immunological and enzymatic methods such as ELISA, radioimmunoassay, and western blotting.

The polynucleotides, vectors, and polypeptides described herein can be introduced into a number of monocotyledonous and dicotyledonous plants and plant cell systems, including dicots such as *Arabidopsis*, potato, tomato, soybean, pennycress, and camelina, as well as monocots such as, corn, barley, wheat, triticale, and oat.

The methods described herein can be utilized with dicotyledonous plants belonging, for example, to the orders Magniolales, Illiciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. The methods can be used over a broad range of plant species, including species from the dicot genera *Atropa, Alseodaphne, Anacardium, Arachis, Beilschmiedia, Brassica, Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vitis,* and *Vigna.*

The methods described herein also can be utilized with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales, or with plants belonging to Gymnospermae, e.g., Pinales, Ginkgoales, Cycadales and Gnetales. The methods can be used over a range of species from the monocot genera *Allium, Andropogon, Aragrostis, Asparagus, Avena, Cynodon, Elaeis, Festuca, Festulolium, Heterocallis, Hordeum, Lemna, Lolium, Musa, Oryza, Panicum, Pannesetum, Phleum, Poa, Secale, Sorghum, Triticum,* and *Zea*; or the gymnosperm genera *Abies, Cunninghamia, Picea, Pinus,* and *Pseudotsuga.*

A plant cell, plant tissue, or whole plant can be identified and isolated by selecting or screening the engineered cells for particular traits or activities, e.g., those encoded by marker genes or antibiotic resistance genes. Such screening and selection methodologies are well known to those having ordinary skill in the art. In addition, physical and biochemical methods can be used to identify transformants. These include Southern blot analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides.

Polynucleotides that are stably incorporated into plant cells can be introduced into other plants using, for example, standard breeding techniques.

The invention will be further described in the following examples, which do not limit the scope of the invention described in the claims.

EXAMPLES

Example 1—HILAGE: *Arabidopsis*

GmCRISPR Construct Assembly: The GmCRISPR construct consists of a Cas9 nuclease and a guide RNA (gRNA). These two genes were assembled in separate vectors and then combined together into a single vector.

Cas9 Assembly: A Cas9 nuclease was codon optimized to match the primary codon usage of soybean (*Glycine max*). The Cas9 nuclease alternatively could have been designed to match the primary codon usage of *Arabidopsis thaliana* or another plant or animal species. An *Arabidopsis* Nuclear Localization Signal (NLS) based on SV40 (Hicks et al., Plant Physiol 107(4):1055-1058, 1995) was added to the C terminus of the codon optimized Cas9 protein. The Cas9-NLS cassette, referred to henceforth as GmCas9 (SEQ ID NO:1, FIG. 4, encoding SEQ ID NO:2, FIG. 5), was synthesized by Life Technologies (New York). AscI and PacI restriction sites were present upstream and downstream of the GmCas9 cassette, respectively. The synthesized GmCas9 was cloned into the pmDC32 gateway vector using digestion with AscI and PacI followed by ligation, which replaced a ccdB gene in pmDC32. A NOS terminator was present in the pmDC32 plasmid downstream of the PacI restriction site and upstream of an EcoRI restriction site.

The GmCas9-NOS fragment was transferred from pmDC32 to the destination vector (pmDC123) by digesting both plasmids with AscI and EcoRI, followed by ligation, to replace the ccdB gene. The pmDC123 destination vector contains Kanamycin resistance while the gateway vector pmDC32 plasmid contains Hygromycin resistance, allowing the use of Kanamycin selection to recover the destination vector. The pmDC123 plasmid also contains the BAR gene for resistance to the herbicide bialaphos driven by the CaMV 35S promoter, making herbicide selection possible after whole plant transformation. A cauliflower mosaic virus doubled enhanced 35S (CaMV d35S) promoter flanked by HindIII and AscI restriction sites was added in front of the GmCas9 cassette using digestion with HindIII and AscI followed by ligation.

Several versions of the pmDC123 GmCas9 cassette were created using different promoters driving GmCas9. These promoters were PCR amplified from *Arabidopsis thaliana* genomic DNA using KOD polymerase (Novozyme, Denmark) and PCR primers designed to contain HindIII and AscI restriction sites in the forward and reverse primers, respectively. PCR amplicons were double digested with HindIII and AscI and cloned into pmDC123 using the HindIII and AscI restriction sites to replace the d35S promoter.

TABLE 2

Promoters tested

| Promoter # | Promoter | *Arabidopsis* Gene |
|---|---|---|
| 1 | Doubled enhanced 35S (CaMV d35S) | Na |
| 2 | Native *Arabidopsis* 60S Ribosomal protein | AT5G40040 |
| 3 | Native *Arabidopsis* Expansin-Like | AT3G45970 |
| 4 | Native *Arabidopsis* Inorganic Phosphate Transport 1-4 (PHT1; 4) | AT2G38940 |

The PCR primers used to amplify the promoters were:

```
Expansin-like protein gene promoter: AT3G45970
                                       (SEQ ID NO: 6)
F 5' CCAAGCTTCCCAACTACACGATGGACTCAC 3'

(SEQ ID NO: 7)
R 5' CCGGCGCGCCATGTAAAGAGAAGAGAGGACAAAG 3'

60S acidic ribosomal protein gene promoter
AT5G40040
                                       (SEQ ID NO: 8)
F 5' CCAAGCTTCCCAACTACACGATGGACTCAC 3'

(SEQ ID NO: 9)
R 5' CCGGCGCGCCATGTAAAGAGAAGAGAGGACAAAG 3'
```

-continued

Native *Arabidopsis* Inorganic Phosphate Transport
1-4 (PHT1;4)

(SEQ ID NO: 10)
F 5' CGAAAATAAATGAAGGCATCAATAAAAGCTTACC 3'

(SEQ ID NO: 11)
R 5' GTCAGCTCGGCGCGCCTCTTCTTCTCCTCTGCAATTTTTCA

TCAC 3' pBS gRNA Cassette and Vector Assembly: An *Arabidopsis thaliana* AtU6 promoter (AT3G13855) was designed to drive expression of the gRNA (FIG. 6). A synthetic cassette was generated by Life Technologies (New York) that consisted of an AtU6 promoter and gRNA expression cassette followed by a terminator consisting of eight thymine residues. Both ends of the cassette contained EcoRI restriction sites. This expression cassette was cloned into the pBS vector using EcoRI digestion followed by ligation. The 20 base pair (bp) target sequence fragment was synthesized using a pair of 24 bp PCR primers with a 20 bp complimentary sequence. To generate the target sequence fragment, the two reverse complimentary primers were annealed together in a 1×PCR buffer solution for three hours at anneal temperatures corresponding to the annealing temperatures of the PCR primers. When combined, the pair of primers generated 4 bp 5' overhangs on each end of the fragment, designed to be compatible with BbsI sites. To insert the target sequence fragment into the gRNA, the vector was digested by BbsI at the two BbsI sites designed inside the target sequence 20 bp spacer. Digestion by BbsI removed the 20 bp spacer to allow insertion of the target sequence fragment. Following digestion, the plasmid was treated with Calf Intestinal Phosphatase (CIP; New England Biolabs, MA). The target sequence fragment was then ligated into the gRNA vector between the BbsI sites.

Sequences of the target oligonucleotides were as follows (with f1/r1 being for target 1 and f2/r2 being for target 2):

GL1 gene (AT3G27920.1)

(SEQ ID NO: 12)
f1 5' GATT<u>GAGAATCAAGAATACAAGAA</u> 3'

(SEQ ID NO: 13)
r1 5' AAACTTCTTGTATTCTTGATTCTC 3'

(SEQ ID NO: 14)
f2 5' GATT<u>GGAAAAGTTGTAGACTGAGA</u> 3'

(SEQ ID NO: 15)
r2 5' AAACTCTCAGTCTACAACTTTTCC 3'

Underlining indicates the 20 bp target sequences.

Combining GmCas9 and gRNA cassettes to form the CRISPR construct: With the ccdB site replaced by the GmCas9 cassette, the EcoRI site in the pmDC123 became a unique cut site. The same EcoRI cut sites used to insert the expression cassette into the pBS vector were used to clone the gRNA into the pmDC123 vector downstream of the GmCas9 cassette. The pmDC123 vector, containing the GmCas9 cassette, was digested with EcoRI and CIP treated. The pBS vector also was digested with EcoRI. The gRNA cassette was then ligated into the pmDC123 plasmid between the EcoRI restriction sites. This construct is referred to going forward as the GmCRISPR construct.

Gus Construct Creation: Several GUS expression constructs were created to test the efficacy of the selected promoters (TABLE 2). The promoters were inserted into the pmDC123 plasmid as previously described. The GUS reporter gene was inserted into pmDC123 between the AscI and PacI sites, to replace the GmCas9 fragment without disrupting the NOS terminator fragment. These constructs are referred to herein as the GUS constructs.

Plant Materials: Columbia (Col) *Arabidopsis thaliana* seeds homozygous for the CenH3 GFP-TS-HFD haploid inducer transgene (Ravi and Chan, supra) and segregating for a Single Nucleotide Polymorphism (SNP) in CenH3 (AT1G01370), referred to herein as the CenH3 SNP, were provided by Dr. Luca Comai (UC-Davis). Progeny were genotyped for the presence of the CenH3 SNP following the methods outlined by Ravi and Chan (supra), who had observed that when outcrossed to wild type *Arabidopsis*, individuals homozygous for the CenH3 GFP-TS-HFD haploid inducer transgene and homozygous for the mutant CenH3 SNP produced a small percentage of haploid individuals not containing the inducer line's chromosomes. The individuals homozygous for the mutant CenH3 SNP were mostly male sterile, and thus, individuals heterozygous for the CenH3 SNP change need to be maintained in order to produce more individuals with the homozygous mutant CenH3 SNP. Ler plants with Kanamycin resistance were obtained from Cold Spring Harbor's Gene Trap lines. Plant materials were grown in a growth chamber either in potting mix soil or in petri dishes on ½MS media with 0.8% agar and 1% sucrose. The growing conditions were 16 hours of light, and temperatures of 22° C. and 20° C. during the day and night, respectively. Plants in soil were fertilized with half strength Hoglands solution every other week.

Plant Transformation: *Arabidopsis* plants were transformed using the floral dip method (Clough and Bent, *Plant J*, 16(6):735-743, 1998). The GmCRISPR constructs were transformed into plants that were homozygous for the CenH3 GFP-TS-HFD haploid inducer transgene and genotyped as heterozygous for the SNP change in (AT1G01370). *Arabidopsis thaliana* gl1 gl1 plants were transformed, via floral dip, with the GUS constructs. *Arabidopsis thaliana* Columbia (Col) plants also were transformed with the GUS constructs.

Screening $T_1$ seed for plants containing the GmCRISPR or Gus constructs: After floral dipping, the plants were allowed to mature and set seed. The $T_1$ seeds were dried at room temperature for 7 days after harvesting. $T_1$ seeds were planted out in trays filled with potting mix. The soil of the flats was misted with water and the flats were covered with a clear lid to maintain higher moisture levels. Ten days after germination, the flat was sprayed with a 0.01% solution of Basta herbicide (Glufosinate) to select individuals containing the pmDC123 constructs. Seventeen (17) days after germination, a second Basta spray was conducted to again select individuals containing the pmDC123 constructs. Plants that survived both rounds of Basta spray were transplanted to individual pots and assigned a plant identification number. This procedure was used to screen for plants containing the GmCRISPR construct or the Gus constructs.

Testing promoters using GUS expression assays: After surviving the Basta herbicide spray, the $T_1$ plants containing a GUS construct were grown to the flowering stage. During flowering, flowers at various stages of growth were excised from the plant and stained following the GUS staining protocol. The flowers were dissected, and the presence of GUS staining was assessed under a dissecting microscope. The plants were also grown out to set seed to maintain the lines.

Screening $T_1$ CRISPR plants for mutations at the Gl1 locus (AT3G27920): After surviving the Basta herbicide spray, $T_1$ plants containing a GmCRISPR construct were visually inspected to identify plants not having trichomes or having sections of leaves without trichomes. These plants were genotyped for the presence of mutations at the CRISPR target site GL1 locus (AT3G27920) (TABLES 3A and 3B). Mutant plant genotypic verification was conducted using CAPS assays as described elsewhere (Curtin et al., *Plant Physiol* 156(2):466-473, 2011). Briefly, the target was PCR amplified using primers flanking the target site. Next, the fragments were digested using the Dde1 restriction enzyme. PCR amplicons resistant to digestion were submitted for Sanger Sequencing at the University of Minnesota Genotyping Center (UMGC) to confirm the presence of mutations. It is noted that a decrease in the number of trichomes or the complete absence of trichomes on the $T_1$ plants can result from somatic mutations, rather than germ line mutations, and thus further screening for mutations at the GL1 locus is required in the next generation.

TABLE 3A

Target Site and Methods for Genotypic Screening

| | |
|---|---|
| Endonuclease | CRISPR |
| Gene Target | AT3G27920 |
| Gene Target | Gl1 |
| Target sequence | GGAAAAGTTGTAGACTGAGATGG (SEQ ID NO: 16) |
| Mutant Phenotype | No trichomes or decreased trichrome density |
| Genotypic Screen | CAPS assay; enzyme *Dde1* |

TABLE 3B

PCR primers for amplifying CRISPR target site

| | |
|---|---|
| Gene Target | Gl1 |
| Forward Primer | 5'-GCACGTGTCACGAAAACCCATC-3' (SEQ ID NO: 17) |
| Reverse Primer | 5'-ATTGTAGTAACATAAAGTTATGTA-3' (SEQ ID NO: 18) |

Screening of $T_1$ plants for the CenH3 SNP: Individuals that had the GmCRISPR construct and lacked trichomes or had few trichomes were genotyped for the CenH3 SNP. The individuals were classified into the three genotypic classes based on the CenH3 SNP: homozygous wild type, heterozygous mutant, and homozygous mutant.

Selection of $T_1$ generation GmCRISPR plants to advance: Selections of $T_1$ plants to advance were made based on whether the plant had the GmCRISPR, lacked trichomes or had few trichomes, and was heterozygous for the CenH3 SNP. Thus, $T_1$ plants genotyped as homozygous wild type for the CenH3 SNP were not advanced. The $T_1$ plants heterozygous for the CenH3 SNP were advanced to maintain seed of the line. No $T_1$ plants were recovered that had the GmCRISPR, lacked trichomes, and were homozygous for the mutant CenH3 SNP.

Selection and advancement of $T_2$, $T_3$, and later generations of GmCRISPR plants: $T_2$ seeds from selected $T_1$ individuals were either directly seeded into the soil, or were surface sterilized, grown on ½ MS 0.8% agar media with 1% sucrose in petri dish plates and later transplanted to the soil. Twenty-one days after transplanting to the soil, the plants were screened for the presence of the GmCRISPR construct using Basta herbicide, as described above. Next, individuals were visually inspected for the absence of trichomes. Segregation ratios of 3:1 (trichomes:no trichomes) were observed, indicating that the GL1 mutation was in the germ line cells and that the mutation was heritable. At this stage, plants that lack trichomes were expected to result from a plant inheriting a pair of mutant gl1/gl1 alleles, rather than from a plant undergoing somatic mutations causing a gl1/gl1 phenotype. It is noted that the GmCRISPR also could cause new mutations.

The plants containing the GmCRISPR and lacking trichomes were genotyped for the CenH3 SNP. Individuals that were homozygous for the wild type CenH3 SNP (TABLE 4A: Classes 4 and 5) were not advanced. Individuals heterozygous for the CenH3 SNP (TABLE 4A: Classes 6 and 7) were advanced to maintain the plant line. Individuals homozygous for the CenH3 SNP (TABLE 4A: Classes 8 and 9) were selected for preliminary crosses to test the haploid induction and targeted mutagenesis system.

$T_3$ generation (and later) seeds from selected $T_2$ individuals were either directly seeded into the soil or are first surface sterilized, grown on ½ MS 0.8% agar media with 1% sucrose in petri dish plates, and later transplanted to the soil. Twenty-one days after transplanting to the soil, the plants were screened for the presence of the GmCRISPR construct using Basta herbicide sprays. Individual $T_{2:3}$ families were determined to be homozygous for the GmCRISPR construct if all individuals showed herbicide resistance (TABLE 4B: Classes 5, 7, and 9). Only individuals from families homozygous for the GmCRISPR construct were advanced. Next, individuals were visually inspected for the absence of trichomes to confirm that they were gl1/gl1. Plants containing the GmCRISPR and lacking trichomes were genotyped for the CenH3 SNP. Individuals identified as homozygous for the wild type CenH3 SNP (TABLE 4B: Classes 4 and 5) were not advanced, while individuals heterozygous for the CenH3 SNP (TABLE 4B: Classes 6 and 7) were advanced to maintain the plant line. Individuals homozygous for the CenH3 SNP (TABLE 4B: Class 9) were selected for crosses to test the haploid induction and targeted mutagenesis system.

TABLE 4A

List of Expected Genotypic Classes of $T_2$ Plants

| | | $T_2$ Individual Genotype | | | Selection Action | | | |
|---|---|---|---|---|---|---|---|---|
| Class | % likelihood | CRISPR | GL1 locus | CenH3 Locus | Basta Spray | Trichome Inspection | SNP Genotype | Advancement Decision |
| 1 | 25% | wt/wt | | | Die | | | |
| 2 | 37.5% | +/wt | GL1/— | | Survive | Fail | | |
| 3 | 18.75% | +/+ | GL1/— | | Survive | Fail | | |

TABLE 4A-continued

List of Expected Genotypic Classes of $T_2$ Plants

| | | $T_2$ Individual Genotype | | | Selection Action | | |
|---|---|---|---|---|---|---|---|
| Class | % likelihood | CRISPR | GL1 locus | CenH3 Locus | Basta Spray | Trichome Inspection | SNP Genotype | Advancement Decision |
| 4 | 3.125% | +/wt | gl1/gl1 | CenH3/CenH3 | Survive | Pass | Homo WT | Do not advance |
| 5 | 1.5625% | +/+ | gl1/gl1 | CenH3/CenH3 | Survive | Pass | Homo WT | Do not advance |
| 6 | 6.25% | +/wt | gl1/gl1 | CenH3/cenh3 | Survive | Pass | Het | Advance to $T_3$ |
| 7 | 3.125% | +/+ | gl1/gl1 | CenH3/cenh3 | Survive | Pass | Het | Advance to $T_3$ |
| 8 | 3.125% | +/wt | gl1/gl1 | cenh3/cenh3 | Survive | Pass | Homo mutant | Seed not fertile, recover genotype in $T_3$ from Class 6, could try to use for crossing |
| 9 | 1.5625% | +/+ | gl1/gl1 | cenh3/cenh3 | Survive | Pass | Homo mutant | Seed not fertile, recover genotype in $T_3$ from Class 7, could try to use for crossing |

TABLE 4B

List of Expected Genotypic Classes of $T_3$ Plants

| | $T_{2:3}$ Family | $T_3$ Individual Genotypes | | | Selection Action | | | |
|---|---|---|---|---|---|---|---|---|
| Class | Basta Spray Segregation | CRISPR | GL1 locus | CenH3 Locus | Basta Spray | Trichome Inspection | SNP Genotype | Advancement or Cross Decision |
| 4 | 3:1 live:die | +/wt | gl1/gl1 | CenH3/CenH3 | ¾ survive | Pass | Homo WT | Do not advance, originated from Class 6 |
| 5 | All survive | +/+ | gl1/gl1 | CenH3/CenH3 | all survive | Pass | Homo WT | Do not advance, originated from Class 7 |
| 6 | 3:1 live:die | +/wt | gl1/gl1 | CenH3/cenh3 | ¾ survive | Pass | Het | Do not advance if have Class 7 plant |
| 7 | All survive | +/+ | gl1/gl1 | CenH3/cenh3 | all survive | Pass | Het | Advance to maintain crossing line |
| 8 | 3:1 live:die | +/wt | gl1/gl1 | cenh3/cenh3 | ¾ survive | Pass | Homo mutant | Do not advance. Could use for crossing, but not preferred. |
| 9 | All survive | +/+ | gl1/gl1 | cenh3/cenh3 | all survive | Pass | Homo mutant | Use for crossing |

Phenotypic screening of seed from Cross Types #1, #2, and #3, Endonuclease target GL1: Crosses are conducted to test the effectiveness of combining a haploid inducer system with a CRISPR targeted mutagenesis system. Ravi and Chan (supra) found that using the haploid inducer as the female in a cross, rather than as the male, resulting in a higher percentage of haploids produced from the cross. Thus, for Cross Types #1 and #2, the plants used as the female in the haploid inducer cross are Col, (gl1/gl1), homozygous for the mutant CenH3 SNP, heterozygous or homozygous for the GmCRISPR transgene, homozygous for the GFP-TS-HFD transgene, and lacking a Kanamycin (KAN) resistance gene (TABLES 4A and 4B, Classes 8 and 9). Only 50% of the gametes produced from individuals heterozygous for the GmCRISPR will actually contain the GmCRISPR, while 100% of the gametes produced from individuals homozygous for the GmCRISPR will contain the GmCRISPR construct. Thus, it is preferred to cross with individuals homozygous for the GmCRISPR. For crosses conducted with $T_2$ plants, the genotype of the GmCRISPR is not determined; these crosses are conducted with heterozygous or homozygous GmCRISPR plants.

In Cross Type #1 (TABLE 5), Ler Gl1 Gl1 plants lacking a Kanamycin resistant gene are used as the male. In Cross Type #2 (TABLE 6), Ler Gl1 Gl1 plants that contain a Kanamycin resistance gene are used as the male. The presence of the Kanamycin resistance gene in Cross #2 allows for removal of any self-pollination derived seed when growing the seed from crosses on media containing Kanamycin. To test if the haploid induction and targeted mutagenesis can work using the haploid induce as the male of the cross, Cross Type #3 (TABLE 7) is conducted using the haploid inducer as the male and the Ler line, with or without Kanamycin resistance, as the female. It is noted that since the haploid inducer line is mostly male sterile, crossing it as the male may be difficult and result in a low success rate.

Seeds produced from the crosses are surface sterilized and then grown on ½ MS 0.8% agar media with 1% sucrose in petri dish plates. Cross Type #1 derived plants do not contain Kanamycin resistance and are thus not planted on media containing Kanamycin. In contrast, all seed produced from effective crosses from Cross Type #2 do contain the Kanamycin resistance gene and are planted on media containing 50 ng/ml Kanamycin. Any seed in Cross Type #2 that is produced from self-pollination does not have the Kanamycin resistance gene and are killed by the Kanamycin in the media. Cross Type #3 seeds are not plated on media containing Kanamycin. Progeny are phenotypically screened for the presence of trichomes 14-21 days after germination.

Five phenotypic classes are predicted to be present in the progeny of Cross Types #1, #2, and #3 (TABLES 5, 6, and 7, respectively). Seedlings from these crosses are screened for the presence of GL1 mutations and for the presence of haploidy. Individuals are visually screened for the absence of trichomes as a preliminary screen for successfully mutations at the GL1 locus (AT3G27920). To preliminarily screen for haploidy, individuals are visually assessed for growth and vigor, as diploid individuals grow much faster and larger than haploid individuals (Ravi and Chan, supra). Once identified, individuals without trichomes are transplanted to soil-containing pots and allowed to develop further. Individuals that show slower growth and are smaller also are transplanted to soil to develop further. Screening is conducted to identify individuals that are without trichomes and are smaller and grow more slowly, suggesting that they have been mutated and are haploid.

Individuals homozygous for the mutant CenH3 SNP are mostly male sterile (Ravi and Chan, supra), and thus the occurrence of self-pollination is predicted to be a rare event. Preliminary screening also showed that the few seed produced from homozygous mutant CenH3 SNP plants have low viability. Any individual produced from self-pollination in Cross Type #1 is gl1/gl1 diploid and can be screened out by their more vigorous growth as compared to haploid individuals. However, individuals that are produced from self-pollination in Cross Type #2 are killed by the Kanamycin in the media. Any individual produced from self-pollination in Cross Type #3 is GL1/GL1 and can be screened out by the presence of their trichomes. The number of individuals categorized into one of the five classes, as well as the number of ungerminated seed, are recorded to determine the percent efficacy of HILAGE.

TABLE 5

Expected genotypic classes from Cross Type #1:
Endonuclease target Gl1 (AT3G27920)

| Class | Haploid Identification Trait: Fast vs Slow Growing | Successful Mutation Trait: (no trichomes) | Phenotype indicates plant is: |
|---|---|---|---|
| A | Large plant, Fast growing | No trichomes | Self-pollination* |
| B | Large plant, Fast growing | Trichomes | Hybrid, not homozygous mutated |
| C | Large plant, Fast growing | No trichomes | Hybrid, mutated |
| D | Small plant, Slow growing** | Trichomes | Haploid***, not homozygous mutated |
| E | Small plant, Slow growing** | No trichomes | Haploid***, mutated |

Haploid inducer is used as the female plant. Ler plant is used as the male.
Ler⁺ male plant does not contain KAN resistance. Cross seed is planted on media without Kanamycin.
⁺Other wild type lines could be used as the male, but different SNP assays would need to be developed to differentiate between the specific wild type line and Col.
*Since the haploid inducer line is mostly male sterile, self-pollination is an unlikely event.
**Haploid individuals often are smaller and grow more slowly than diploid individuals (Ravi and Chan, supra).
***Some slow growing plants may be aneuploid rather than fully haploid. Haploid individuals can be distinguished from aneuploid individuals through genotypic analysis.

TABLE 6

Expected genotypic classes from Cross Type #2:
Endonucleases target Gl1 (AT3G27920)

| Class | Haploid Identification Trait: Fast vs Slow Growing | Successful Mutation Trait: (no trichomes) | Phenotype indicates plant is: |
|---|---|---|---|
| A | na | na | Any self-pollinated* seeds are killed by Kanamycin. Female in cross does not have a Kanamycin resistance gene. |
| B | Large plant, Fast growing | Trichomes | Hybrid, not homozygous mutated |
| C | Large plant, Fast growing | No trichomes | Hybrid, mutated |
| D | Small plant, Slow growing** | Trichomes | Haploid***, not homozygous mutated |
| E | Small plant, Slow growing** | No trichomes | Haploid***, mutated |

Haploid inducer is used as the female plant. Ler plant is used as the male.
Ler male plant does contain KAN resistance. Cross seed is planted on Kanamycin containing media.
*Since the haploid inducer line is mostly male sterile, thus self-pollination is an unlikely event. The use of Kanamycin in the media prevents this class of plant from germinating.
**Haploid individuals often are smaller and grow more slowly than diploid individuals (Ravi and Chan, supra).
***Some slow growing plants may be aneuploid rather than fully haploid. Haploid individuals can be distinguished from aneuploid individuals through genotypic analysis.

TABLE 7

Expected genotypic classes from Cross Type #3:
Endonucleases target Gl1 (AT3G27920)

| Class | Haploid Identification Trait: Fast vs Slow Growing | Successful Mutation Trait: (no trichomes) | Phenotype indicates plant is: |
|---|---|---|---|
| A | Large plant, Fast growing | Trichomes | Self-pollination |
| B | Large plant, Fast growing | Trichomes | Hybrid, not homozygous mutated |
| C | Large plant, Fast growing | No trichomes | Hybrid, is mutated |
| D | Small plant, Slow growing* | Trichomes | Haploid**, not homozygous mutated |
| E | Small plant, Slow growing* | No trichomes | Haploid**, is mutated |

Ler plant is used as the female plant. Haploid induced plant is used as the male.
Ler⁺ female plant does or does not contain a KAN resistance gene. Seed is planted on normal media.
⁺Other wild type lines could be used as the male, but different SNP assays would need to be developed to differentiate between the additional wild type line and Col.
*Haploid individuals often are smaller and grow more slowly than diploid individuals (Ravi and Chan, supra).
**Some slow growing plants may be aneuploid rather than fully haploid. Haploid individuals can be distinguished from aneuploid individuals through genotypic analysis.

Genotypic screening of seed from Cross Types #1, #2, and #3, Endonuclease target: GL1: After phenotypic screening, the individuals of Cross Types #1, #2, and #3 that lack trichomes are genotypically screened to confirm the presence of a mutation at the Gl1 locus (AT3G27920) as previously described. The GL1 CRISPR target site of all individuals in Class E (TABLES 5, 6, and 7), as well as a subset of the Class C individuals, are sequenced to confirm the presence of a mutation.

Genotyping individuals to confirm haploidization: Individuals from Class E (TABLES 5, 6, and 7) and a set of Ler and Col diploid control plants are genotyped using a custom SNP chip assay to test the haploid, aneuploid, or diploid state of these individuals. The SNP assay is designed to test SNPs identified as polymorphic between Col and Ler at multiple loci across the five chromosomes of *Arabidopsis*.

Aneuploid individuals appear genotypically heterozygous for Col and Ler at one or more SNP positions, while $F_1$ plants appear heterozygous at all SNP positions, and haploid plants have the Ler genotype at all positions. Additionally, whole genome sequencing is utilized to confirm the haploid state of select mutated haploid individuals.

Flow cytometry to confirm the occurrence of haploid individuals: Flow cytometry also is conducted to confirm the presence of haploid individuals. All individuals that are trichomeless and suspected to be haploid are tested with flow cytometry. Some individuals that have trichomes and are suspected to be haploid, as well as some known diploid individuals (as controls) also are tested using flow cytometry.

Growing of haploid individuals and treatment of plants with colchicine to double chromosome numbers: Haploid individuals that are identified as homozygous Ler and also have a mutation at the target locus are chromosome doubled using colchicine before bolting, following methods described elsewhere (Ravi and Chan, supra). These individuals are grown up in conditions described elsewhere, and seed is harvested.

Example 2—HILAGE: Maize

Haploid inducer methods: Maize (*Zea maize*) HILAGE method is being conducted using the standard maize in vivo haploid induction using a cross with a haploid inducer line, haploid identification techniques, and subsequent chromosome doubling techniques such as, but not limited to, those described by Prigge and Melchinger ("Production of Haploids and Doubled Haploids," in *Maize Plant Cell Culture Protocols, Methods in Molecular Biology*, Volume 877, pp. 161-172, 2012) and others. Briefly, the in vivo technique of maize haploid induction first requires that a cross be made between the line to be induced and the haploid inducer line. The inducer is used as either the male or as the female of the cross. In HILAGE-based methods, the haploid inducer is likely used as the female, but alternatively, HILAGE-based methods are conducted using the haploid inducer as the male. Usually, the haploid inducer has a dominant purple pigment gene (e.g., R1-nj) that is used to assist in identifying seeds that are haploid. The seeds of haploid individuals have a purple aleurone, but lack purple pigment in the endosperm (scutellum), indicating that the germline does not contain the haploid inducer chromosomes. Seeds that have a yellow endosperm and a purple aleurone are planted out and grown up to be seedlings. These seedlings have their chromosome number doubled using colchicine or other methods. The chromosome doubled haploids are grown in a greenhouse and or transplanted to the field, and the chromosome doubled plants are self-pollinated to produce doubled haploid seed.

Endonuclease transgene and transgenic construct: Maize HILAGE adds the targeted mutagenesis component to the in vivo haploid induction system and thus requires an endonuclease. Examples of useful endonucleases include, without limitation meganucleases, ZFNs, TALE nucleases, and CRISPR/Cas-based nucleases. The endonuclease is designed to target Bm3, but an endonuclease can be designed to target nearly any sequence. The endonuclease(s) are constructed using methods such as, but not limited to, those described by Sander et al. (*Nature Met* 8(1):67-69, 2011), Cermak et al. (*Nucl Acids Res* 39(17):7879, 2011; with correction at *Nucl Acids Res* 39:e82. doi: 10.1093/nar/gkr218, 2011), and Liang et al. (*J Genet Genom* 41(2):63-68, 2014). An AdH1 intron1 or an HSp70 intron is included in the non-translated leader of the endonuclease gene (U.S. Pat. No. 5,593,874) in order to increase gene expression. The promoter used to drive expression of the endonuclease is expressed during early embryo development, and can be endogenous or exogenous. Examples are provided in TABLE 8.

TABLE 8

| Examples of promoters |
| --- |
| 35S (CaMV d35S) or derivatives (e.g., double 35S) |
| ZmUb1 (maize) |
| APX (rice) |
| OsCc1 (rice) |
| EIF5 (rice) |
| R1G1B (rice) |
| PGD1 (rice) |
| Act1 (rice) |
| SCP1 (rice) |

A method for testing potential promoters for driving endonuclease expression includes the following steps:
 1. Develop an endonuclease that targets a gene required to make anthocyanin/purple pigment (e.g., the R1-nj gene).
 2. Test different promoters in front of the endonuclease coding sequence, and generate transgenic plants containing the endonuclease coding sequence linked to the various promoters.
 3. Pollinate the transgenic endonuclease-containing plant with a plant having the purple pigment gene (dominant natural trait; do not use haploid inducers for this test).
 4. Determine whether different promoter-endonuclease combinations result in fewer or more seeds that do not develop purple endosperm.
 5. Replicate the same promoter across several transgenic events to control for positional effects of the transgene in the genome.
 6. Select promoters that result in a high proportion of $F_1$ kernels that are lack a purple endosperm, meaning that the mutation(s) happened early in the development of the endosperm in all of the developing endosperm cells.
 7. Alternatively, the test can be done using a haploid inducer that does not contain a purple pigment gene but does contain the endonuclease. Cross the haploid inducer to a line with a purple pigment gene targeted by the endonuclease. Determine whether any of the seeds have a purple aleurone (indicating a cross rather than a self-pollination) and lack a purple endosperm. Plant out seeds having a purple aleurone and lacking a purple endosperm, and determine whether any of these individuals are haploid.

The endonuclease construct may include a selectable marker (e.g., herbicide resistance) to assist with recovery of the transgene during whole plant transformation and subsequent backcrossing, although a selectable marker is not required for HILAGE-based methods. In some cases, one or more (e.g., two or more, or three or more) endonucleases and/or CRISPR guide RNAs are combined into a single construct to target one or sequences of DNA.

Introgression of the endonuclease transgene into the haploid inducer: The next step in maize HILAGE-based methods is the addition of a transgenic endonuclease gene to the maize haploid inducer line. The endonuclease transgene is added to the haploid inducer line using, e.g., direct transformation via an *Agrobacterium*-based method (such as the method described by Ishida et al., *Nature Biotechnol* 14(6): 745-750, 1996) or particle bombardment (such as the method described by Gordon-Kamn et al., *Plant Cell Online* 2(7):603-618, 1990). Alternatively, a line amenable to transformation is first transformed with the endonuclease transgene, and the resulting line is then crossed to a haploid inducer line. $F_1$ diploid progeny are screened from this cross, and these individuals may be backcrossed to the haploid inducer line. This backcrossing process is repeated several times to recover the majority of the haploid inducer's genetics with the addition of the endonuclease transgene. After a sufficient number (e.g., two, three, or four) of backcrosses are completed, the resulting backcross plant (e.g., $BC_3F_1$) plant is self-pollinated to produce $BC_3F_2$ individuals. These individuals are screened to find individuals that are genetically very similar to the haploid inducer line and are homozygous for the endonuclease transgene(s). In the second method, molecular markers may be used to select backcross individuals that contain the transgene and high percentages of the haploid inducer genome. Selected individuals can be used for the next round of backcrossing to more quickly recover the genome of the haploid inducer with the addition of the endonuclease transgene(s). The resulting line that functions as a haploid inducer line and contains the endonuclease transgene is the haploid inducer stock line.

Testing expression of the endonuclease transgene: Following either direct transformation or transformation of another line followed by backcrossing, several tests are run on the expression of the endonuclease in the haploid inducer stock line. Alternatively, expression tests are conducted before or concurrently with the backcrossing to select transgenic events with high expression. Specifically, expression assays for RNA and protein expressed from the endonuclease transgene are conducted to ensure that the transgene is correctly expressed. Transformation events with higher expression are desired for HILAGE-based methods. Efficacy of the transgene transformation event can additionally be assessed by determining if mutations are detected in the target site(s) of the line. The presence of mutations is evaluated as described above for *Arabidopsis*. Events with high gene expression and the presence of mutations in the target site(s) can be outcrossed to targeted lines to determine whether haploid progeny with mutations are generated. Desirable haploid inducer-transgenic event combinations produce a high frequency and number of haploid progeny with targeted mutations.

Utilization of Maize HILAGE: The haploid inducer is crossed (either as the male or female) to a targeted line to generate haploid progeny. It is noted, however, that if the promoter(s) used in the endonuclease construct result in endonuclease expression before fertilization (as well as during the first couple of cell divisions), the haploid inducer stock line is used as the female. By using the haloid inducer as the female, if the endonuclease is expressed in the egg before pollination and during the first stages of cell development, the endonuclease can immediately begin mutating the target sequence upon pollination and continue mutating the target sequence before the haploid inducer genome is lost from the cell. In the first stages of mitosis, before the haploid inducer genome is eliminated, the targeted endonuclease induces targeted DNA double strand breaks in the DNA from the maize line. Some of these double stranded breaks are incorrectly repaired and a mutation results. The haploid progeny genomes are doubled before or after the progeny are screened for the mutation(s). Once the genomes of these haploid individuals are doubled, the individuals are grown out and self-pollinated to produce doubled haploid seed. Different mutations may be produced, and evaluation of each mutation event is necessary to determine if the mutation(s) obtained have the desired result. Mutations that produce a desired phenotype are referred to herein as "effective mutations" (EM). Only lines with EM are advanced.

HILAGE-based methods may be conducted on all (or many) of the maize lines that a breeder plans to use as parents for breeding. If a breeder develops populations using lines that have an EM at all targeted loci, the populations do not segregate for the EM. Thus, the breeding efforts are simplified by not having to select for the presence of the EM.

If the haploid inducer stock line is used as the female, the resulting haploid and doubled haploid will inherit the cytoplasm from the haploid inducer's stock line. If the haploid inducer stock line's cytoplasm is desirable, the resulting inbred will inherit the desirable cytoplasm. If, however, the line's own cytoplasm is desired and if the haploid inducer is used as the female in HILAGE-based methods, then the resulting doubled haploid with targeted mutations can be backcrossed as the male to the original line to recover the original cytoplasm. The $F_2$ progeny of the cross shares the same cytoplasm and background genetics, but differs at the one or multiple targeted mutation loci. Selection can be conducted among the $BC_1F_2$ individuals to identify individuals homozygous at the desired target loci.

Exemplary target sites and methods for genotypic screening in maize are provided in TABLES 9A and 10A, while exemplary primers for amplifying the target sites are provided in TABLES 9B and 10B. Expected genotypic classes from the crosses for the two targets are shown in TABLES 11 and 12.

Advantages of Maize HILAGE-based methods can include:
1. The method produces doubled haploid individuals with the targeted mutation(s) in less than 1 year (using winter nurseries), without the expense of backcrossing in a desired targeted mutation into the targeted line.
2. Backcrossing is needed to put the endonuclease transgene into the haploid inducer line, but no subsequent backcross procedures are required to induce mutations into tens, hundreds, or even thousands of elite lines (assuming the inducer stock line is used as the male or assuming the cytoplasm of the inducer stock line is acceptable).
3. If two or more targeted mutations are desired, multiple endonuclease transgenes may be placed into the inducer line.
4. If multiple mutations are desired, the recovered doubled haploid individuals may not have all of the desired mutations. Doubled Haploid progeny with single mutations can be crossed together, and the $F_2$ progeny can be screened for individuals that are homozygous for all desired mutations.
5. If the inducer is used as the male, the recovered progeny will have the cytoplasm of the targeted line. If the cytoplasm of the inducer is desired (for example to obtain male sterile cytoplasm), the haploid induce can be used as the female. If the cytoplasm of the targeted line is desired, crosses can be made between the non-mutated version of the targeted line (as the female) and the mutated version of the targeted line (as the male).
6. As stated above, the cells in the first stages of mitosis (before the haploid genome is removed) may try to repair the DSB in the targeted line's chromosome by HR using the haploid inducer stock line's chromosome as the template DNA strand. However, it is likely that the haploid inducer's gene will already have been mutated by the endonuclease. Thus, if HR occurs, the cell will 'repair' the break incorrectly by using the mutated inducer stock line's DNA as the template, and a mutation will occur in the targeted line's DNA. Potentially, if HR occurs in this way, specific mutations can be induced in the targeted line.

7. HILAGE-based methods may be useful for transgene insertion without backcrossing. Transgenes can be introduced into a DSB if the provided template contains the transgene flanked by sequences that are homologous to the sequences on either side of the DSB (see, Shukla et al., Nature 459:437-441, 2009). In HILAGE-based methods, a transgenic event (e.g., to insert an herbicide gene) approved by the USDA is backcrossed into the haploid inducer line. An endonuclease gene is used to target the relative position of the transgene in a non-transgenic line. (In a line homozygous for the herbicide gene, the endonuclease would effectively do nothing.) The transgenic event to be inserted needs to be flanked on both sides by DNA sequences homologous to the DNA flanking the target site. When the haploid inducer is crossed to a targeted line that does not have the herbicide gene (and thus has the targeted site) the endonuclease will cause a double strand break at the target site. If the targeted line's DNA is repaired by HR using the haploid inducer stock line's DNA (and transgene) as the template, the targeted line DNA "repairs" the double strand break by putting the transgene sequence in the double strand break site. Thus, HILAGE-based methods may be used to place transgenes into targeted lines without having to backcross. Assuming the sequence surrounding the transgene is exactly the same as the sequence surrounding the transgenic event certified by the USDA, the two events are arguably substantially equivalent.

Maize gene to target—Bm3 ZEAMMB73_595664: Sequences of the target oligonucleotides were as follows (with f1/r1 for target 1 and f2/r2 for target 2):

```
Maize Bm3 gene (ZEAMMB73_595664)
                                      (SEQ ID NO: 19)
f1 5' GATTGGGCTCCACCGCCGGCGACG 3'

(SEQ ID NO: 20)
r1 5' AAACCGTCGCCGGCGGTGGAGCCC 3'

(SEQ ID NO: 21)
f2 5' GATTGAACCAGGACAAGGTCCTCA 3'

(SEQ ID NO: 22)
r2 5' AAACTGAGGACCTTGTCCTGGTTC 3'
```

Underlining indicates the 20 bp target sequences.

TABLE 9A

Target Site and Methods for Genotypic Screening, Target 1

| | |
|---|---|
| Endonuclease | CRISPR |
| Gene Target | ZEAMMB73_595664 |
| Gene Target | Maize *Bm3* |
| Target sequence | GGGCTCCACCGCCGGCGACGTGG (SEQ ID NO: 23) |
| Mutant Phenotype | Brown Midrib |
| Genotypic Screen | CAPS assay; enzymes BmgB Iand *MreI* |

TABLE 9B

PCR primers for amplifying CRISPR target site, Target 1

| | |
|---|---|
| Gene Target | Maize *Bm3* |
| Forward Primer | 5'-CACGGTGCTTGAATTAGTGCG-3' (SEQ ID NO: 24) |
| Reverse Primer | 5'-GGTCCCTCCATCTGGCACCG-3' (SEQ ID NO: 25) |

TABLE 10A

Target Site and Methods for Genotypic Screening, Target 2

| | |
|---|---|
| Endonuclease | CRISPR |
| Gene Target | ZEAMMB73_595664 |
| Gene Target | Maize *Bm3* gene |
| Target sequence | GAACCAGGACAAGGTCCTCATGG (SEQ ID NO: 26) |
| Mutant Phenotype | Brown Midrib |
| Genotypic Screen | CAPS assay; enzyme DrdII, BstNI, and PpuMI |

TABLE 10B

PCR primers for amplifying CRISPR target site, Target 2

| | |
|---|---|
| Gene Target | Maize Bm3 |
| Forward Primer | 5'-GGTGGTGGACGAGGAGGC-3' (SEQ ID NO: 27) |
| Reverse Primer | 5'-GTAGCACCAATGATGAGCGAG-3' (SEQ ID NO: 28) |

TABLE 11

Expected genotypic classes from cross: Bm3 endonuclease target (ZEAMMB73_595664) Haploid inducer stock line is the female and has the purple pigment trait (R1-nj), and is crossed to a line without the purple pigment trait (see, Brink and Williams, *Genet* 73(2):273-296, 1973). Haploid seeds are identified by color traits; seeds that are not haploid are readily discarded by visual identification. Only seeds of classes D and E are planted out.

| Class | Haploid Identification Trait: Seed color | Successful Mutation Trait: (brown midrib) | Phenotype indicates plant is: |
|---|---|---|---|
| A | Purple aleurone, Purple scutellum | Green Midrib | Self-pollination |
| B | Purple aleuron, Purple scutellum | Green Midrib | Hybrid, not homozygous mutated |
| C | Purple aleuron, Purple scutellum | Brown Midrib | Hybrid, is mutated |
| D | Purple aleuron, Yellow scutellum* | Green Midrib | Haploid*, not homozygous mutated |

TABLE 11-continued

Expected genotypic classes from cross:
Bm3 endonuclease target (ZEAMMB73_595664)
Haploid inducer stock line is the female and has the purple
pigment trait (R1-nj), and is crossed to a line without
the purple pigment trait (see, Brink and Williams, *Genet*
73(2):273-296, 1973). Haploid seeds are identified by color
traits; seeds that are not haploid are readily discarded by
visual identification. Only seeds of classes D and E are
planted out.

| Class | Haploid Identification Trait: Seed color | Successful Mutation Trait: (brown midrib) | Phenotype indicates plant is: |
|---|---|---|---|
| E | Purple aleuron, Yellow scutellum* | Brown Midrib | Haploid*, is mutated |

*The seeds of haploid individuals have a purple aleurone but lack purple pigment in the endosperm (scutellum), indicating that the germline does not contain the haploid inducer chromosomes.

TABLE 12

Expected genotypic classes from cross:
Bm3 endonuclease target (ZEAMMB73_595664)
Haploid inducer stock line is the male and has the purple
pigment trait (R1-nj), and is crossed to a line without the
purple pigment trait (Brink and Williams, *supra*). Haploid seeds
are identified by color; only seed classes D and E are planted out.

| Class | Haploid Identification Trait: Seed color | Successful Mutation Trait: (brown midrib) | Phenotype indicates plant is: |
|---|---|---|---|
| A | Yellow aleurone, Yellow scutellum | Green Midrib | Self-pollination |
| B | Purple aleuron, Purple scutellum | Green Midrib | Hybrid, not homozygous mutated |
| C | Purple aleuron, Purple scutellum | Brown Midrib | Hybrid, is mutated |
| D | Purple aleuron, Yellow scutellum* | Green Midrib | Haploid*, not homozygous mutated |
| E | Purple aleuron, Yellow scutellum* | Brown Midrib | Haploid*, is mutated |

*The seeds of haploid individuals have a purple aleurone but lack purple pigment in the endosperm (scutellum), indicating that the germline does not contain haploid inducer chromosomes.

```
Maize Bm3 and surrounding sequence on chromosome 4 (exons are underlined and in
uppercase):
                                                                  (SEQ ID NO: 29)
gtcatggatggagccagtgaactgatgatttttccccaccccgcacgcaacagcatgggtgacaacaaccactcccgctgcgg ttgggcgagcacatctctacgcacttgacactcacgcaaacctaacgcatactagattaatcatcgccaccaactatcggcgaca gaaacgatgggccccgcttctataatcacggtgatgaattagtgcgcgcatagtagtgaaaaataatagtgaaaaataagcagt gcgtgttttggtgtggtggttggtgagccgtccggcccaataaaaaccctcgcaccacctcgtccctcttcgtcgcatcgcacgc catcagcagctagcgcgctcctcgagcccagcagagaaaggccggcctacccactctctctctctctctccagtctccaccg gcagcgctaatcgtaatagccATGGGCTCCACCGCCGGCGACGTGGCCGCGGTGGTGGAC

GAGGAGGCGTGCATGTACGCGATGCAGCTGGCGTCGTCGTCCATCCTGCCCA

TGACGCTGAAGAACGCCATCGAGCTGGGCCTGCTGGAGGTGCTGCAGAAGGA

GGCCGGCGGCGGCAAGGCGGCGCTGGCGCCCGAGGAGGTGGTGGCGCGGAT

GCCCGCGGCGCCCGGCGACCCCGCCGCCGCGGCGGCCATGGTGGACCGCATG

CTCCGCCTGCTCGCCTCCTACGACGTCGTCCGGTGCCAGATGGAGGACCGGG

ACGGCCGGTACGAGCGCCGCTACTCCGCCGCGCCCGTCTGCAAGTGGCTCAC

CCCCAACGAGGACGGCGTGTCCATGGCCGCCCTCGCGCTCATGAACCAGGAC

AAGGTCCTCATGGAGAGCTGgtgagtagtagccgcatcgcatcaaccaccttctacctatctatatccatcactt gttgctgctggcgtgcgcggcatgcatgatgacgagctcgctcatcattggtgc-
tactagtgatttatttcgtccagtaaaattaatta aggtgcgctgctactctactggctgcggctagcacaaggctggaaatagttgttacttgt-
tatacacgatataatatttctctagaac aaaaaagatttttttttttataaaaagcaagcaagaaagaaagtgagtgactt-
catgttttcctaaaaaaaagttaggagtgggatgg aaaagtcagcaaggaccacttgtttgttgtccactatccatccagtgggtga-
gactttttttgcgagacggagcactatattattggcc gagtcctttttctgtatccgcaaaacggcagccgtcgatcgccggacggatcgacggctcacatgagtgtcgagtccaattccaa ccacgagggcggcaaggaaaaccatccgtgctggtctggacttttttgccaaactccattcagccattcgccgactgaaggtgaat cttcagacagccagattgtttggtgtctagtgtgtgcgaagatggcgtagaaaagactgagagacagttggctcacacagacaa
-
```

-continued

```
gtgacaactgactatagtatctgcctgcctggctgatgctgatagagatggggac-
tatgtcctgtctgtttcttgtatgcgctgatct gattctgatcactgccactctgccagGTACTATCTCAAGGACGCGGTGCTGGACGGCGGCAT

CCCGTTCAACAAGGCGTACGGGATGACGGCGTTCGAGTACCACGGCACGGAC

TCGCGCTTCAACCGCGTGTTCAACGAGGGCATGAAGAACCACTCGGTGATCA

TCACCAAGAAGCTGCTGGACTTCTACACGGGCTTCGAGGGCGTGTCGACGCT

GGTGGACGTGGGCGGCGGCGTGGGCGCCACGCTGCACGCCATCACGTCCCGC

CACCCGCACATCTCCGGGGTCAACTTCGACCTGCCGCACGTCATCTCCGAGG

CGCCGCCGTTCCCCGGCGTGCGCCACGTGGGCGGGGACATGTTCGCGTCCGT

GCCCGCCGGCGACGCCATCCTCATGAAGTGGATCCTCCACGACTGGAGCGAC

GCGCACTGCGCCACGCTGCTCAAGAACTGCTACGACGCGCTGCCGGAAAATG

GCAAGGTCATCGTCGTCGAGTGCGTGCTGCCGGTCAACACGGAGGCCACCCC

CAAGGCGCAGGGCGTCTTCCACGTCGACATGATCATGCTCGCGCACAACCCC

GGCGGCAAGGAGCGGTACGAGCGCGAGTTCCGCGAGCTCGCAAAGGGCGCC

GGCTTCTCCGGGTTCAAGGCCACCTACATCTACGCCAACGCCTGGGCCATCG

AGTTCATCAAGTGAaccaccgtcgccgcgatgagatggcatggctgccacatgctttgcttgcttggtcctcgtatc gtacgtcgccgtcgtcgtatatctggttattgcgctgctacctcgctgctctcgcgtatgcatgtactttgcttaatttt ctttcttcatatcatgcactctggctggcctagac
```

Example 3—HILAGE: Wheat

Haploid inducer methods: A wheat (*Triticum aestivum* or *Triticum durum*) HILAGE-based method is conducted using the standard wheat in vivo haploid induction using a cross with a maize pollen to pollinate an emasculated wheat spike, embryo rescue in tissue culture, and subsequent chromosome doubling techniques such as, but not limited to, those described by Knox et al. (*Plant Breeding* 119:289-298, 2000) and Inagaki ("Double haploid production in wheat through wide hybridization," in *Double Haploid Production in Crop Plants: A Manual*, Maluszynski, Kasha, Forster and Szarejko (Eds.), pp. 53-58, Kluwer Academic Publishers, Dordrecht, Netherlands, 2003). Briefly, the in vivo technique of wheat haploid induction first requires that an emasculated wheat spike. The following day, the emasculated wheat spike is pollinated with maize pollen. On days 3 and 4 after emasculation the spike is treated with 2, 4-dinitrophenylhydrazone or Dicamba (3,6-dichloro-2-methoxybenzoic acid) (Knox et al., supra). Then about 16-19 days after pollination, the developing wheat embryos are removed from the spike and transferred to tissue culture. The developing embryo is grown in tissue culture into a plantlet. The plant is eventually transplanted to the greenhouse, treated with colchicine to double the chromosome number and doubled haploid seed is harvested.

Alternatively, wheat haploid induction can be induced using sorghum, millet, barley (*H. bulbosum*), or teosinte pollen. The below procedure will describe the use of maize as the haploid inducer, but maize could alternatively be substituted for sorghum, millet, barley (*H. bulbosum*), or teosinte.

Endonuclease transgene and transgenic construct: The wheat HILAGE-based method adds the targeted mutagenesis component to the in vivo haploid induction system and thus requires an endonuclease. In wheat HILAGE, one or more of the maize chromosome(s) are carrying an endonuclease transgene capable of causing targeted double strand breaks in the wheat genome. Useful endonucleases include, without limitation, meganucleases, ZFNs, TALE nucleases, and CRISPR/Cas-based endonucleases. The endonuclease is designed to target Tsn1, but an endonuclease can be designed to target nearly any sequence. The endonuclease(s) are constructed using methods such as, but not limited to, those described by Sander et al. (supra), Cermak et al. (supra), and Liang et al. (supra). The promoter used to drive expression of the endonuclease can be endogenous or exogenous. High expression of the endonuclease is essential to increase the chance that a targeted mutation is successful before the removal of the maize chromosomes carrying the endonuclease transgene. Suitable promoters are expressed during early embryo development, and can be endogenous or exogenous. Examples are provided in TABLE 8.

The endonuclease construct may include a selectable marker, such as an herbicide resistance gene, to assist in recovery of the transgene during whole plant transformation and subsequent backcrossing. When included, the herbicide resistance selectable marker is operably linked to a promoter with strong expression in maize and/or wheat.

In some cases, the transgenic construct containing the endonuclease or a second construct combined into the same maize line contains one or more copies of a sequence of DNA having homology to the DNA at and flanking the target site. This sequence of DNA may contain nucleotide changes such as one or more base pair substitutions and/or deletions and/or additions. Alternatively, this sequence may contain a gene, a promoter, a regulatory sequence, and/or a transgene.

Testing the endonuclease in transgenic wheat: While HILAGE-based methods do not use a transgenic wheat line to generate the final product of doubled haploid wheat with targeted mutations, it may be beneficial, though not necessary, to test the efficacy of the targeted endonuclease construct in a transgenic wheat line. Wheat transformation could be conducted following techniques such as, but not limited to, those describe by Weeks et al. (*Plant Physiol* 102(4): 1077-1084, 1993) and Cheng et al. (*Plant Physiol* 115(3): 971-980, 1997). Transgenic wheat with putative mutations could be checked for targeted mutations using methods similar to those described in the *Arabidopsis* section. An endonuclease with efficacy at causing double stranded breaks should be utilized for wheat HILAGE-based methods.

Generating a maize line to use for wheat HILAGE: One major difference between wheat HILAGE-based methods and normal doubled haploid creation in wheat is that a transgenic maize line is being used for haploid induction instead of a conventional maize line. As such, a maize line is being transformed with the endonuclease construct. The endonuclease transgene could be added to the haploid inducer using several methods such as, but not limited to: agrobacteria methods (such as those described by Ishida et al., supra) or by particle bombardment (such as the method described by Gordon-Kamm et al., supra). Since the line used for maize transformation likely is not a prolific haploid inducer, it may be beneficial, though not necessary, to backcross the endonuclease transgene(s) into a genetic background which has shown high efficacy in wheat haploid induction. The backcross introgression of the transgene into a more suitable maize line could be conducted with the assistance of molecular markers to select for the presence of the endonuclease transgene as well as to select for the genetic background of the recurrent parent (the suitable maize line) and against the donor parent line (the originally transformed maize line).

Depending on the promoter chosen to drive the endonuclease, the endonuclease is likely to show different expression in the maize line than in the progeny of the maize-wheat cross. If the gene is expected to express in maize, it may be beneficial to assess RNA and protein expression of the endonuclease to confirm that the endonuclease is functional.

Genotyping of the mutated wheat plants: The plantlets are genotyped before or after transplanting to soil to identify (1) if the desired targeted mutation(s) occurred, (2) if the wheat plant no longer contains maize chromosomes, and (3) if the transgene(s) are no longer present. Additionally, potentially different tillers may need to be genotyped as the plant could be chimeric for one or more targeted mutations. Checking for mutation(s) at the target site(s) can be conducted as previously described in the *Arabidopsis* section. The presence of maize chromosomes, could be assessed by one or more of several methods. Primers can be designed to amplify specific sequences on each of the 10 maize chromosomes in the maize line used for haploid induction, and these primers can be used to determine if the maize chromosomes are still present. Alternatively, a custom SNP chip can be designed that can be used to genotyped the wheat line and also maize DNA. In wheat plants that have lost the maize chromosomes, the wheat SNPs are able to be genotyped, but the maize SNPs are not able to be genotyped. Alternatively or additionally, a low coverage whole genome sequencing method or RNA sequencing method could be utilized to determine if the maize chromosomes are present and/or maize genes are being expressed. If the maize chromosomes have been removed from the wheat plant, it is likely that the transgene had also been removed. However, to increase industry and consumer acceptance of HILAGE, it may be beneficial to test for the absence of the transgene(s) in the wheat line. In one method, primers that amplify portions or all of the transgenic construct can be designed and used to test if any portion of the construct is in the produced wheat line. Alternatively, the sequences of the transgene can be search for in whole genome sequence or RNA sequence data, if said data are available.

Utilization of Wheat HILAGE: The maize line containing one or more endonuclease and or CRISPR guide RNAs is being crossed (as the pollen donor) to a wheat line to generate haploid progeny. Before the maize chromosomes are eliminated, the targeted endonuclease induces targeted DNA double strand breaks in the DNA from the wheat line. Some of these double stranded breaks will be incorrectly repaired and a mutation will result. The haploid progeny genomes can be doubled before or after the progeny are screened for the mutation(s). Once the genomes of these haploid individuals are doubled the individuals can be grown out and self-pollinated to produce doubled haploid seed. Different mutations may be produced, and evaluation of each mutation event is necessary to determine if it has the desired result. Only lines with EM, which produce a desired phenotype (e.g., mutations that cause a frame shift and eliminate proper gene function), are advanced.

In some cases, HILAGE-based methods are conducted on all (or many) of the wheat lines that are to be used as parents for breeding. If populations are developed using lines that have an EM at all targeted loci, the populations will not segregate for the EM. Thus, breeding efforts are simplified by not having to conduct selections for the presence of the EM.

Advantages of HILAGE in Wheat: HILAGE could play a pivotal role in generating targeted mutations in wheat. Globally, there is still resistance to utilizing transgenes in wheat. HILAGE could provide a method to induce targeted mutations in wheat without the released wheat line ever technically coming in contact with a transgene placed into a wheat chromosome.

HILAGE-based methods may be more effective in wheat than in maize since it is likely that the maize chromosomes persist longer in the maize-wheat embryo than the haploid inducer maize chromosomes persist in the maize haploid inducer-regular maize line embryo. The additional time that the maize chromosomes are residing in the wheat embryo, the more opportunity for targeted mutations to occur.

Exemplary target sites and methods for genotypic screening in wheat are provided in TABLE 13A, while exemplary primers for amplifying the target site are provided in TABLE 13B. Expected genotypic classes from the cross are shown in TABLE 14.

Wheat gene to target—Tsn1: Sequences of the target oligonucleotides were as follows (with f1/r1 being for target 1 and f2/r2 being for target 2).

```
Tsn1 gene
                                    (SEQ ID NO: 30)
    f1 5' GATTGCCGCTAGGGCATCTTAGAT 3'

(SEQ ID NO: 31)
    r1 5' AAACATCTAAGATGCCCTAGCGGC 3'
```

Underlining indicates the 20 bp target sequences.

TABLE 13A

Target Site and Methods for Genotypic Screening, Target 1

| | |
|---|---|
| Endonuclease | CRISPR |
| Gene Target | Wheat *Tsn1* |
| Gene Target | ADH59425 |

TABLE 13A -continued

Target Site and Methods for Genotypic Screening, Target 1

| | |
|---|---|
| Target sequence | GCCGCTAGGGCATCTTAGATAGG (SEQ ID NO: 32) |
| Mutant Phenotype | Resistance to *Stagonospora nodorum*, which causes *Stagonospora nodorum* blotch (SNB); and resistance to *Pyrenophora tritici-repentis*, which causes tan spot.* |
| Genotypic Screen | CAPS assay; enzymes SfaNI, DdeI, BglI, TauI, and AciI |

*Faris et al, *Proc. Natl. Acad. Sci. U.S.A.* 107(30): 544-13549, 2010.

TABLE 13B

PCR primers for amplifying CRISPR target site, Target 1

| Gene Target | Wheat *Tsn1* |
|---|---|
| Forward Primer | 5'-TGTGCATTCTTTCCAAAAGGTCA-3' (SEQ ID NO: 33) |
| Reverse Primer | 5'-GCTCCAAAGGGCTTTAGTAGGA-3' (SEQ ID NO: 34) |

TABLE 14

Expected genotypic classes from cross: Tsn1 endonuclease target

Due to the method of wheat haploidization formed from crossing emasculated wheat spikes with maize pollen, several classes of plant outcomes are not possible. If the wheat is emasculated correctly, no self-pollinations should occur. If a mistake is made in the emasculation process and a wheat seed is allow to self-pollinate, the seed will grow more vigorously than a wheat x maize cross, and the seed can be easily screened out.

Due to the inability of wheat and maize chromosomes to pair and the inability of maize chromosomes to be inherited, classes B and C are not possible. Thus only classes D and E should be produced.

| Class | Haploid Identification Trait: embryo growth | Successful Mutation Trait: disease resistance | Phenotype indicates plant is: |
|---|---|---|---|
| A | Screened out visual as a healthy seed | na | Self-pollination |
| B | NA | na | Hybrid, not homozygous mutated |
| C | NA | na | Hybrid, is mutated |
| D | Slow growing embryo | Susceptible to SNB | Haploid, not homozygous mutated |
| E | Slow growing embryo | Resistant to SNB | Haploid, mutated |

Wheat *Tsn1* and surrounding sequence (GENBANK® accession number GU259618)

(SEQ ID NO: 35)

ATGACTACACCAATGAGTATACCGTTCGCAACTTTGGAAAAGATTACAAATG

GGTTCTCAAACGATTTAATAATTGGAAGGGGTGGGTATGGAAACGTTTACAA

GGTATGGCTTAATACTTGATATTTCCTTTTTTCAGCAAATGTTCAGGCTATAA

ACAAATAATTTAAGTGCAATAATTATGTCAAGCAGGCAGTTTACAAAGGGGA

AGTGATTGCTGTGAAGTTGCTTCATGATGATCTGGTGCAATTACTTGATGACA

GACAATTTAAAAATGAACTTTTTAACCTTTTGAGGGTTGAGCATCCGAATATT

GTTTGCTTACGTGGTTATTGTTATGAAACACGGTATAAAATTGTTAAGCACAA

TGGTGAGACAGTCTTTGGTAAACATATACACAGAGTTCTCTGCTTTGAATACT

TGGAGGGTGGAAGCCTAGACAATCATCTTCATGGTACGATGGAACTTCAAAA

TACAGTTATTTTGTTTTACGTTTAAAGGAAACTGATTTCTCATTTACATACATA

CTCTTTGTTAACTTGCGTAGCACCATCTTTGCCACCTAACTGGACCACACGTT

ACAATACCATAAAGGGGATTTGTGAAGGCTTAAATTTCCTTCACGGATGTCA

ACCACCAATTTTGCATCTTGATCTGAAGCCTGCCAATATATTAGTAGACAGTT

CCATGGTGCCTAAACTGGCGGATTTTGGATTGTCAAAGCTCTTCCATGGATCA

CATACTCATGTGACAAAACAAATCATAGGAACCCAGTAAGCGGAAGCGACC

CGTGGATTGTCTCGTTCTGAATTTTCTTTCTTTTGTGATCAAATAAATAGTATG

TACAGTTCTGTACTAACTGTGTCTTTGTATCACGCAGGAAGTACATGCCACCG

GAATTCATCAAAGATGGCAAGATCTCGGTTAAAAATGATGTCTTTAGTTTGG

GTATTGTGATCATAGAAATAATGGCAGGACCTATGGGTTATTCAGAATTTTCA

GAAATGGGCAGCGGTGCACAATTTGTGAAGGAGGTAATAAAAAAAACTCAA

GTTTGACACCCGAGTTCGTATAAATAACAAACTACCACACCAAGAATTTGAT

-continued

```
GTCTAATGTGTGAGCCATTATAATCGTTGAACTGAGTTTATGACAGGACCGGC
AGTAATAAAAAATATAGCAACACTCCCCCACACAATATATTGAGCATAGAAG
ATACAACTTATCTAGCTATAACAAAATAATAATCCAGAAAAGTAGCCATTTTT
TTTTCCGGACAGGATTGAGGTCCACCAGTCCAATAACTATGAAGCAGCTCGC
TGATAGAAAATTCCAAGGTACAATTATTTTTGTAAGTTTCTCCTTATCACGTG
TGAAACACCAATGTAATAAAGCTGATAAACCAAACGTACCCACTATGAGAAC
TGCATACACTGAGACTCGAAGAAAAGAACAAATGCATATCTAGAACCTTGCT
CCATGGGATATCTAGAACCTTGCTCCATGGGATCTAGCACCATCTCCATTTTG
GAGCAAGCACGAGGTGCGTATCGTAATCTTTTTCTGCTAGATGCAGACTTAG
ACACCCAGTATTCTCTAGGTAAATTATTTATCTGGAAAGTCGTAGGTAACACT
TGTGAACAAGGATATAGCGTACATATATATGGGAGCATTTGTGTTATGTGAC
ACTTTTGACTTAATTGCAAATATTATGTTATGTGAAGACTCAAGAGTGTTTTT
GAACAAGTATCGTACATATTGTACCGAAAAAGGCTTTCGCCCCGCTTTATATT
ATAAAGCACATGCCCAAGCCAACAAACCACACAGGTTCACAAACACACGCA
GACCCACACACACCAAGTTCACACACAGACAAGATCCACAAGGGTTAATGCT
GAGGGCACAGCTTAACAAGCCCTAGAACAAAAAGGAAAGACACCATCTAGT
CGGGCTCCGGGGGGGGGGGGGGGGCGGCGGAAGTGGAGGCGCCAGG
CGGAAGGCGAGCGATCGAAGGTCGGCGAGGAGGGTGTTGATGATGTCCCGA
TCCTGAGGGCGGCTAAGCGGCCGCCAAAGCTGCAAGTACCCACACATTTTAA
AAATGGCGTCAGTAGCGCGTCGTAGAGGGACTTTTTGGATGACAAGCTTATT
GCGGACGGTCCACAGCGTCCAGCCGAGAACCCCAACGCATAACCAACGGAT
ATGTCGGTGGCGTGGGGGGGAGGCGTGGATTTCCGCGAGGAGGTCGGGGA
AGTTGGAGTTGCACCACTATCCGCCAACCGTCTCACGGAAACTGGACCAAAG
AAACTGGCCGCAGGGCACGTGAAGAAGATGTGGTTAGCATCCTCCGCAGTGC
CGCACAAGGGGCAAAGCCCATCCCCGGGTCCGTTGCGCTTGAGGACTTCGAC
ACCGGAGGGGAGGCGGCCACGAATCCACTGCCAAAGGAAGATCCTAATCTTC
AGAGGTAAGCGAATGTCCCAGATCAGAGCAAAGGGCTCGGGCGCGGGCGAA
GGCGCAATAGCCGCGTACATGACCTAGTAGAGAAACGACCGGAGGACTCTA
GGCGCCACGAGATGGCGTCCGGGCGTCGGTGACGCTCATCGGAAGAAGGG
CGATGTCCTGGAGGAGGGAATCCCAGGCGGCCACTTCGGGGGGACCGAAAG
GACGACGAAACGCGAGGCGCCCTAAGTCAATAAGGGCCGTCTCGACAGAGA
CCCGAGGGTCAACCGCAATGGTGAAGAGATCGGGAAAGCGGGCGGCCAGAG
GGGTGTCACCGAGCCACCGATCAAACCAGAACAGGGTCGCGGACCCAGTAC
CAATCGAAATGGACGTGCCGATACGAAGCACAGGAAGCAGCCGCACGACGG
CCTGCCAAAACTGTGATCCGCCCGAACGCTGACAGAAAGCCAGAGGCTGGCC
ACGGAGGTATTTGTTGCGGATAATGGTGAGCCACAACCCTCCGTCACCATTG
GCAATACGCCACAACCACCGGGTCAGGAGGGCGATGTTCATTCGGCGGGAG
GACAGAATCTCAAGACCCCCTGGTCTTTAGGTTTACAAATGTCCGGCCAAGT
CACCATGTGGTACTTCTGTTTGTCATCGTCGCCAGCCCAATAGAACCTGGATT
GGTACTTGGCAATTTCCGTGTGCAGCGTTTCATGGAGGCTATAAAAGCTCATG
AGGAACCAAAGGAGACTGGCGAGTGAGGAGTTGATGAGGATCACCCGCGCC
```

-continued

```
GCCTTTGATAGCCAACGCCCTTTCCAAGGTTCGACGCGGTGTTGCATACGGGT
CACCGTAGGGTGGAGGTCCGCCACGGTGAGGCGCGAGTCACTAACGGGGAT
CCCCAGGTAGGTCGTGGGGAAGGACCCTAGCCGACAGTTCAGGCGATCAGCA
ATATCCTGAGCCTCCTCCGGAGGGTATCCAAGGACCATCACCTCGCTCTTATC
AAAGTTAATCGTAAGGCCCGACATCTGCTGGAAGCACAGGAGGAGGAACTTC
AGGTTAGCAACATCCTGATTTGAACCTTCCACCATTATTATGGTGTCGTTCGC
GTATTGCAGGAGGGAGACCCCTCCCCCTCCAACTAGGTGAGGGACAATGCCG
TGGATATGGCCAGCACCCTTAGCCTTATCCAGGATGGCGGCCAGAGCATCGA
CCACCATGTTGAACAGGAACGGCGAGAATGGGTCTCCTGACAGACCCCACAG
AGGGTGGGGAAGTATGGCCCAATCTCGCCGTTAATGTTCACCGCCGTCTTTCC
ACATGAAACTGATTGCATCACGCGGGTCACCCAGCGGTCATCAAAGCCCTTA
CGCAGCAGTACTTCCCGAAGGAAGGGCCAGTGAACAGTATCATAGGCTTTAT
GGAAGTCAAGCTTCAGGAACACAGCACGAAGATGCTTCACCCGGACCTCGTG
AAGGACTTCATGGAATACCAACACGCCATCAAGAATAAACCGGCCTTGGATG
AAGGCCGATTGGTTCGGGTGAGTGATCGAATCAGCCAGCAGGGTCACCCTAT
TGGCGTACCCTTTGGCCAGGATCCGAAAAATCACGTTAATCACCGTGATGGG
GCGGAACTGGCGAATATCAGAGGCACCCGGAACCTTTGGGATGAGGGTAATG
ATCCCATAGTTGAGGCGTCCCAGGTCCATCGAACCCGAATAGAACTCCTCGA
ACAAAGCCATGACCTCCGGTTTGACCGCCTGCCAGAATGTTTTAAAGAAAGC
AACAGGCAGGCCATCCGGGCCTGGGGCCGAGGCGGGGTTCATGCCTTTAATG
GCCGCGAGCACCTCGTCCTCGGCGAAGGGAGCAACCAGGGCCGCATTGGCCT
CGCCGGGAACCAACTGCGCCCCCGTCCAAGTATCGGGGGCATCGTACATATT
GTTATATGCTCCATCTCTAATTGTATCTCTATATTTCGGTTTTGTAGGTACTTA
CCAATTGGAGTACTATCATTAAAGCTACATCAGAGTATCCAGCAGAGGAACT
ACATCAAGTGAATTTGTGCATCGACATAGCAATGCTTTGTGTGGATTCTGAAA
GAGTCAATAGACCCACCATAGCTGGTATCCTAGATGCATTGAATAGGACAAA
AACTCATATGCCCTCCTCTACGAAAAAAACTCATATTCCCTGGGGACAGGTAT
GATTTGCATACTTGCAAACAAAATGAAATCTCGAGTATATATTTGCAATCTGT
AGAAGACAGTTGCTTGGATATATGGACCACTAAGTAGTTATAGAGTTTGCAG
CTCCCCGTCTCCCACTCATTTTATTCTCAATCAAGTAGTTCTTTAATAGTCAGG
AACTTGCTTACTGCATCCTTTTGACTCCCTGCTCTATAATCCATGTAGAAGAA
CCTTCATTTTAGTTCCGGCTAATTCCAGGAATAGAAAACTAGAGAGGGCCTAT
TCGTAATCGTGCCTTCCGGAGTGACAGGCTAAGTGAAGGGCAGGGGATGCT
GCCCTCGACAACCGTGGCTGTGATTGGCACTGTCGTGCTCATACGAGGTACC
AGACGGTGTAGAAGTTAACCTAGTTGATTAATCTTAGGTGTGGTCATGCTAG
ATAGCTATATGAAAGAGCCATACATGTAGTTCAAGTAGTGCATGCAAGATTC
CAACATTCAAAATCGTGCCTTGTACTATGGAAGGGGAAAGGGAGGGGTAACA
CGTAATGAGTGCCCTATAAGCCTTACACAATAGCTTTATCAGACCACTGTGGC
GCCCTAACTGACGCCAACAGAGGTAGCTGCAATGGTTCGATGAGATAGCGGT
GAGAGAGAAGGGGCAGGGGACATTGGTGGCAGGTGTAAGGGAAAAAGGG
```

-continued

```
AGAGGAGTGAAGCCGGCTGGGTACCTTGGTGGGGGAGAGGAAAGGGTGGAG

GAAGAACAAAGAGGTGAGGCGCCTGCTAGTGATTGCACTGTAAGCCTACCGC

GCGACATTGCTCCAAAGCTACGCTCTCCCAATAAAGGAGAACTTCTAGAGAG

TTGATATGAATTAAAGAGATTACCACAGACTCACATAGTGCCTGAGGTATTA

GCCACATTTCCTTTCATGCCCTTGCCGAGGGGCTTTCCTCGGCGCCTCTCACTT

TGGGCTTTGCTTCTTCAAAGGTGGTGTTTAGGCCGCAAAGAGTACAACCAGT

GTGTTATGTGTGTGCACTTTCGGTGTGTTACAATTTGCCATTATTGCTTGATGC

TTTATTACTATTCAAAATAGTTTCTCTTTTTCCAAGTTGTCATTTTAACATAGC

ATTATAGATTTTGTCCTTCCGATTTGCATGTTTTGATCGTCTATAACTTAGTTT

ACATAATGGAAGCACATCCCAGAGAGTAAATTGATCATGAGATCTTGACCAT

GATGATTCTCCTGTTTTTTCCTTGTACTTACACATAAAAGTTGTTTCAGTTGG

AAGATGTGCCCCTGTGTTCGACAATTGGTCCCAAAAGTACGAGTAAAAGGTC

GAACCCAGTTCCCACAAAGGAAAATAAAAGGTTGAAGATGATGACAACTGA

AGTGGACAATATCGCGAACAAACACCAACAGTTTAATTGCATGCCAGGAGAT

AGCTCTAAAACTATTGTTCAGCAAGTTCCAGACAGGGAAACATCATCAGATG

TGGAACCGACATTAATCATTGGAAGGGATGAAGAAAAACATAAAATATTGTC

CATTTTATCTGAGAGCAACGCAGAAGAGATGACCATCCTTCCAATATATGGC

ATCGGAGGAATTGGCAAGACAACCTTGGCACAATTGGTGTTCAATGACATAC

AGTTCCGGGACTACTATCGGGTGTGGGTATATGTTTCTCAGAAGTTTGACTTA

AAGAAAATTGGCAACTTTATAATATCACAGTTAACAAAAGAGACCAGCGATA

TAGATGACCAGCAGACACTTCATAATCGCCTTAGACAGCTATTTGCTGGTAA

GAGTATCCTTATTGTTTTAGATGACCTGTGGGAGGAGAAACAACATGAGTTA

GAGAAATTGAAGGCTATGCTAAGGCTTGGCATAGGAAACAAGGTTGTCATAG

TAACTACACGTGATGAAGCCATTGCAAGGAAAATCAACAGGACTGTTATGCC

ATACAAGCTAGAGATTTTAACAGATGATATGTGCTGGTCTATAATAAAACAA

AAAAGTTTCTTTGAAGATCGATGTGACAAAGAACAATTGGGGCAGATCGGAA

TGGACATTGCAATCAAGTGTGGAGGTGTGGCTTTGCGGCTCAATCACTTGG

GTACATGTTGAGGGAGATGGAGTCTGACCAATGGGAGTCAGTGAGGGACAGT

TATATCTGGAATCTATCTACTATGGAAGATCCATCATTAAGAAATCATGAAGT

GCTTCTGTCCTTGCTGTTAAGCTATTCCCATATGCATGAATTCTTGCAGTTATG

CTTTTCCTATTGTGCATTCTTTCCAAAAGGTCAAAATATAGTGAAGTATGATC

TAATTCACCAGTGGATAGCTCTTGGATTCACCGGTCCATCTGGAATATTTGAT

TCTATTCAGCTCTGTGAGAAATATATTACACGGCTTTTGGGGATGTCATTCCT

TCAATATTCAAAGACACGTTCGGTGAGTTACTACATACTCTCGATGTCCCAAA

AGATAGCTATGGGTAGTTTCTTCATGTCAAAGAGTCCCCTTCCAGTACTGCTA

GGTGTCAGGTTTCTAGAAGGCCGCTAGGGCATCTTAGATAGGGTCATAGTTA

TACACTACTCATCCTCAAATGCATATGCCTGTGCAATTTTCTTTTCTAGATGAC

CTTCTCGACAAGCTCGTTGACATTTATCCTTTTTCTTTTTCTTTTCTTTCCCTTG

TTTTCAACCTTACCTTTCAAATTTCCTTTTCCAAGAATGACATTCAAGTCCATA

ACCTGATCGTGGATATGGGTCCTACTAAAGCCCTTTGGAGCTCAATATTTTTC

AACTATTTCATTAAAATGAATTCACATCTATAATCATCATTTCTTTTGTTATGT
```

```
ATGTATATAAAACAATACTAATTATTGTTGAACTAATAAACACATCGTTGATT

ACCTCTAAACAAATTTGAATGTCATTAAATTTGTCTTCATATTTTTTAGTGGG

ATAAGACCCCAATCCAACAGGCGCCCAAACAAATGGACCTATGTACTGAAAC

GTTGCTGTTGCTGGTGCATTTGTAGTGCTGGGTATTAATTTTAGCAGGTTTAA

GATGAAAACCACTGCAGATATTTATCCCAGGCATTATTTCATTTGATATAAGC

TTTGAAGTTTACAGATCCATAGTGTAATCTACTCTGGTGTAATTTAAATATAC

TGATCCGTTGCCCATTATCGAGAAAACATACAGCTACGGTTACACTCTTTTAT

AGTGATACAAAAGTATTTCTGTTGATAAAATATACTACTATAAAACAAAATA

AATTCAATATTCTAACAACATTACGTGGTTTTGCTGCAGAGTGATGAACGGCA

GGACAAAGATGTTAAAATGTTTGTAATGCATGACCTAGTGCACGATCTTGCA

AGAGCAATATTGGCTGATAAAGTTAATAAAGAGGGTGATGCTGTGGGAAGCA

GTTGTCACTATGCATTGCTCACAGATTGTAGCAAGCCATTGCAGTTGTCTGTT

AGTTCAACTGAATATAGCCGGTTCAATTTTTTCTTAGCCTGTTTAAAAAGAA

GAGTTCACATGAAAATATAAAGGCGTTACGTTTTCTGAACTGTGGCAAAGTA

CTACTTCGCGGTGATGCATTTTCACCTGCCAAGTTCCTCCTTGTCTTAGATCTA

AGTGAATGCTTTATTCAGAAGCTCTCACTTGATTCGATTGGACAACTGAGGCA

CTTGAGATATCTTTGTGCTCCACGGGTCAACGATTACACGATTCCCAACTGTA

TCACCAAGCTCTCAGAATTAACTTACCTCAACCTTAGAGGCTCTTGTCGTATC

TCAGCATTGCCAGAGTCAATTGGCGATATGAAAAGTCTGATGCATCTTGATTT

ATCAGGCTGCTGTGACATAATTGAACTCCCAGTATCATTTGCGAAGCTGAAA

CAGTTGGTGCATCTAGATTTATCACACTGTCACGTGTCTGTATCAGAAGATTT

TGGTGGCTTTACCAAACTTCAATATTTGAATTTATCAGTTTTGTTTAGTTCTTC

CAAGGGGCATAGGAGAGGACTGCTAGAGGTCATTGGCAATTTAAAGAAACTC

AGGTATCTAAATCTATCTCGGTGCATGGAGGACATAGCCACATCAGAAAACC

AAATTGGCAGTTTGCTTGACTCTATCAGTACCCTTTCCAACCTTGAGCATCTG

GACTTGTCTGAGAATAAACAGCTTTCCAGTATACCAGAAAGTATGGGCAACC

TCAGGAAGCTTCATACATTGGACCTCTTAGGCTGCTATCAACTAGAGAAGCTT

CCTGATAGTATGATTAATATGGTTAGCCTGAAGGTTCTAAATGTGGGTAATTT

GGTTACACTGGATGAATCTGTGCTCTCTTTGTTAAATATTGCCTCCTTGCCAC

ACTTTGTGGTGCATGCTTCAAGTGGTAAATGTAGCAGCAATATCACCCGTCTT

CAGGCTACAAATCCTGATAGACTGATTATAGATAGACTTGAAAATGTCAAAT

CTGCAGAAGAGGCACATAACATAAAACTGATAGAGAAACAGAAAATTGAAA

CCCTACAATTTGAATGGACTGTGGCTGCTAGGAGGTTTGTGGATGACAAAGA

GGTGTTGGAAAAACTAGTGCCGCCAAGCAGTGTCGACAGTTTGTGTATAATT

GGTTATAGAAGTGTCAGCATTCCTGATTGGCTTCTGGGTATTAGTCAGTATCT

CCCTAATCTTGCGATTATAAGTCTGGTTAATTTTTCTAAGTGCAAGAACCTAC

CACCACTCGGTCAACTACCAAACTTACAATGGCTGACTCTCAGCAGTATGGA

TGGTTTGGAGGAGTGGAACACGACATATACTACTGGAGAGCAAGGTAGAAA

CGAACTCTTGTTCCCTAAGCTTGAGAGATTAAACATACATGACTGTGCCAAGT

TGAGGATAGAACCATGTCTGCCTAGAGCTTTGTATTTGCGCATACGAGATAGT
```

```
                         -continued
AATAATGTGCTATCCTCACTCAATACAAGAGAGCAAGCTGAGAGCACGCTGC

CCTCGGACATAGCACATTGTGATAATATGATATCAGCATGCGGAAAGAGTTC

GTCATACAGCGGTGCTTCCTCTTCTTCTCCAATAACTGATCTGTTTGTAGAGG

AAAGCAAACTACCCTTGCATCAGTGGAGGTTGCTTCACCAACTCCCCGCGCT

CCGTGGTTTACGGATCAAACATTGCAGTGATCTGACCACCTCACTTGCTGTTA

TCCAAAAACTCTCCTCCCTCCAAAATTTGAGCCTGGAGCTCAACGACCATGA

ACTGCCGAGTTGGTTGATTCAGCTGACAGATCTACAGGAATTAAAGCTTATG

CATTGCAATAGCATTACATCACTACCACAGTGGTTTGGAGAACTTGCATCTCT

CAAGAGAATTGAGATCAAGTACTGCAAGGGGATCAGCTCTTTGCCGGAGAGC

ATACAACAACTGACTAAGCTTGAATTTCTAAGCATTCATGGCTGTCCTGTATT

AGAGGAGTGGTGTGAATCAGAGGAGAACAAGATGAAGCTCACTCACATCAA

AGTTGAGGTATGTGCGTGCAAGTTATCTGTTGTATTGCTTTTATTCTCGTGCTG

GTAGTGACTTAATACTCTTTTCTTAAATGGCAAGTATACACATGCCATGAGTA

TCTTTACATAATCATGGTAAGTGTTGAATTAGGTGTATGTATTTTGTCTATTAG

ATGCTTCATGTGTCTAGATTACTTGACAAAAATATGTGACGACTGCATTAATA

ATTCGCCTAAGAAGAAAAGCATTCCAGTTGTGATTGTGCTATATCATGCACCT

ATACATGCATTGTTCTGATTATATATCCCGTTTGCATTGTTCAGATCGCTGGA

CGGGATTCGGTAGGCTTTGAGGATTCGAAGGTTCAGATTGTCAAACCAATGC

CAGCACAAATGGTTCGCCAATCAGCATTTGCTACTACAGAACGAAGATAG
```

Example 4—HILAGE: Oat

Haploid inducer methods: Oat (*Avena sativa*) HILAGE-based methods are conducted with standard oat in vivo haploid induction using a cross with a maize pollen to pollinate an emasculated oat spike, embryo rescue in tissue culture, and subsequent chromosome doubling techniques such as those known in the art (see, e.g., Rines, "Oat haploids from wide hybridization," in *Double Haploid Production in Crop Plants: A Manual*, Maluszynski, Kasha, Forster and Szarejko (Eds.), pp. 155-159, Kluwer Academic Publishers, Dordrecht, Netherlands, 2003). Briefly, the in vivo technique of oat haploid induction first requires that an emasculated oat panicle be pollinated with maize pollen and treated with 2,4-D and 50 mg/L gibberellic acid (GA3) two days after pollination. Fourteen days after pollination, the developing oat embryos are removed from the spike and transferred to tissue culture. The developing embryo is grown in tissue culture into a plantlet following methods described by Rines (supra). The plantlet is then chromosome doubled and transplanted to the soil to produce doubled haploid seed.

Endonuclease transgene and transgenic construct: Oat HILAGE-based methods add the targeted mutagenesis component to the in vivo haploid induction system and thus require an endonuclease. In oat HILAGE, one or more of the maize chromosome(s) carry an endonuclease transgene capable of causing targeted double strand breaks in the wheat genome. Useful endonucleases include, for example, meganucleases, ZFNs, TALE nucleases, and CRISPR/Cas-based endonuclease systems. The endonuclease is designed to target AsFAD2a and AsFAD2b, but an endonuclease could be designed to target nearly any sequence. The endonuclease(s) are constructed using methods such as, without limitation, those described by Sander et al. (supra), Cermak et al. (supra), and Liang et al. (supra). The promoter used to drive expression of the endonuclease is endogenous or exogenous. High expression of the endonuclease is essential to increase the chance that a targeted mutation is successful before the removal of the maize chromosomes carrying the endonuclease transgene. Suitable promoters are expressed during early embryo development, and can be endogenous or exogenous. Examples are provided in TABLE 8.

The endonuclease construct also may include a selectable marker, such as a gene that confers herbicide resistance, to assist in recovery of the transgene during whole plant transformation and subsequent backcrossing. When included, the herbicide resistance selectable marker is driven by a promoter with strong expression in maize and/or oat.

In another embodiment, the transgenic construct containing the endonuclease or a second construct combined into the same maize line contains one or more copies of a sequence of DNA with homology to the DNA at and flanking the target site. This sequence of DNA may contain nucleotide changes such as one or more base pair substitutions, deletions, and/or additions. Alternatively, this sequence may contain a gene, a promoter, a regulatory sequence and or a transgene.

Testing the endonuclease in transgenic oat: While HILAGE-based methods do not use a transgenic oat line to generate the final product of doubled haploid oat with targeted mutations, it may be beneficial, though not necessary, to test the efficacy of the targeted endonuclease construct in a transgenic oat line. Oat transformation could be conducted following techniques such as, but not limited to, those described by Zhang et al. (*J. Plant Physiol.* 148(6): 667-671, 1996; and *Plant Cell Reports*, 18(12):959-966, 1999). Transgenic oat with putative mutations can be checked for targeted mutations using methods similar to those described for *Arabidopsis*. Endonucleases demonstrating efficacy for causing double stranded breaks are utilized for oat HILAGE-based methods.

Generating a maize line for oat HILAGE: A major difference between oat HILAGE-based methods and normal doubled haploid creation in oat is that a transgenic maize line is being used for haploid induction instead of a conventional maize line. As such, a maize line is being transformed with the endonuclease construct. The endonuclease transgene could be added to the haploid inducer using several methods such as, but not limited to: Agrobacteria methods (Gasparis et al., *Plant Cell Reports* 27(11):1721-1729, 2008) or by particle bombardment (Somers et al., *Nature Biotechnol* 10(12):1589-1594, 1992). Since the line used for maize transformation likely is not a prolific haploid inducer, it may be beneficial, though not necessary, to backcross the endonuclease transgene(s) into a genetic background shown to be effective and highly efficient at oat haploid induction. The backcross introgression of the endonuclease transgene into a more suitable maize line could be conducted with the assistance of molecular markers to select for the presence of the transgene, as well as to select for the genetic background of the recurrent parent (the suitable maize line) and against the donor parent line (the originally transformed maize line).

Depending on the promoter chosen to drive the endonuclease, the endonuclease will likely show different expression in the maize line than in the progeny of the maize-oat cross. If the gene is expected to express in maize, it may be beneficial to assess RNA and protein expression of the endonuclease to confirm that the endonuclease is functional.

Genotyping of mutated oat plants: The plantlets are genotyped before or after transplanting to soil to identify (1) if the desired targeted mutation(s) occurred, (2) if the oat plant no longer contains maize chromosomes (a necessary test in oat), and (3) if the transgene(s) are no longer present. The third test is not necessary if the maize chromosomes are removed, but it is still probably a good standard operating procedure to ensure removal of the transgene as there is significant current market place resistance to transgenic oat). Additionally, potentially different tillers may need to be genotyped as the plant could be chimeric for one or more targeted mutations and or for the presence of maize chromosomes. Checking for mutation(s) at the target site(s) can be conducted as previously described for *Arabidopsis*. The presence of maize chromosomes, is assessed by one or more of several methods. For example, primers can be designed to amplify specific sequences on each of the 10 maize chromosomes in the maize line used for haploid induction, and these primers can be used to determine if the maize chromosomes are still present. Alternatively, a custom SNP chip can be designed that can be used to genotyped the oat line and also maize DNA. In oat plants that have lost the maize chromosomes, the oat SNPs are able to be genotyped, but the maize SNPs are not able to be genotyped. Alternatively or additionally, a low coverage whole genome sequencing method or RNA sequencing method could be utilized to determine if the maize chromosomes are present and/or maize genes are being expressed. If the maize chromosomes have been removed from the oat plant, it is likely that the transgene had also been removed. However, to increase industry and consumer acceptance of HILAGE-based methods, it may be beneficial to test for the absence of the transgene(s) in the oat line. In one method, primers that amplify portions or all of the transgenic construct can be designed and used to test if any portion of the construct is in the produced oat line. Alternatively, the sequences of the transgene can be search for in whole genome sequence or RNA sequence data, if said data are available.

Utilization of oat HILAGE: The maize line containing one or more endonuclease and or CRISPR guide RNAs is being crossed (as the pollen donor) to an oat line to generate haploid progeny. Before the maize chromosomes are eliminated, the targeted endonuclease induces targeted DNA double strand breaks in the DNA from the oat line. Some of these double stranded breaks will be incorrectly repaired and a mutation will result. The haploid progeny genomes can be doubled before or after the progeny are screened for the mutation(s). Once the genomes of these haploid individuals are doubled the individuals can be grown out and self-pollinated to produce doubled haploid seed. Different mutations may be produced, and each mutation event is evaluated to determine if it has the desired result. Only lines with EM are advanced.

In some cases, HILAGE-based methods are conducted on all (or many) of the oat lines that may be used as parents for breeding. If populations using lines that have an EM at all targeted loci are developed, the populations will not segregate for the EM. Thus the breeding efforts are simplified by not having to conduct selections for the presence of the EM.

Advantages of HILAGE-based methods in oat: The use of HILAGE could play a pivotal role in generating targeted mutations in oat. Globally, there is still resistance to utilizing transgenes in oat. HILAGE-based methods may induce targeted mutations in oat without the released oat line ever technically coming in contact with a transgene placed into an oat chromosome. In addition, HILAGE-based methods may be more effect in oat than in maize since it is likely that the maize chromosomes persist longer in the maize-oat embryo than the haploid inducer maize chromosomes persist in the maize haploid inducer-regular maize line embryo. The additional time that the maize chromosomes are residing in the oat embryo, the more opportunity for targeted mutations to occur.

Exemplary target sites and methods for genotypic screening in oat are provided in TABLE 15A, while exemplary primers for amplifying the target site are provided in TABLE 15B. Expected genotypic classes from the cross are shown in TABLE 16.

Oat genes to target—AsFAD2: Sequences of the target oligonucleotides were as follows (with f1/r1 for target 1 and f2/r2 for target 2).

```
AsFAD2
                                          (SEQ ID NO: 36)
  f1 5' GATTGGGTGCCGGTGGCAGGATGA 3'

(SEQ ID NO: 37)
  r1 5' AAACTCATCCTGCCACCGGCACCC 3'
```

Underlining indicates the 20 bp target sequences.

TABLE 15A

Target Site and Methods for Genotypic Screening, Target 1

| | |
|---|---|
| Endonuclease | CRISPR |
| Gene Target | AsFAD2 |
| Gene Target | AsFAD2 |
| Target sequence | GGGTGCCGGTGGCAGGATGACGG (SEQ ID NO: 38) |

TABLE 15A-continued

Target Site and Methods for Genotypic Screening, Target 1

| | |
|---|---|
| Mutant Phenotype | Increased oleic acid levels |
| Genotypic Screen | CAPS assay; enzymes BtsCI, BsrFI, BanI, and NlaIV |

TABLE 15B

PCR primers for amplifying CRISPR target site, Target 1 & 2: AsFAD2a and AsFAD2b

| | |
|---|---|
| Gene Target | AsFAD2 |
| Forward Primer | 5'-TTCGTCCCGTCAACAAGAGG-3' (SEQ ID NO: 39) |
| Reverse Primer | 5'-GTCCGTCGGCGAGCGCTGG-3' (SEQ ID NO: 40) |

TABLE 16

Expected genotypic classes from cross
Due to the method of oat haploidization formed from crossing emasculated oat panicles with maize pollen, the self-pollination outcome class is not very likely to occur. If the oat is emasculated correctly, no self-pollination should occur. If a mistake is made in the emasculation process and an oat seed is allow to self-pollinate, the seed will grow more vigorously than an oat x maize cross, and the seed can be easily screened out. Due to the ability of oat and maize chromosomes to pair and the inability of maize chromosomes to be inherited, classes B and C are possible, and phenotyping and genotyping need to be done to remove these classes.

| Class | Haploid Identification Trait: (mixed options) | Successful Mutation Trait: | Phenotype indicates plant is: |
|---|---|---|---|
| A | Screened out visual as a healthy seed | Na | Self-pollination |
| B | Visual phenotypic assessment and genotypic evaluation with molecular markers | NA | Hybrid, not homozygous mutated |
| C | Visual phenotypic assessment and genotypic evaluation with molecular markers | NA | Hybrid, is mutated |
| D | Slow growing embryo, tests negative for maize DNA | Wild-type levels of seed oleic acid | Haploid, not homozygous mutated |
| E | Slow growing embryo, tests negative for maize DNA | Higher levels of seed oleic acid | Haploid, mutated |

Putative Consensus Sequence for AsFAD2 (and Surrounding Sequence)

(This sequence was identified by aligning oat contigs that putatively code for FAD2. Oat contigs found by searching for alignments in Oat CORE database that have high sequence similarity to barley, rice, and maize FAD2's (5'UTR+coding). ATG start is bolded and underlined. Putative FAD2 gene is underlined.

(SEQ ID NO: 41)

CATAAACCACTCGTTCGTCCCGTCAACAAGAGGAGCAGAGGCGAGGGACTCG

CGCTCGCGTGTGTGGTGTCCTTCCCTCGATCTGCCCCTCTCCGGCCAGTTCTAT

CACCTCCTATCAGCAACATGGGTGCCGGTGGCAGGATGACGGAGAAGGAGA

GGGAGAAGCAGGAGCAGCTCGGCCGCGCCGACGTCGGTGCGACCCTCCAGC

GCTCGCCGACGGACAAGCCGCCGTTCACACTGGGGCAGATCAAGAAGGCGA

TCCCACCCCACTGCTTCCAGCGCTCGGTGATCAAGTCATTCTCCTACGTGGTC

CATGACCTCGTCATCGTGGCTGCTCTCCTGTACGCCGCGCTGGTCTGGATCCC

CACCCTCCCGAGCGTGCTGCAGCTGGGCGCCTGGCCGCTCTACTGGATCGTG

CAGGGCTGCGTCATGACCGGCGTCTGGGTCATCGCGCACGAGTGCGGCCACC

ACGCCTTCTCCGACTACTCGCTCCTCGACGACATCGTCGGCCTGGTGCTCCAC

TCGTGGCTGCTGGTCCCGTACTTCTCGTGGAAGTACAGCCACCGTCGCCACCA

CTCCAACACCGGCTCCATGGAGCGTGACGAGGTGTTCGTCCCCAAGCAGAAG

GACGCGCTGGCCTGGTACACCCCATACATCTACAACAACCCCATCGGCCGTC

TGGTGCACATCGTGGTGCAGCTCACCCTCGGGTGGCCGCTGTACCTGTCGATG

```
-continued
AACGCCTCGGGCCGCCCGTACGCGCGCTTCGCCTGCCACTTCGACCCCTACG

GCCCCATCTACAACGACCGGGAGCGCGTCCAGATCTTCATTTCGGACGTCGG

TGTGGTGGCCACGGCGTTCACCCTCTTCAAGCTTGCTTCGGCGTTCGGGTTCT

GGTGGGTGGTGCGCATCTACGGTGTGCCGCTGCTGATCGTGAACGCGTGGCT

GGTCCTGATCACCTACCTGCAGCACACCCACCCGGCGCTGCCGCACTACGAC

TCCACCGAGTGGGACTGGCTGCGGGGGGCGCTGGCCACCATGGACCGGGACT

ACGGCATCCTCAACCGCGTGTTCCACAACATCACGGACACGCACGTGGCGCA

CCACCTCTTCTCCACCATGCCGCACTACCATGCCATGGAGGCCACCAAGGCG

ATCAAGCCAATCCTGGGCGAGTACTACCAGTTCGACCCCACCCCCGTGGCCA

AGGCAACATGGCGCGAGGCCAAGGAGTGCATCTACGTCGCGCCCACCGAGG

ACCGCAAGGGCGTCTTCTGGTACAGCAACAAGTTCTAGATTCGTCATGGGGA

CCTGCTGTGCTGCTGGAATGTGAGGAGGAAGAAGTCAGTAATACACCAAGTA

TCCATCCATCTACCTACATATGGTTGGGGGTTAGTAGTCTTTAGATAGAAGAG

AGCGTTGTTTGGGCACAAGGAAAAGACTATGACCACCGTGCCAATGCTAGAA

GAGTCGAAGCAGGTGCAACGAGGAGTAGCGTGTCGGGTGTCCGTGGCTTTGG

TCAGTTCCGTCCTGTGTCTTTACTTCCTAGTCGCCGGTTT
```

Example 5—HILAGE: Barley, Using Crosses to *Hordeum bulbosum* or Maize (*Zea maize*)

Haploid inducer methods: Barley (*Hordeum vulgare*) HILAGE-based methods are conducted using the standard barley in vivo haploid induction using a cross with a *Hordeum bulbosum* or maize line, embryo rescue techniques, and subsequent chromosome doubling techniques such as, without limitation, those described by Kasha and Kao (Nature 225:874-876, 1970), Chen and Hayes (*Theor. Appl. Genet.* 77:701-704, 1989), Chen et al. (*Genome* 34:603-605, 1991), Laurie and Bennett ("Chromosome behavior in wheat x maize, wheat x sorghum and barley x maize crosses," In *Kew Chromosome Conference Proceedings III*, Brandham (Ed.), Norwich, UK: The Stationery Office Books, pp. 167-177, 1988), and others. Briefly, the in vivo technique of barley haploid induction first requires that a cross be made between *Hordeum vulgare* and *Hordeum bulbosum* or maize, the haploid inducer line. In HILAGE-based methods, the haploid inducer stock line is likely used as the male, since for the barley haploid induction method, the *Hordeum bulbosum* or maize is used as the pollen donor and the female is the *Hordeum vulgare*. The in vivo technique for barley haploid induction first requires that a *Hordeum vulgare* plant be emasculated and then pollinated by *Hordeum bulbosum* or maize, the haploid inducer line. The developing barley embryos are removed from the spike and transferred to tissue culture. The developing embryo is grown in tissue culture into a plantlet, chromosome doubled, and grown to maturity to produce doubled haploid seed following methods described by, for example, Kasha and Kao (supra).

Endonuclease transgene and transgenic construct: Barley HILAGE-based methods add the targeted mutagenesis component to the in vivo haploid induction system, and thus require an endonuclease. Endonuclease are constructed using methods such as those described by Sander et al. (supra), Cermak et al. (supra), and Liang et al. (supra). Examples of suitable endonucleases include, without limitation, meganucleases, ZFNs, TALE nucleases, and CRISPR/Cas-based nucleases. The endonuclease is designed to target Vrs1, but an endonuclease can be designed to target nearly any sequence. The promoter used to drive expression of the endonuclease is endogenous or exogenous. High expression of the endonuclease is essential during the first couple stages of mitosis in the developing embryo. Suitable promoters are expressed during early embryo development, and can be endogenous or exogenous. Examples are provided in TABLE 8.

The endonuclease construct may also include a selectable marker, such as herbicide resistance to assist in recovery of the transgene during whole plant transformation and subsequent backcrossing. The selectable marker is not required for HILAGE-based methods and thus, in another embodiment, the endonuclease construct does not have a selectable marker for recovery during transformation.

In another embodiment the transgenic construct containing the endonuclease or a second construct combined into the same barley line contains one or more copies of a sequence of DNA with homology to the DNA at and flanking the target site. This sequence of DNA may contain nucleotide changes such as one or more base pair substitutions, deletions, and/or additions. Alternatively, this sequence may contain a gene, a promoter, a regulatory sequence and or a transgene.

Testing the endonuclease in transgenic barley: It may be beneficial, though not necessary, to test the efficacy of the targeted endonuclease construct in a transgenic barley line. Barley transformation is conducted according to techniques such as those described by, without limitation, Tingay et al. (*Plant J.*, 11(6):1369-1376, 1997) and Travella et al. (*Plant Cell Reports*, 23(12):780-789, 2005). Transgenic barley with putative mutations also may be checked for targeted mutations using methods similar to those described for *Arabidopsis* herein. Endonuclease(s) showing efficacy at causing double stranded breaks are utilized for barley HILAGE-based methods.

Introgression of the endonuclease transgene into the haploid inducer: The next step in barley HILAGE-based methods is the addition of a transgenic endonuclease gene to the *Hordeum bulbosum* or maize haploid inducer line. The endonuclease transgene could be added to the haploid inducer using several methods. One method involves the direct transformation of the haploid inducer to add the transgene, using, for example, Agrobacteria methods as described by Tingay et al. (supra), Travella et al. (supra), and Ishida et al. (supra), or particle bombardment as described by Travella et al. (supra) and Gordon-Kamm et al. (supra). Alternatively, a line amenable to transformation can first be transformed with the endonuclease transgene, and then this line with the endonuclease transgene can be crossed to a haploid inducer line. $F_1$ diploid progeny from the cross can be screened, and can be backcrossed to the haploid inducer line. This backcrossing process can be repeated several times to recover the majority of the haploid inducer's genetics with the addition of the endonuclease transgene. After a sufficient number of backcrosses (e.g., two, three, or four backcrosses), the resulting backcross plant ($BC_3F_1$ following three backcrosses) can be self-pollinated to produce $BC_3F_2$ individuals. The $BC_3F_2$ individuals can be screened to find individuals that are genetically very similar to the haploid inducer line and are homozygous for the endonuclease transgene. In the second method, molecular markers could be used to select backcross individuals that contain the transgene and contain high percentages of the haploid inducer genome. These selected individuals can be used for the next round of backcrossing to more quickly recover the genome of the haploid inducer with the addition of the endonuclease transgene. The resulting line that functions as a haploid inducer line and contains the endonuclease transgene is designated as the haploid inducer stock line.

Testing expression of the endonuclease transgene: Following either direct transformation or transformation of another line followed by backcrossing, several tests are run to evaluate expression of the endonuclease in the haploid inducer stock line. Alternatively, expression tests are conducted before or concurrently with the backcrossing to select transgenic events with high expression. Specifically, expression assays for RNA and for protein of the endonuclease transgene can be conducted to insure that the transgene is correctly being expressed. Transformation events with higher expression are desired for HILAGE-based methods. Efficacy of the transgene and transformation event can additionally be assessed by determining if mutations are detected in the target site(s) of the line. The presence of mutations can be evaluated as described herein for *Arabidopsis*. Events with high gene expression and the presence of mutations in the target site(s) can be outcrossed to targeted lines to identify if haploid progeny with mutations are generated. Desirable haploid inducer-transgenic event combinations produce a high frequency and number of haploid progeny with targeted mutations.

Utilization of Barley HILAGE: The *Hordeum bulbosum* or maize haploid inducer is crossed as the male to the *Hordeum vulgare* to generate haploid progeny. The haploid progeny genomes can be doubled before or after the progeny are screened for the mutation(s). Once the genomes of these haploid individuals are doubled the individuals can be grown out and self-pollinated to produce doubled haploid seed. It may be necessary to genotype multiple tillers per plant as the plant could be chimeric for one or more targeted mutations. Different mutations may be produced, and evaluation of each mutation event is necessary to determine if the mutation(s) obtained have the desired result. EM that produce the desired phenotype (e.g., a mutation that causes a frame shift and eliminates proper gene function) are advanced.

In some embodiments, HILAGE-based methods are conducted on all (or many) of the barley lines intended for use as parents for breeding. If populations are developed using lines that have an EM at all targeted loci, the populations will not segregate for the EM. Thus the breeding efforts are simplified by not having to conduct selections for the presence of the EM.

Exemplary target sites and methods for genotypic screening in oat are provided in TABLE 17A, while exemplary primers for amplifying the target site are provided in TABLE 17B. Expected genotypic classes from a cross with *Hordeum bulbosum* are shown in TABLE 18A, and expected genotypic classes from a cross with maize are shown in TABLE 18B.

Barley gene to target—Vrs1 (BAF43315.1): Sequences of the target oligonucleotides were as follows (with f1/r1 for target 1 and f2/r2 for target 2).

```
Barley Vsr1 gene
                              (SEQ ID NO: 42)
f1 5' GATTGGCGGAGGGGATGGTGACGG 3'

(SEQ ID NO: 43)
r1 5' AAACCCGTCACCATCCCCTCCGCC 3'
```

Underlining indicates the 20 bp target sequences.

TABLE 17A

Target Site and Methods for Genotypic Screening, Target 1

| | |
|---|---|
| Endonuclease | CRISPR |
| Gene Target | Vrs1 |
| Gene Target | Protein ID BAF43315.1 |
| Target sequence | GGCGGAGGGGATGGTGACGGTGG (SEQ ID NO: 44) |
| Mutant Phenotype | Change from 2 row to 6 row spikes |
| Genotypic Screen | CAPS assay; enzyme HpyCH4III and Tsp45I |

TABLE 17B

PCR primers for amplifying CRISPR target site, Target 1

| | |
|---|---|
| | Gene Target: Barley Vrs1 |
| Forward Primer | 5'-TCCAACGTGGACACGACTTT-3' (SEQ ID NO: 45) |

TABLE 17B -continued

PCR primers for amplifying CRISPR target site, Target 1

Gene Target: Barley Vrs1

| | |
|---|---|
| Reverse Primer | 5'-GAGGTGGCATTTGTGGAGGA-3'<br>(SEQ ID NO: 46) |

TABLE 18A

Expected genotypic classes from cross: Vrs1 endonuclease target (*Hordeum bulbosum* haploid inducer)
Haploid inducer stock line is the male. Most regenerated plants from tissue culture are haploid (>95%) Interspecific hybrids (diploid plants from the cross between *Hordeum vulgare* and *Hordeum bulbosum*) can be recognized by their abnormal growth habit and presence of pubescence on leaf sheaths (trait from *Hordeum bulbosum* parent) (Devaux, "The *Hordeum bulbosum* (L.) method," in Double Haploid Production in Crop Plants: A Manual, Maluszynski, Kasha, Forster, and Szarejko (Eds.), pp. 15-19, Dordrecht, Netherlands: Kluwer Academic Publishers.).

| Class | Haploid Identification Trait: various | Successful Mutation Trait: | Phenotype indicates plant is: |
|---|---|---|---|
| A | Developing seed will be larger for self-pollinations | na | Self-pollination |
| B | Interspecific hybrids recognized by abnormal growth habit and presence of pubescence on leaf sheaths (trait from *Hordeum bulbosum* parent) | na | Hybrid, not homozygous mutated |
| C | Interspecific hybrids recognized by abnormal growth habit and presence of pubescence on leaf sheaths (trait from *Hordeum bulbosum* parent) | na | Hybrid, is mutated |
| D | Weak plant | Spike is still 2 row | Haploid, not homozygous mutated |
| E | Weak plant | Spike change to 6 row | Haploid, mutated |

TABLE 18B

Expected genotypic classes from cross: Vrs1 endonuclease target (maize haploid inducer)
Haploid inducer stock line is the male. Most regenerated plants from tissue culture are haploid (>90%) (Chen et al., supra)

| Class | Haploid Identification Trait: various | Successful Mutation Trait: | Phenotype indicates plant is: |
|---|---|---|---|
| A | Developing seed will be larger for self-pollinations | na | Self-pollination |
| B | na | na | Hybrid, not homozygous mutated |
| C | na | na | Hybrid, is mutated |
| D | Weak plant | Spike is still 2 row | Haploid, not homozygous mutated |
| E | Weak plant | Spike change to 6 row | Haploid, mutated |

*Hordeum vulgare* subsp. *vulgare* Vrs1 gene for homeodomain leucine zipper protein Vrs1, complete cds, allele: Vrs1.b. GenBank: AB259782.1. The translation start site is underlined, and exon sequences are bolded.

(SEQ ID NO: 47)

```
GTCATAACTCGGCAAACATAGATTAGACAGAATTTTCTGAGTTCTTATCTAGA

GGAACTCGATGAACTTGAGGCATTGTCGAGGTTCTTCCTTTCACCGAGTACTT

TTTTGCGTGTACTAGGCAAATATATGAAGTTTGTGAGTTTCGGATCACCACCG

AGTGCAAGTTTGGACCAAACTTGACAAATACATAAGTTTGGCGAGCTCCGAA

TGAAATGAACTCTGCAAAAGAATAGAACTCGGCGCAAAACCAGATTCTAATA

GTGTGTGAATTTTTGGGCTGTTTTGTATAAATATGATGAAACTTAGTAAAATT

TCACTCAGGTCAATGCTAATGTGGAGAGTAAATAAAAAATGAAGGGAGTACT

TGGCTGCATCATATGTTTGCCCCCGATCACCTTCACATCTCCCCGTCCGGACG

GCCTGGATCGGAAAGCACTCAGCCGGAGCCCCGCCGGCGCTTGCCGTTGGGT

ACCTCTGCCACCTATTTATATTACCCCTAGGTCTCTCCCTGGAGACACGCACT

CCCCTCCTTCAACTAGTGCTTTGCGGCCCGTGGTCCTCCTCTCGATCCAGTTCC

TGAGCACACCAACAGGCAACAGAACAACCTACCGTGTCTCCCCTCCAATCTC
```

-continued

```
CTCACGATCCCTTCTTTCCCTCAGATCCGAACCGAAAGCATGGACAAGCATC
AGCTCTTTGATTCATCCAACGTGGACACGACTTTCTTCGCGGCCAATGGT
ACACACGACGCCGCGCGCGCCCGGTCTTTGCGCATGCGATGATGCAGCTGCA
GTAGCTTCAGTTTCACCGGCCAGGACACGCATGTGATGACGTTTTTTCCATTC
TGTGTTTGTATGTGCAGGCACGGCGCAGGGGATACCAGCAAGCAGAGGG
CGCGGCGCAGGCGGCGGAGGTCGGCGAGGTGCGGCGGAGGGGATGGT
GACGGTGGGGAGATGGACGGAGGAGGGGACCCCAAGAAGCGGCGGCTC
ACCGACGAGCAGGCCGAGATTCTGGAGCTGAGCTTCCGGGAGGACCGC
AAGCTGGAGACAGCCCGCAAGGTGTATCTGGCCGCCGAGCTCGGGCTG
GACCCCAAGCAGGTCGCCGTGTGGTTCCAGAACCGCCGCGCGCGCCACA
AGAACAAGACGCTCGAGGAGGAGTTCGCGAGGCTCAAGCACGCCCACG
ACGCCGCCATCCTCCACAAATGCCACCTCGAGAACGAGGTATGCTTGCTC
GCATACACTCACACTGGCTTACATATGGCGCTGCACATCTGCAGTTCCTCTCC
GTTCTTGAACATGCTTACTGACAAACATATGGCCAGCTGCTGAGGCTGAAG
GAGAGACTGGGAGCGACTGAGCAGGAGGTGCGGCGCCTCAGGTCGGCA
GCTGGGAGCCACGGGGCATCTGTGGATGGCGGACACGCCGCTGGCGCC
GTTGGCGTGTGCGGCGGGAGCCCGAGCTCGTCCTTCTCGACGGGAACCT
GCCAGCAGCAGCCGGGTTTCAGCGGGGCAGACGTGCTGGGGCGGGACG
ATGACCTGATGATGTGCGTCCCCGAGTGGTTTTTAGCATGAATTAGAGTT
TATGCTGGCTAAGCCGATAGCAGCGTGGTCGAGTGTTTTTTAGCATGAAATCA
GATCTCCATCTCCCATAAAATAGCCGAGATAGCTGCTGCCGCCGCCAAATCC
TCTATAGGGCTTCAAGATCGGCAGAAACCTCTAGAAATCATCTCCCCCCTCCG
GAAAAGTCGCCTCTATTTGTCTCCATTGCCCGCGATGCAGCATCCGGTATAGC
TGCTAAGACAGGCCGCCCCTAAATCGTTTCTCCAGCGATTTTAATCTTTGGTT
TTTAGCCTGTATATATGGGCTGTGATTTGAAGTTGAGACGAGCTGGACATCAA
CTGCACGCTGATCGATTACTATTCTAGTTTGGCATAGTGTTAATTAAGTTTGG
ATGATCTCTAGGCGTGCGTTAAGTATGTAGATAGTGTTGATTAATGGCAAAA
GCTTGCAAGTTAAGTGTAGTATTGGCAGCTCTCTTGAAGATCAAATATGATGT
GTGTTATCATTTGATGATATATATTTTACTTCAGCCGTAAATAGTCTTCTTAGG
GAAGCACTGTCCATGTATGTGCTGGTAGTTGGCATTCATCTTTC
```

Example 6—HILAGE: Triticale

Haploid inducer methods: Hexaploid triticale (×*Triticosecale* Wittm.) HILAGE-based methods are conducted with standard triticale in vivo haploid induction using a cross with a maize pollen to pollinate an emasculated triticale spike, embryo rescue in tissue culture, and subsequent chromosome doubling techniques such as, but not limited to, those described by Wedzony et al. ("Factors influencing triticale doubled haploid production by means of crosses with maize," In: Proceedings of the 4th International Triticale Symposium, Red Deer, Canada. Vol 1. Juskiw (Ed.) International Triticale Association, Alberta, Canada, pp. 45-52, 1998; and *Plant Breed.* 117:211-215, 1998), Wedzony ("Protocol for doubled haploid production in hexaploid triticale (×*Triticosecale* Wittm.) by crosses with maize," In *Double Haploid Production in Crop Plants: A Manual*, Maluszynski, Kasha, Forster, and Szarejko (Eds.), pp. 135-140, Dordrecht, Netherlands: Kluwer Academic Publishers, 2003), and others. Briefly, the in vivo technique of triticale haploid induction first requires that an emasculated triticale spike be pollinated with maize pollen and treated with Dicamba (3,6-dichloro-2-methoxybenzoic acid) 1-2 days after pollination. Subsequently (18-21 days after pollination), the developing triticale embryos are removed from the spike and transferred to tissue culture. The plant is eventually transplanted to the greenhouse and treated with colchicine to double the chromosome number, and doubled haploid seed is harvested.

Endonuclease transgene and transgenic construct: Triticale HILAGE-based methods add the targeted mutagenesis component to the in vivo haploid induction system, and thus require an endonuclease. Examples of suitable endonucleases include, but are not limited to, meganucleases, ZNFs, TALE nucleases, and CRISPR/Cas-based nucleases. The endonuclease is designed to target Tsn1, but an endonuclease can be designed to target nearly any sequence. The Tsn1 gene was brought into triticale on the wheat 5BL chromosome. Thus, the description of the Tsn1 CRISPR/Cas target sites, primers, etc., described below are identical to those used for targeting Tsn1 in wheat as described herein. The endonuclease(s) are constructed using methods such as, without limitation, those described by Sander et al. (supra), Cermak et al. (supra), and Liang et al. (supra). The promoter used to drive expression of the endonuclease is endogenous or exogenous. High expression of the endonuclease is essential to increase the chance that a targeted mutation is successful before the removal of the maize chromosomes carrying the endonuclease transgene. Suitable promoters are expressed during early embryo development, and can be endogenous or exogenous. Examples are provided in TABLE 8.

The endonuclease construct also may include a selectable marker, such as herbicide resistance, to assist in recovery of the transgene during whole plant transformation and subsequent backcrossing. When present, the herbicide resistance selectable marker is driven by a promoter with strong expression in maize and or triticale. The selectable marker is not required for HILAGE-based methods, however.

In some embodiments, the transgenic construct containing the endonuclease or a second construct combined into the same maize line contains one or more copies of a sequence of DNA with homology to the DNA at and flanking the target site. This sequence of DNA may contain nucleotide changes such as one or more base pair substitutions, deletions, and/or additions. Alternatively, this sequence may contain a gene, a promoter, a regulatory sequence and or a transgene.

Testing the Endonuclease in transgenic triticale: While HILAGE-based methods do not use a transgenic triticale line to generate the final product of doubled haploid triticale with targeted mutations, it may be beneficial, though not necessary, to test the efficacy of the targeted endonuclease construct in a transgenic triticale or transgenic wheat line. Triticale transformation is conducted following techniques such as, without limitation, those described by Zimny et al. (*Molecular Breeding*, 1(2):155-164, 1995). Wheat transformation is conducted according to techniques such as those described by Weeks et al. (*Plant Physiol.* 102(4):1077-1084, 1993). Transgenic triticale with putative mutations is assessed for targeted mutations using methods similar to those described in for the *Arabidopsis* herein. Endonucleases showing efficacy for causing double stranded breaks are utilized for triticale HILAGE-based methods.

Generating a maize line to use for triticale HILAGE: One major difference between triticale HILAGE-based methods and normal doubled haploid creation in triticale is that a transgenic maize line is being used for haploid induction instead of a conventional maize line. As such, a maize line is being transformed with the endonuclease construct. The endonuclease transgene is added to the haploid inducer using any of several methods, including *Agrobacterium*-based methods (e.g., those described by Ishida et al., supra) or by particle bombardment (such as the method described by Gordon-Kamm et al., supra). Since the line used for maize transformation likely is not a prolific haploid inducer, it may be beneficial, though not necessary, to backcross the endonuclease transgene(s) into a genetic background that has previously shown high efficacy in triticale haploid induction. The backcross introgression of the transgene into a more suitable maize line may be conducted with the assistance of molecular markers to select for the presence of the endonuclease transgene, as well as to select for the genetic background of the recurrent parent (the suitable maize line) and against the donor parent line (the originally transformed maize line).

Depending on the promoter chosen to drive the endonuclease, the endonuclease will likely show different expression in the maize line than in the progeny of the maize-triticale cross. If the gene is expected to express in maize, it may be beneficial to assess the RNA and protein expression of the endonuclease to confirm that the endonuclease is functional.

Genotyping of putative mutated triticale plants: The plantlets are being genotyped before or after transplanting to soil to identify (1) if the desired targeted mutation(s) occurred (2) if the triticale plant no longer contains maize chromosomes and (3) if the transgene(s) are no longer present. Additionally, potentially different tillers may need to be genotyped as the plant could be chimeric for one or more targeted mutations. Assays to evaluate the presences of mutation(s) at the target site(s) can be conducted as described in the *Arabidopsis* section herein. The presence of maize chromosomes, could be assessed by one or more of several methods. Primers can be designed to amplify specific sequences on each of the 10 maize chromosomes in the maize line used for haploid induction, and these primers can be used to determine if the maize chromosomes are still present. Alternatively, a custom SNP chip can be designed that can be used to genotyped the triticale line and also maize DNA. In triticale plants that have lost the maize chromosomes, the triticale SNPs are able to be genotyped, but the maize SNPs are not able to be genotyped. Alternatively or additionally, a low coverage whole genome sequencing method or RNA sequencing method could be utilized to determine if the maize chromosomes are present and/or maize genes are being expressed. If the maize chromosomes have been removed from the triticale plant, it is likely that the transgene had also been removed. However, to increase industry and consumer acceptance of HILAGE-based methods, it may be beneficial to test for the absence of the transgene(s) in the triticale line. In one method, primers that amplify portions or all of the transgenic construct can be designed and used to test if any portion of the construct is in the produced triticale line. Alternatively, the sequences of the transgene can be search for in whole genome sequence or RNA sequence data, if said data are available.

Utilization of Triticale HILAGE: The maize line containing one or more endonuclease and or CRISPR guide RNAs is being crossed (as the pollen donor) to a triticale line to generate haploid progeny. Before the maize chromosomes are eliminated, the targeted endonuclease induces targeted DNA double strand breaks in the DNA from the triticale line. Some of these double stranded breaks will be incorrectly repaired and a mutation will result. The haploid progeny genomes can be doubled before or after the progeny are screened for the mutation(s). Once the genomes of these haploid individuals are doubled, the individuals can be grown out and self-pollinated to produce doubled haploid seed. Different mutations may be produced, and evaluation of each mutation event is necessary to determine if the mutation(s) obtained will have the desired result. Only EM that produce a desired phenotype are advanced.

In some embodiments, HILAGE-based methods are conducted on all (or many) of the triticale lines that may be used as parents for breeding. If populations are developed using lines that have an EM at all targeted loci, the populations will not segregate for the EM. Thus, breeding efforts are simplified by not having to conduct selections for the presence of the EM.

Advantages of HILAGE in triticale: HILAGE may play a pivotal role in generating targeted mutations in triticale. Globally, there is still resistance to utilizing transgenes in triticale. HILAGE-based methods may induce targeted mutations in triticale without the released triticale line ever technically coming in contact with a transgene placed into a triticale chromosome. In addition, it is possible that HILAGE-based methods may be more effective in triticale than in maize, since it is likely that the maize chromosomes persist longer in the maize-triticale embryo than the haploid inducer maize chromosomes persist in the maize haploid inducer-regular maize line embryo. The longer the maize chromosomes are present in the triticale embryo, the more opportunity for targeted mutations to occur.

Exemplary target sites and methods for genotypic screening in oat are provided in TABLE 19A, while exemplary primers for amplifying the target site are provided in TABLE 19B. Expected genotypic classes from the cross are shown in TABLE 20. Triticale (wheat) gene to target—Tsn1: Sequences of the target oligonucleotides were as follows (with f1/r1 being for target 1 and f2/r2 being for target 2):

*Tsn1* gene (SEQ ID NO: 30)
f1 5' GATTGCCGCTAGGGCATCTTAGAT 3'

(SEQ ID NO: 31)
r1 5' AAACATCTAAGATGCCCTAGCGGC 3'

Underlining indicates the 20 bp target sequences.

TABLE 19A

| Target Site and Methods for Genotypic Screening, Target 1 | |
|---|---|
| Endonuclease | CRISPR |
| Gene Target | Triticale (Wheat) *Tsn1* |
| Gene Target | ADH59425 |
| Target sequence | GCCGCTAGGGCATCTTAGATAGG (SEQ ID NO: 32) |
| Mutant Phenotype | Resistance to *Stagonospora nodorum*, which causes *Stagonospora nodorum* blotch (SNB); and resistance to *Pyrenophora tritici-repentis*, which causes tan spot.* |

TABLE 19A -continued

| Target Site and Methods for Genotypic Screening, Target 1 | |
|---|---|
| Endonuclease | CRISPR |
| Genotypic Screen CAPS | CAPS assay; enzymes SfaNI, DdeI, BglI, TauI, and AciI |

*Faris et al., *Proc. Natl. Acad. Sci. U.S.A.* 107(30):13544-13549, 2010.

TABLE 19B

| PCR primers for amplifying CRISPR target site, Target 1 | |
|---|---|
| Gene Target | Triticale (Wheat) Tsn1 |
| Forward Primer | 5'-TGTGCATTCTTTCCAAAAGGTCA-3' (SEQ ID NO: 33) |
| Reverse Primer | 5'-GCTCCAAAGGGCTTTAGTAGGA-3' (SEQ ID NO: 34) |

TABLE 20

Expected genotypic classes from cross: Endonucleases targeted to Tsn1
Due to the method of triticale haploidization formed from the crossing of emasculated triticale spikes with maize pollen, several classes of plant outcomes are not possible. If the triticale is emasculated correctly, no self- pollinations should occur. If a mistake is made in the emasculation process and a triticale seed is allow to self-pollinate, the seed will grow more vigorously than a triticale x maize cross, and the seed can be easily screened out. Due to the inability of triticale and maize chromosomes to pair and the inability of maize chromosomes to be inherited, classes B and C are not possible. Thus, only classes D and E are expected to be produced.

| Class | Haploid Identification Trait: embryo growth | Successful Mutation Trait: disease resistance | Phenotype indicates plant is: |
|---|---|---|---|
| A | Screened out visual as a healthy seed | na | Self-pollination |
| B | NA | na | Hybrid, not homozygous mutated |
| C | NA | na | Hybrid, is mutated |
| D | Slow growing embryo | Susceptible to SNB | Haploid, not homozygous mutated |
| E | Slow growing embryo | Resistant to SNB | Haploid, mutated |

Triticale (wheat) *Tsn1* and surrounding sequence (GENBANK ® accession number GU259618)

(SEQ ID NO: 35)

ATGACTACACCAATGAGTATACCGTTCGCAACTTTGGAAAAGATTACAAATG

GGTTCTCAAACGATTTAATAATTGGAAGGGGTGGGTATGGAAACGTTTACAA

GGTATGGCTTAATACTTGATATTTCCTTTTTTCAGCAAATGTTCAGGCTATAA

ACAAATAATTTAAGTGCAATAATTATGTCAAGCAGGCAGTTTACAAAGGGGA

AGTGATTGCTGTGAAGTTGCTTCATGATGATCTGGTGCAATTACTTGATGACA

GACAATTTAAAAATGAACTTTTTAACCTTTTGAGGGTTGAGCATCCGAATATT

```
GTTTGCTTACGTGGTTATTGTTATGAAACACGGTATAAAATTGTTAAGCACAA

TGGTGAGACAGTCTTTGGTAAACATATACACAGAGTTCTCTGCTTTGAATACT

TGGAGGGTGGAAGCCTAGACAATCATCTTCATGGTACGATGGAACTTCAAAA

TACAGTTATTTTGTTTTACGTTTAAAGGAAACTGATTTCTCATTTACATACATA

CTCTTTGTTAACTTGCGTAGCACCATCTTTGCCACCTAACTGGACCACACGTT

ACAATACCATAAAGGGGATTTGTGAAGGCTTAAATTTCCTTCACGGATGTCA

ACCACCAATTTTGCATCTTGATCTGAAGCCTGCCAATATATTAGTAGACAGTT

CCATGGTGCCTAAACTGGCGGATTTTGGATTGTCAAAGCTCTTCCATGGATCA

CATACTCATGTGACAAAACAAATCATAGGAACCCAGTAAGCGGAAGCGACC

CGTGGATTGTCTCGTTCTGAATTTTCTTTCTTTTGTGATCAAATAAATAGTATG

TACAGTTCTGTACTAACTGTGTCTTTGTATCACGCAGGAAGTACATGCCACCG

GAATTCATCAAAGATGGCAAGATCTCGGTTAAAAATGATGTCTTTAGTTTGG

GTATTGTGATCATAGAAATAATGGCAGGACCTATGGGTTATTCAGAATTTTCA

GAAATGGGCAGCGGTGCACAATTTGTGAAGGAGGTAATAAAAAAAACTCAA

GTTTGACACCCGAGTTCGTATAAATAACAAACTACCACACCAAGAATTTGAT

GTCTAATGTGTGAGCCATTATAATCGTTGAACTGAGTTTATGACAGGACCGGC

AGTAATAAAAAATATAGCAACACTCCCCCACACAATATATTGAGCATAGAAG

ATACAACTTATCTAGCTATAACAAAATAATAATCCAGAAAAGTAGCCATTTTT

TTTTCCGGACAGGATTGAGGTCCACCAGTCCAATAACTATGAAGCAGCTCGC

TGATAGAAAATTCCAAGGTACAATTATTTTTGTAAGTTTCTCCTTATCACGTG

TGAAACACCAATGTAATAAAGCTGATAAACCAAACGTACCCACTATGAGAAC

TGCATACACTGAGACTCGAAGAAAAGAACAAATGCATATCTAGAACCTTGCT

CCATGGGATATCTAGAACCTTGCTCCATGGGATCTAGCACCATCTCCATTTTG

GAGCAAGCACGAGGTGCGTATCGTAATCTTTTTCTGCTAGATGCAGACTTAG

ACACCCAGTATTCTCTAGGTAAATTATTTATCTGGAAAGTCGTAGGTAACACT

TGTGAACAAGGATATAGCGTACATATATATGGGAGCATTTGTGTTATGTGAC

ACTTTTGACTTAATTGCAAATATTATGTTATGTGAAGACTCAAGAGTGTTTTT

GAACAAGTATCGTACATATTGTACCGAAAAAGGCTTTCGCCCCGCTTTATATT

ATAAAGCACATGCCCAAGCCAACAAACCACACAGGTTCACAAACACACGCA

GACCCACACACACCAAGTTCACACACAGACAAGATCCACAAGGGTTAATGCT

GAGGGCACAGCTTAACAAGCCCTAGAACAAAAAGGAAAGACACCATCTAGT

CGGGCTCCGGGGGGGGGGGGGGGCGGCGGAAGTGGAGGCGCCAGG

CGGAAGGCGAGCGATCGAAGGTCGGCGAGGAGGGTGTTGATGATGTCCCGA

TCCTGAGGGCGGCTAAGCGGCCGCCAAAGCTGCAAGTACCCACACATTTTAA

AAATGGCGTCAGTAGCGCGTCGTAGAGGGACTTTTTGGATGACAAGCTTATT

GCGGACGGTCCACAGCGTCCAGCCGAGAACCCCAACGCATAACCAACGGAT

ATGTCGGTGGCGTGGGGGGGAGGCGTGGATTTCCGCGAGGAGGTCGGGGA

AGTTGGAGTTGCACCACTATCCGCCAACCGTCTCACGGAAACTGGACCAAAG

AAACTGGCCGCAGGGCACGTGAAGAAGATGTGGTTAGCATCCTCCGCAGTGC

CGCACAAGGGGCAAAGCCCATCCCCGGGTCCGTTGCGCTTGAGGACTTCGAC
```

-continued

```
ACCGGAGGGGAGGCGGCCACGAATCCACTGCCAAAGGAAGATCCTAATCTTC
AGAGGTAAGCGAATGTCCCAGATCAGAGCAAAGGGCTCGGGCGCGGGCGAA
GGCGCAATAGCCGCGTACATGACCTAGTAGAGAAACGACCGGAGGACTCTA
GGCGCCACGAGATGGCGTCCGGGCGTCGGTGACGCTCATCGGAAGAAGGG
CGATGTCCTGGAGGAGGGAATCCCAGGCGGCCACTTCGGGGGGACCGAAAG
GACGACGAAACGCGAGGCGCCCTAAGTCAATAAGGGCCGTCTCGACAGAGA
CCCGAGGGTCAACCGCAATGGTGAAGAGATCGGGAAAGCGGGCGGCCAGAG
GGGTGTCACCGAGCCACCGATCAAACCAGAACAGGGTCGCGGACCCAGTAC
CAATCGAAATGGACGTGCCGATACGAAGCACAGGAAGCAGCCGCACGACGG
CCTGCCAAAACTGTGATCCGCCCGAACGCTGACAGAAAGCCAGAGGCTGGCC
ACGGAGGTATTTGTTGCGGATAATGGTGAGCCACAACCCTCCGTCACCATTG
GCAATACGCCACAACCACCGGGTCAGGAGGGCGATGTTCATTCGGCGGGAG
GACAGAATCTCAAGACCCCCCTGGTCTTTAGGTTTACAAATGTCCGGCCAAGT
CACCATGTGGTACTTCTGTTTGTCATCGTCGCCAGCCCAATAGAACCTGGATT
GGTACTTGGCAATTTCCGTGTGCAGCGTTTCATGGAGGCTATAAAAGCTCATG
AGGAACCAAAGGAGACTGGCGAGTGAGGAGTTGATGAGGATCACCCGCGCC
GCCTTTGATAGCCAACGCCCTTTCCAAGGTTCGACGCGGTGTTGCATACGGGT
CACCGTAGGGTGGAGGTCCGCCACGGTGAGGCGCGAGTCACTAACGGGGAT
CCCCAGGTAGGTCGTGGGGAAGGACCCTAGCCGACAGTTCAGGCGATCAGCA
ATATCCTGAGCCTCCTCCGGAGGGTATCCAAGGACCATCACCTCGCTCTTATC
AAAGTTAATCGTAAGGCCCGACATCTGCTGGAAGCACAGGAGGAGGAACTTC
AGGTTAGCAACATCCTGATTTGAACCTTCCACCATTATTATGGTGTCGTTCGC
GTATTGCAGGAGGGAGACCCCTCCCCCTCCAACTAGGTGAGGGACAATGCCG
TGGATATGGCCAGCACCCTTAGCCTTATCCAGGATGGCGGCCAGAGCATCGA
CCACCATGTTGAACAGGAACGGCGAGAATGGGTCTCCTGACAGACCCCACAG
AGGGTGGGAAGTATGGCCCAATCTCGCCGTTAATGTTCACCGCCGTCTTTCC
ACATGAAACTGATTGCATCACGCGGGTCACCCAGCGGTCATCAAAGCCCTTA
CGCAGCAGTACTTCCCGAAGGAAGGGCCAGTGAACAGTATCATAGGCTTTAT
GGAAGTCAAGCTTCAGGAACACAGCACGAAGATGCTTCACCCGGACCTCGTG
AAGGACTTCATGGAATACCAACACGCCATCAAGAATAAACCGGCCTTGGATG
AAGGCCGATTGGTTCGGGTGAGTGATCGAATCAGCCAGCAGGGTCACCCTAT
TGGCGTACCCTTTGGCCAGGATCCGAAAAATCACGTTAATCACCGTGATGGG
GCGGAACTGGCGAATATCAGAGGCACCCGGAACCTTTGGGATGAGGGTAATG
ATCCCATAGTTGAGGCGTCCCAGGTCCATCGAACCCGAATAGAACTCCTCGA
ACAAAGCCATGACCTCCGGTTTGACCGCCTGCCAGAATGTTTTAAAGAAAGC
AACAGGCAGGCCATCCGGGCCTGGGCCGAGGCGGGGTTCATGCCTTTAATG
GCCGCGAGCACCTCGTCCTCGGCGAAGGGAGCAACCAGGGCCGCATTGGCCT
CGCCGGGAACCAACTGCGCCCCCGTCCAAGTATCGGGGGCATCGTACATATT
GTTATATGCTCCATCTCTAATTGTATCTCTATATTTCGGTTTTGTAGGTACTTA
CCAATTGGAGTACTATCATTAAAGCTACATCAGAGTATCCAGCAGAGGAACT
ACATCAAGTGAATTTGTGCATCGACATAGCAATGCTTTGTGTGGATTCTGAAA
```

-continued

```
GAGTCAATAGACCCACCATAGCTGGTATCCTAGATGCATTGAATAGGACAAA
AACTCATATGCCCTCCTCTACGAAAAAAACTCATATTCCCTGGGGACAGGTAT
GATTTGCATACTTGCAAACAAAATGAAATCTCGAGTATATATTTGCAATCTGT
AGAAGACAGTTGCTTGGATATATGGACCACTAAGTAGTTATAGAGTTTGCAG
CTCCCCGTCTCCCACTCATTTTATTCTCAATCAAGTAGTTCTTTAATAGTCAGG
AACTTGCTTACTGCATCCTTTTGACTCCCTGCTCTATAATCCATGTAGAAGAA
CCTTCATTTTAGTTCCGGCTAATTCCAGGAATAGAAAACTAGAGAGGGCCTAT
TCGTAATCGTGCCTTCCGGAGTGACAGGCTAAGTGAAGGGCAGGGGGATGCT
GCCCTCGACAACCGTGGCTGTGATTGGCACTGTCGTGCTCATACGAGGTACC
AGACGGTGTAGAAGTTAACCTAGTTGATTAATCTTAGGTGTGGTCATGCTAG
ATAGCTATATGAAAGAGCCATACATGTAGTTCAAGTAGTGCATGCAAGATTC
CAACATTCAAAATCGTGCCTTGTACTATGGAAGGGGAAAGGGAGGGGTAACA
CGTAATGAGTGCCCTATAAGCCTTACACAATAGCTTTATCAGACCACTGTGGC
GCCCTAACTGACGCCAACAGAGGTAGCTGCAATGGTTCGATGAGATAGCGGT
GAGAGAGAAGGGGCAGGGGGACATTGGTGGCAGGTGTAAGGGAAAAAGGG
AGAGGAGTGAAGCCGGCTGGGTACCTTGGTGGGGGAGAGGAAAGGGTGGAG
GAAGAACAAAGAGGTGAGGCGCCTGCTAGTGATTGCACTGTAAGCCTACCGC
GCGACATTGCTCCAAAGCTACGCTCTCCCAATAAAGGAGAACTTCTAGAGAG
TTGATATGAATTAAAGAGATTACCACAGACTCACATAGTGCCTGAGGTATTA
GCCACATTTCCTTTCATGCCCTTGCCGAGGGGCTTTCCTCGGCGCCTCTCACTT
TGGGCTTTGCTTCTTCAAAGGTGGTGTTTAGGCCGCAAAGAGTACAACCAGT
GTGTTATGTGTGTGCACTTTCGGTGTGTTACAATTTGCCATTATTGCTTGATGC
TTTATTACTATTCAAAATAGTTTCTCTTTTTCCAAGTTGTCATTTTAACATAGC
ATTATAGATTTTGTCCTTCCGATTTGCATGTTTTGATCGTCTATAACTTAGTTT
ACATAATGGAAGCACATCCCAGAGAGTAAATTGATCATGAGATCTTGACCAT
GATGATTCTCCTGTTTTTTCCTTGTACTTACACATAAAAGTTGTTTCAGTTGG
AAGATGTGCCCCTGTGTTCGACAATTGGTCCCAAAAGTACGAGTAAAAGGTC
GAACCCAGTTCCCACAAAGGAAAATAAAAGGTTGAAGATGATGACAACTGA
AGTGGACAATATCGCGAACAAACACCAACAGTTTAATTGCATGCCAGGAGAT
AGCTCTAAAACTATTGTTCAGCAAGTTCCAGACAGGGAAACATCATCAGATG
TGGAACCGACATTAATCATTGGAAGGGATGAAGAAAAACATAAAATATTGTC
CATTTTATCTGAGAGCAACGCAGAAGAGATGACCATCCTTCCAATATATGGC
ATCGGAGGAATTGGCAAGACAACCTTGGCACAATTGGTGTTCAATGACATAC
AGTTCCGGGACTACTATCGGGTGTGGGTATATGTTTCTCAGAAGTTTGACTTA
AAGAAAATTGGCAACTTTATAATATCACAGTTAACAAAAGAGACCAGCGATA
TAGATGACCAGCAGACACTTCATAATCGCCTTAGACAGCTATTTGCTGGTAA
GAGTATCCTTATTGTTTTAGATGACCTGTGGGAGGAGAAACAACATGAGTTA
GAGAAATTGAAGGCTATGCTAAGGCTTGGCATAGGAAACAAGGTTGTCATAG
TAACTACACGTGATGAAGCCATTGCAAGGAAAATCAACAGGACTGTTATGCC
ATACAAGCTAGAGATTTTAACAGATGATATGTGCTGGTCTATAATAAAACAA
```

-continued
```
AAAAGTTTCTTTGAAGATCGATGTGACAAAGAACAATTGGGGCAGATCGGAA

TGGACATTGCAATCAAGTGTGGAGGTGTGGCTTTGGCGGCTCAATCACTTGG

GTACATGTTGAGGGAGATGGAGTCTGACCAATGGGAGTCAGTGAGGGACAGT

TATATCTGGAATCTATCTACTATGGAAGATCCATCATTAAGAAATCATGAAGT

GCTTCTGTCCTTGCTGTTAAGCTATTCCCATATGCATGAATTCTTGCAGTTATG

CTTTTCCTATTGTGCATTCTTTCCAAAAGGTCAAAATATAGTGAAGTATGATC

TAATTCACCAGTGGATAGCTCTTGGATTCACCGGTCCATCTGGAATATTTGAT

TCTATTCAGCTCTGTGAGAAATATATTACACGGCTTTTGGGGATGTCATTCCT

TCAATATTCAAAGACACGTTCGGTGAGTTACTACATACTCTCGATGTCCCAAA

AGATAGCTATGGGTAGTTTCTTCATGTCAAAGAGTCCCCTTCCAGTACTGCTA

GGTGTCAGGTTTCTAGAAGGCCGCTAGGGCATCTTAGATAGGGTCATAGTTA

TACACTACTCATCCTCAAATGCATATGCCTGTGCAATTTTCTTTTCTAGATGAC

CTTCTCGACAAGCTCGTTGACATTTATCCTTTTTCTTTTTCTTTTCTTTCCCTTG

TTTTCAACCTTACCTTTCAAATTTCCTTTTCCAAGAATGACATTCAAGTCCATA

ACCTGATCGTGGATATGGGTCCTACTAAAGCCCTTTGGAGCTCAATATTTTTC

AACTATTTCATTAAAATGAATTCACATCTATAATCATCATTTCTTTTGTTATGT

ATGTATATAAAACAATACTAATTATTGTTGAACTAATAAACACATCGTTGATT

ACCTCTAAACAAATTTGAATGTCATTAAATTTGTCTTCATATTTTTTAGTGGG

ATAAGACCCCAATCCAACAGGCGCCCAAACAAATGGACCTATGTACTGAAAC

GTTGCTGTTGCTGGTGCATTTGTAGTGCTGGGTATTAATTTTAGCAGGTTTAA

GATGAAAACCACTGCAGATATTTATCCCAGGCATTATTTCATTTGATATAAGC

TTTGAAGTTTACAGATCCATAGTGTAATCTACTCTGGTGTAATTTAAATATAC

TGATCCGTTGCCCATTATCGAGAAAACATACAGCTACGGTTACACTCTTTTAT

AGTGATACAAAAGTATTTCTGTTGATAAAATATACTACTATAAAACAAAATA

AATTCAATATTCTAACAACATTACGTGGTTTTGCTGCAGAGTGATGAACGGCA

GGACAAAGATGTTAAAATGTTTGTAATGCATGACCTAGTGCACGATCTTGCA

AGAGCAATATTGGCTGATAAAGTTAATAAAGAGGGTGATGCTGTGGGAAGCA

GTTGTCACTATGCATTGCTCACAGATTGTAGCAAGCCATTGCAGTTGTCTGTT

AGTTCAACTGAATATAGCCGGTTCAATTTTTTTCTTAGCCTGTTTAAAAAGAA

GAGTTCACATGAAAATATAAAGGCGTTACGTTTTCTGAACTGTGGCAAAGTA

CTACTTCGCGGTGATGCATTTTCACCTGCCAAGTTCCTCCTTGTCTTAGATCTA

AGTGAATGCTTTATTCAGAAGCTCTCACTTGATTCGATTGGACAACTGAGGCA

CTTGAGATATCTTTGTGCTCCACGGGTCAACGATTACACGATTCCCAACTGTA

TCACCAAGCTCTCAGAATTAACTTACCTCAACCTTAGAGGCTCTTGTCGTATC

TCAGCATTGCCAGAGTCAATTGGCGATATGAAAAGTCTGATGCATCTTGATTT

ATCAGGCTGCTGTGACATAATTGAACTCCCAGTATCATTTGCGAAGCTGAAA

CAGTTGGTGCATCTAGATTTATCACACTGTCACGTGTCTGTATCAGAAGATTT

TGGTGGCTTTACCAAACTTCAATATTTGAATTTATCAGTTTTGTTTAGTTCTTC

CAAGGGGCATAGGAGAGGACTGCTAGAGGTCATTGGCAATTTAAAGAAACTC

AGGTATCTAAATCTATCTCGGTGCATGGAGGACATAGCCACATCAGAAAACC

AAATTGGCAGTTTGCTTGACTCTATCAGTACCCTTTCCAACCTTGAGCATCTG
```

```
GACTTGTCTGAGAATAAACAGCTTTCCAGTATACCAGAAAGTATGGGCAACC

TCAGGAAGCTTCATACATTGGACCTCTTAGGCTGCTATCAACTAGAGAAGCTT

CCTGATAGTATGATTAATATGGTTAGCCTGAAGGTTCTAAATGTGGGTAATTT

GGTTACACTGGATGAATCTGTGCTCTCTTTGTTAAATATTGCCTCCTTGCCAC

ACTTTGTGGTGCATGCTTCAAGTGGTAAATGTAGCAGCAATATCACCCGTCTT

CAGGCTACAAATCCTGATAGACTGATTATAGATAGACTTGAAAATGTCAAAT

CTGCAGAAGAGGCACATAACATAAAACTGATAGAGAAACAGAAAATTGAAA

CCCTACAATTTGAATGGACTGTGGCTGCTAGGAGGTTTGTGGATGACAAAGA

GGTGTTGGAAAAACTAGTGCCGCCAAGCAGTGTCGACAGTTTGTGTATAATT

GGTTATAGAAGTGTCAGCATTCCTGATTGGCTTCTGGGTATTAGTCAGTATCT

CCCTAATCTTGCGATTATAAGTCTGGTTAATTTTTCTAAGTGCAAGAACCTAC

CACCACTCGGTCAACTACCAAACTTACAATGGCTGACTCTCAGCAGTATGGA

TGGTTTGGAGGAGTGGAACACGACATATACTACTGGAGAGCAAGGTAGAAA

CGAACTCTTGTTCCCTAAGCTTGAGAGATTAAACATACATGACTGTGCCAAGT

TGAGGATAGAACCATGTCTGCCTAGAGCTTTGTATTTGCGCATACGAGATAGT

AATAATGTGCTATCCTCACTCAATACAAGAGAGCAAGCTGAGAGCACGCTGC

CCTCGGACATAGCACATTGTGATAATATGATATCAGCATGCGGAAAGAGTTC

GTCATACAGCGGTGCTTCCTCTTCTTCTCCAATAACTGATCTGTTTGTAGAGG

AAAGCAAACTACCCTTGCATCAGTGGAGGTTGCTTCACCAACTCCCCGCGCT

CCGTGGTTTACGGATCAAACATTGCAGTGATCTGACCACCTCACTTGCTGTTA

TCCAAAAACTCTCCTCCCTCCAAAATTTGAGCCTGGAGCTCAACGACCATGA

ACTGCCGAGTTGGTTGATTCAGCTGACAGATCTACAGGAATTAAAGCTTATG

CATTGCAATAGCATTACATCACTACCACAGTGGTTTGGAGAACTTGCATCTCT

CAAGAGAATTGAGATCAAGTACTGCAAGGGGATCAGCTCTTTGCCGGAGAGC

ATACAACAACTGACTAAGCTTGAATTTCTAAGCATTCATGGCTGTCCTGTATT

AGAGGAGTGGTGTGAATCAGAGGAGAACAAGATGAAGCTCACTCACATCAA

AGTTGAGGTATGTGCGTGCAAGTTATCTGTTGTATTGCTTTTATTCTCGTGCTG

GTAGTGACTTAATACTCTTTTCTTAAATGGCAAGTATACACATGCCATGAGTA

TCTTTACATAATCATGGTAAGTGTTGAATTAGGTGTATGTATTTTGTCTATTAG

ATGCTTCATGTGTCTAGATTACTTGACAAAAATATGTGACGACTGCATTAATA

ATTCGCCTAAGAAGAAAAGCATTCCAGTTGTGATTGTGCTATATCATGCACCT

ATACATGCATTGTTCTGATTATATATCCCGTTTGCATTGTTCAGATCGCTGGA

CGGGATTCGGTAGGCTTTGAGGATTCGAAGGTTCAGATTGTCAAACCAATGC

CAGCACAAATGGTTCGCCAATCAGCATTTGCTACTACAGAACGAAGATAG
```

Example 7—HILAGE-HR

To conduct HILAGE-HR, an endonuclease is generated to cause a double strand break in a specific sequence. Initial studies utilize an endonuclease targeting maize Bm3 ZEAMMB73_595664, using the same CRISPR target sequences described above:

```
                                           (SEQ ID NO: 19)
f1 5' GATTGGGCTCCACCGCCGGCGACG 3'

(SEQ ID NO: 20)
r1 5' AAACCGTCGCCGGCGGTGGAGCCC 3'
```

Underlining indicates the 20 bp target sequences.

The donor template consists of three fragments of DNA that are synthesized into a single fragment in order. The first fragment is a DNA sequence homologous to the sequence upstream of the target site, and can range in size from 10 nucleotides to 1,000 or more nucleotides. The second fragment is the sequence GGGCCCGGCGACG (SEQ ID NO:49), which contains a 7 bp deletion relative to the wild-type and causes a frame shift mutation. The third fragment is DNA sequence that is homologous to the DNA sequence downstream of the target site, and can range in size from 10 nucleotides to 1,000 or more nucleotides.

One or more copies of the endonuclease and one or more copies of the donor template are placed into the genome of a maize haploid inducer line, either by directly transforming the inducer line with the sequences or by first transforming the sequences into a different maize line and backcrossing the sequences into the inducer line. The haploid inducer line with the endonuclease(s) and the donor template(s) line is called the HILAGE-HR line.

The HILAGE-HR line is crossed to an elite line having a sequence that matches or closely matches the endonuclease target sequence. The HILAGE-based process is conducted as described herein, with the modification that in some individuals, the DSB is repaired using the donor template sequence. The specific DNA modifications produced by the DSB being repaired using the donor template are detected using methods such as PCR and sequencing. The chromosome-doubled plants are screened to identify plants that contain the desired insertion and do not contain chromosomes from the haploid inducer line.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for generating a doubled haploid plant cell comprising a transgenic DNA sequence inserted at or near a selected DNA sequence, said method comprising:
   (a) transforming a haploid inducer line with (i) a first transgenic DNA sequence flanked on both sides by DNA sequences homologous to sequences upstream and downstream of the selected DNA sequence, and (ii) a second transgenic sequence that encodes a rare-cutting endonuclease, to generate a Haploid Inducer Line for Accelerated Genome Editing (HILAGE) stock line having the first and second transgenic DNA sequences stably integrated therein, wherein the transgenic DNA sequence encoding the rare-cutting endonuclease is operably linked to a promoter that is expressed in plant embryos during at least the first and second cell divisions after fertilization, and wherein the rare-cutting endonuclease is targeted to the selected DNA sequence;
   (b) crossing the HILAGE stock line with a targeted line to generate an $F_1$ zygote comprising the stably integrated first and second transgenic DNA sequences;
   (c) culturing the $F_1$ zygote such that (i) the rare-cutting endonuclease is expressed and cleaves chromosomal DNA of the targeted line at or near the selected DNA sequence, and the first transgenic DNA sequence is inserted at the site of cleavage, and (ii) genome elimination takes place such that chromosomes from the HILAGE stock line are eliminated, resulting in a haploid cell; and
   (d) inducing chromosome doubling in the haploid cell to generate a doubled haploid plant cell comprising the first transgenic DNA sequence but not the second transgenic DNA sequence.

2. The method of claim 1, wherein the plant cell is from maize, wheat, barley, triticale, *Arabidopsis*, oat, pennycress, tomato, potato, soybean, or camelina.

3. The method of claim 1, wherein the rare-cutting endonuclease is a TALE endonuclease, a CRISPR/Cas-based nuclease, a ZFN, or a meganuclease.

4. The method of claim 1, wherein the promoter is a cauliflower mosaic virus doubled enhanced 35S promoter, a maize ZmUb1 promoter, or a rice APX, OsCc1, EIF5, R1G1B, PGD1, Act1, or SCP1 promoter.

5. A method for generating a doubled haploid plant cell comprising a first transgenic DNA sequence inserted at or near a selected DNA sequence, said method comprising:
   (a) transforming a plant cell line with (i) a first transgenic DNA sequence that is flanked on both sides by DNA sequences homologous to sequences upstream and downstream of the selected DNA sequence, and (ii) a second transgenic DNA sequence that encodes a rare-cutting endonuclease, to generate a transgenic plant cell line having the first and second transgenic DNA sequences stably integrated therein, wherein the transgenic DNA sequence encoding the rare-cutting endonuclease is operably linked to a promoter that is expressed in plant embryos during at least the first and second cell divisions after fertilization, and wherein the rare-cutting endonuclease is targeted to the selected DNA sequence;
   (b) crossing the transgenic plant cell line to a haploid inducer line to generate a HILAGE stock line that is homozygous for the first and second transgenic DNA sequences, has the first and second transgenic DNA sequences stably integrated therein, and has the majority of its DNA from the haploid inducer line, where the HILAGE stock line can induce haploids upon crossing;
   (c) crossing the HILAGE stock line with a targeted line to generate an $F_1$ zygote comprising the stably integrated first and second transgenic DNA sequences;
   (d) culturing the $F_1$ zygote such that (i) the rare-cutting endonuclease is expressed and cleaves chromosomal DNA of the targeted line at or near the selected DNA sequence, and the first transgenic DNA sequence is inserted at the site of cleavage, and (ii) genome elimination takes place such that chromosomes from the HILAGE stock line are eliminated; and
   (e) inducing chromosome doubling in the haploid cell to generate a doubled haploid plant cell comprising the first transgenic DNA sequence but not the second transgenic DNA sequence.

6. The method of claim 5, wherein the plant cell is from maize, wheat, barley, triticale, *Arabidopsis*, oat, pennycress, tomato, potato, soybean, or camelina.

7. The method of claim 5, wherein the rare-cutting endonuclease is a TALE endonuclease, a CRISPR/Cas-based nuclease, a ZFN, or a meganuclease.

8. The method of claim 5, wherein the promoter is a cauliflower mosaic virus doubled enhanced 35S promoter, a maize ZmUb1 promoter, or a rice APX, OsCc1, EIF5, R1G1B, PGD1, Act1, or SCP1 promoter.

9. A method for generating a doubled haploid plant cell comprising a transgenic DNA sequence inserted at or near a selected DNA sequence, said method comprising:
   (a) crossing a HILAGE stock line with a targeted line to generate an $F_1$ zygote comprising a stably integrated transgenic DNA sequence, wherein the HILAGE stock line comprises (i) a stably integrated first transgenic DNA sequence flanked on both sides by DNA sequences homologous to sequences upstream and downstream of the selected DNA sequence, and (ii) a stably integrated second transgenic DNA sequence that encodes a rare-cutting endonuclease, wherein the transgenic DNA sequence encoding the rare-cutting endonuclease is operably linked to a promoter that is expressed in plant embryos during at least the first and second cell divisions after fertilization, and wherein the rare-cutting endonuclease is targeted to the selected DNA sequence;
   (b) culturing the $F_1$ zygote such that (i) the rare-cutting endonuclease is expressed and cleaves chromosomal DNA of the targeted line at or near the selected DNA sequence, and the first transgenic DNA sequence is inserted at the site of cleavage, and (ii) genome elimination takes place such that chromosomes from the HILAGE stock line are eliminated; and
   (c) inducing chromosome doubling in the haploid cell to generate a doubled haploid plant cell comprising the first transgenic DNA sequence but not the second transgenic DNA sequence.

10. The method of claim 9, wherein the plant cell is from maize, wheat, barley, triticale, *Arabidopsis*, oat, pennycress, tomato, potato, soybean, or camelina.

11. The method of claim 9, wherein the rare-cutting endonuclease is a TALE endonuclease, a CRISPR/Cas-based nuclease, a ZFN, or a meganuclease.

12. The method of claim 9, wherein the promoter is a cauliflower mosaic virus doubled enhanced 35S promoter, a maize ZmUb1 promoter, or a rice APX, OsCc1, EIF5, R1G1B, PGD1, Act1, or SCP1 promoter.

* * * * *